US008735385B2

(12) United States Patent
Gao

(10) Patent No.: US 8,735,385 B2
(45) Date of Patent: May 27, 2014

(54) SUBSTITUTED PHENYL CYCLOALKYL PYRROLIDINE (PIPERIDINE) SPIROLACTAMS AND AMIDES, PREPARATION AND THERAPEUTIC USE THEREOF

(71) Applicant: Sanofi, Paris (FR)

(72) Inventor: Zhongli Gao, Bridgewater, NJ (US)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/670,111

(22) Filed: Nov. 6, 2012

(65) Prior Publication Data

US 2013/0065877 A1 Mar. 14, 2013

Related U.S. Application Data

(63) Continuation of application No. PCT/US2011/035826, filed on May 10, 2011.

(60) Provisional application No. 61/333,394, filed on May 11, 2010.

(51) Int. Cl.
C07D 207/06 (2006.01)
C07D 401/12 (2006.01)
C07D 403/10 (2006.01)
C07D 405/12 (2006.01)
C07D 409/12 (2006.01)
C07D 413/12 (2006.01)
C07D 417/10 (2006.01)
C07D 491/107 (2006.01)
A61K 31/407 (2006.01)
A61K 31/403 (2006.01)
A61K 31/438 (2006.01)
A61K 31/40 (2006.01)

(52) U.S. Cl.
USPC ........ 514/210.2; 514/409; 514/278; 514/429; 514/329; 514/422; 514/378; 546/16; 546/208; 548/408; 548/409; 548/577; 548/578; 548/517

(58) Field of Classification Search
USPC ............... 514/278, 409; 546/15, 16; 548/408
See application file for complete search history.

(56) References Cited

U.S. PATENT DOCUMENTS

| 3,960,961 | A | 6/1976 | Lednicer | |
|---|---|---|---|---|
| 7,223,788 | B2 | 5/2007 | Schwink et al. | |
| 7,517,991 | B2* | 4/2009 | Sher et al. | 546/195 |
| 7,534,891 | B2* | 5/2009 | McArthur et al. | 546/169 |
| 7,678,807 | B2* | 3/2010 | Diaz Martin et al. | 514/279 |
| 7,790,720 | B2* | 9/2010 | Celanire et al. | 514/236.8 |
| 8,088,808 | B2 | 1/2012 | Czechtizky et al. | |
| 8,217,052 | B2 | 7/2012 | Gao et al. | |
| 8,222,290 | B2 | 7/2012 | Czechtizky et al. | |
| 8,227,481 | B2 | 7/2012 | Gao et al. | |
| 8,227,504 | B2 | 7/2012 | Czechtizky et al. | |
| 8,252,824 | B2 | 8/2012 | Czechtizky et al. | |
| 2010/0173897 | A1 | 7/2010 | Czechtizky et al. | |
| 2012/0258979 | A1 | 10/2012 | Gao et al. | |

FOREIGN PATENT DOCUMENTS

| EP | 1669350 | 6/2006 |
|---|---|---|
| WO | WO 2004/037257 | 5/2004 |
| WO | WO 2005/087746 | 9/2005 |
| WO | WO 2005/117865 | 12/2005 |
| WO | WO 2006/047256 | 5/2006 |
| WO | WO 2006/132914 | 12/2006 |
| WO | WO 2007/093364 | 8/2007 |
| WO | WO 2007/133561 | 11/2007 |
| WO | WO 2009/036117 | 3/2009 |
| WO | WO 2009/039431 | 3/2009 |
| WO | WO 2009/052062 | 4/2009 |
| WO | WO 2009/052063 | 4/2009 |
| WO | WO 2009/052065 | 4/2009 |

(Continued)

OTHER PUBLICATIONS

U.S. Appl. No. 13/483,503, filed May 30, 2012, Gao, et al.
U.S. Appl. No. 13/668,998, filed Nov. 6, 2012, Gao, et al.
U.S. Appl. No. 13/670,010, filed Nov. 6, 2012, Gao, et al.
U.S. Appl. No. 13/670,026, filed Nov. 6, 2012, Gao, et al.
U.S. Appl. No. 13/670,046, filed Nov. 6, 2012, Gao, et al.
U.S. Appl. No. 13/670,067, filed Nov. 6, 2012, Gao, et al.
U.S. Appl. No. 13/670,082, filed Nov. 6, 2012, Gao, et al.
International Search Report for WO2011/143150 dated Nov. 17, 2011.
Hancock, The Challenge of Drug Discovery of a GPCR Target: Analysis of Preclinical Pharmacology of Histamine H3 Antagonists/Inverse Agonists, Biochemical Pharmacology, vol. 71, (2006), pp. 1103-1113.

(Continued)

Primary Examiner — Sabiha N Qazi

(57) ABSTRACT

The present disclosure relates to a series of substituted phenyl cycloalkyl pyrrolidine (piperidine) spirolactams and amides of formula (Ia) and formula (Ib).

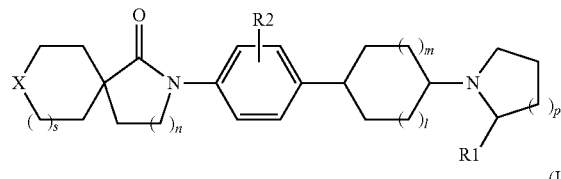

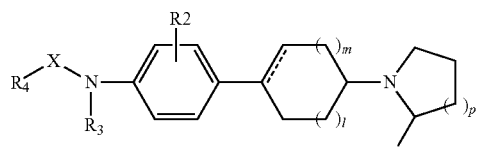

wherein $R_1$, $R_2$, $R_3$, $R_4$, X, m, l, n, p and s are as described herein. More specifically, the compounds of this invention are modulators of H3 receptors and are, therefore, useful as pharmaceutical agents, especially in the treatment and/or prevention of a variety of diseases modulated by H3 receptors including diseases associated with the central nervous system. Additionally, this disclosure relates to methods of preparation of substituted phenyl cycloalkyl pyrrolidine (piperidine) spirolactams and amides of formula (Ia) and (Ib), and intermediates therefor.

5 Claims, No Drawings

(56) References Cited

FOREIGN PATENT DOCUMENTS

| WO | WO 2009/052068 | 4/2009 |
|----|----------------|--------|
| WO | WO 2010/007382 | 1/2010 |
| WO | WO 2010/047956 | 4/2010 |
| WO | WO 2010/065798 | 6/2010 |
| WO | WO 2010/065803 | 6/2010 |

OTHER PUBLICATIONS

Esbenshade, et al., Histamine H3 Receptor Antagonists: Preclinical Promise for Treating Obesity and Cognitive Disorders, Mol. Interv., (2006), vol. 6, No. 2, pp. 77-88.

Old, et al., A Highly Active Catalyst for Palladium-Catalyzed Cross-Coupling Reactions: Room-Temperature Suzuki Couplings and Amination of Unactivated Aryl Chlorides, J. Am. Chem. Soc., (1998), vol. 120, pp. 9722-9723.

Wolfe, et al., Simple, Efficient Catalyst System for the Palladium-Catalyzed Amination of Aryl Chlorides, Bromides, and Triflates, J. Org. Chem., (2000), vol. 65, pp. 1158-1174.

Van Der Poel, et al., Temporal Patterning of Ultrasonic Distress Calls in the Adult Rat: Effects of Morphine and Benzodiazepines, Pschopharmacology, vol. 97, pp. 147-148, (1989).

Porsalt, et al., Depression: A New Animal Model Sensitive to Antidepressant Treatments, Nature, vol. 266, (1977), pp. 730-732.

Voskresensky, et al., Selective One-Pot N-Monomethylation of 2-Nitroanilines Under Ptc Conditions, Synthetic Communications, vol. 30, No. 19, pp. 3523-3526, (2000).

Cho, et al., Direct and Indirect Reductive Amination of Aldehydes and Ketones With Solid Add-Activated Sodium Borohydride Under Solvent-Free Conditions, Tetrahedron, vol. 61, (2005). pp. 5725-5734.

Nagumo, et al., Synthesis of (−)-TAN1251A Using 4-Hydroxy-L-Proline as a Chiral Source, Tetrahedron, vol. 58, (2002), pp. 9871-9877.

Stafford, et al., Asymmetric Total Synthesis of (−)-Secodaphniphylline, J. Org. Chem., (1990), vol. 55, pp. 5433-5434.

Boiteau, et al., High Efficiency and Enantioselectivity in the Rh-Catalyzed Conjugate Addition of Arylboronic Acids Using Monodentate Phosphoramidites, J. Org. Chem., vol. 68, pp. 9481-9484, (2003).

Takaya, et al., Rhodium-Catalyzed Asymmetric 1,4-Addition of Aryl- and Alkenylboronic Acids to Enones, J. Am. Chem. Soc., (1998), vol. 120, pp. 5579-5580.

Nguyen, et al., The First General Palladium Catalyst for the Suzuki-Miyaura and Carbonyl Enolate Coupling of Aryl Arenesulfonates, J. Am. Chem. Soc., (2003), vol. 125, pp. 11818-11819.

Denhart, et al., Conformationally Restricted Homotryptamines. Part 5: 3-(Trans-2-Aminomethylcyclopentyl) Indoles as Potent Selective Serotonin Reuptake Inhibitors, Bioorganic & Medicinal Chemistry Letter, vol. 19, (2009), pp. 4031-4033.

Evarts, et al., An Efficient and Convenient Synthesis of Enantiopure 4-(t-Butyldimethylsilyloxy)-cyclohex-2-en-1-one: A Formal Synthesis of (±)-Mesembranol, Tetrahedron Letters, vol. 42, (2001), pp. 3673-3675.

Lott, et al., Trimethylsilyl Iodide as a Peptide Deblocking Agent, J. Chem. Soc., Chem. Commun., (1979), pp. 495-496.

Comins, et al., Pyridine-Derived Triflating Reagents: An Improved Preparation of Vinyl Triflates From Metallo Enolates, Tetrahedron Letters, vol. 33, No. 42, pp. 6299-6302, (1992).

\* cited by examiner

SUBSTITUTED PHENYL CYCLOALKYL PYRROLIDINE (PIPERIDINE) SPIROLACTAMS AND AMIDES, PREPARATION AND THERAPEUTIC USE THEREOF

This application is a continuation of International Application No. PCT/US2011/035826, filed May 10, 2011, which claims the benefit of priority of U.S. Provisional Application No. 61/333,394, filed May 11, 2010, both of which are incorporated herein by reference, and which also claims the benefit of priority of French Application No. 1061079, filed Dec. 22, 2010.

BACKGROUND OF THE INVENTION

1. Field of the Invention

The present invention relates to a series of substituted phenyl cycloalkyl pyrrolidine (piperidine) spirolactams and amides. The compounds of this invention are modulators of H3 receptors and are, therefore, useful as pharmaceutical agents, especially in the treatment and/or prevention of a variety of diseases modulated by H3 receptors including diseases associated with the central nervous system. Additionally, this invention also relates to methods of preparation of substituted phenyl cycloalkyl pyrrolidine (piperidine) spirolactams and amides and intermediates therefor.

2. Description of the Background Art

Histamine is a ubiquitous messenger molecule released from mast cells, enterochromaffin-like cells, and neurons. The physiological actions of histamine are mediated by four pharmacologically defined receptors (H1, H2, H3 and H4). All histamine receptors exhibit seven transmembrane domains and are members of the G-protein-coupled receptor superfamily (GPCRs).

The H1 receptor was the first member of the histamine receptor family to be pharmacologically defined, with the development of classical antihistamines (antagonists), such as diphenhydramine and fexofenadine. While antagonism of the H1 receptor of the immune system is commonly used for the treatment of allergic reactions, the H1 receptor is also expressed in various peripheral tissues and the central nervous system (CNS). In the brain, H1 is involved in the control of wakefulness, mood, appetite and hormone secretion.

The H2 receptor is also expressed in the CNS, where it may modulate several processes, including cognition. However, H2 receptor antagonists have primarily been developed to ameliorate gastric ulcers by inhibiting histamine-mediated gastric acid secretion by parietal cells. Classic H2 antagonists include cimetidine, ranitidine, and famotidine.

It should further be noted that H4 receptor function remains poorly defined, but may involve immune regulation and inflammatory processes.

On the other hand, H3 receptors have also been pharmacologically identified in the CNS, heart, lung, and stomach. The H3 receptor differs significantly from other histamine receptors, exhibiting low sequence homology (H1: 30%, H2: 28%, H4: 51%). H3 is a presynaptic autoreceptor on histamine neurons in the brain and a presynaptic heteroreceptor in non-histamine-containing neurons in both the central and peripheral nervous systems. In addition to histamine, H3 also modulates the release and/or synthesis of other neurotransmitters, including acetylcholine, dopamine, norepinepherin and serotonin. Of particular note, presynaptic modulation of histamine release by H3 allows significant regulation of H1 and H2 receptors in the brain. Modulating multiple neurotransmitter signaling pathways, H3 may contribute to varied physiological processes. Indeed, extensive preclinical evidence indicates that H3 plays a role in cognition, sleep-wake cycle and energy homeostasis.

Modulators of H3 function may be useful in the treatment of central nervous system disorders, such as cognitive impairment associated with schizophrenia (CIAS), dementia of Alzheimer Type (DAT), schizophrenia, Alzheimer's disease, attention-deficit hyperactivity disorder, Parkinson's disease, depression, and epilepsy, sleep disorders (narcolepsy and insomnia), cardiovascular disorders (acute myocardial infarction), respiratory disorders (asthma), obesity, and gastrointestinal disorders. See generally, Hancock. Biochem. Pharmacol. 2006 Apr. 14; 71(8): 1103-13 and Esbenshade et al. Mol Interv. 2006 April; 6(2):77-88, 59.

U.S. Pat. No. 7,223,788 discloses a series of compounds, including substituted bis-pyrrolidines, having melanin concentrating hormone (MCH) receptor antagonists. But the compounds disclosed therein are not reported to be active at the H3 receptor site.

Accordingly, one aspect of this invention is to provide a series of substituted phenyl cycloalkyl pyrrolidine (piperidine) spirolactams and amides as selective H3 receptor ligands for treatment of H3 receptor regulated CNS disorders.

It is another aspect of this invention to provide processes for the preparation of the substituted phenyl cycloalkyl pyrrolidine (piperidine) spirolactams and amides as disclosed herein.

Other aspects and further scope of the applicability of the present invention will become apparent from the detailed description that follows.

SUMMARY OF THE INVENTION

It has now been found that the compounds of formula (Ia) or (Ib) are useful as H3 receptor antagonists and/or inverse agonists. Thus in accordance with the practice of this invention there is provided a compound of formula (Ia):

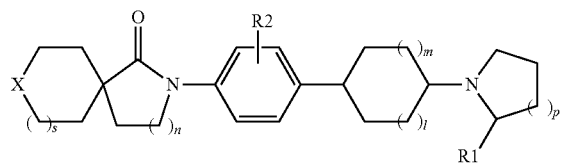

(Ia)

wherein:

l is 0 or 1;

m, n, p independently of each other are 0, 1 or 2;

s is 0 or 1;

X is O, $NR_5$ or $CHR_6$;

$R_1$ is hydrogen, $(C_1-C_4)$alkyl or $CF_3$;

$R_2$ is hydrogen, halogen, $(C_1-C_4)$alkyl, $(C_1-C_4)$alkoxy or $CF_3$;

$R_5$ is hydrogen, $(C_1-C_4)$alkyl or tert-butyloxycarbonyl (t-BOC); and $R_6$ is hydrogen, OH or COOR; and wherein R is hydrogen or $(C_1-C_4)$alkyl.

In another aspect of this aspect of this invention there is also provided a compound of formula (Ib):

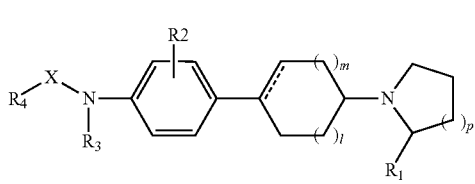

wherein:
l is 0 or 1;
m, and p independently of each other are 1 or 2;
Y is CO or SO$_2$;
---- is a single bond or a double bond;
R$_1$ is hydrogen, (C$_1$-C$_4$)alkyl or CF$_3$;
R$_2$ is hydrogen, halogen, (C$_1$-C$_4$)alkyl, (C$_1$-C$_4$)alkoxy or CF$_3$;
R$_3$ is hydrogen or (C$_1$-C$_4$)alkyl; and
R$_4$ is (C$_3$-C$_8$)cycloalkyl, substituted or unsubstituted heterocycle selected from piperidinyl, tetrahydropyranyl, substituted or unsubstituted heteroaryl selected from thienyl, furanyl, substituted or unsubstituted phenyl or benzyl; and wherein the substituents are selected from halogen, (C$_1$-C$_4$)alkyl, (C$_1$-C$_4$)alkoxy, CF$_3$, OCF$_3$ or CH$_3$CO.

This invention further includes various salts of the compounds of formulae (Ia) or (Ib) including various enantiomers or diastereomers of compounds of formula (Ia) or (Ib).

In other aspects of this invention there are also provided various pharmaceutical compositions comprising one or more compounds of formula (I) as well as their therapeutic use in alleviating various diseases which are mediated in-part and/or fully by H3 receptors.

DETAILED DESCRIPTION OF THE INVENTION

The terms as used herein have the following meanings:

As used herein, the expression "(C$_1$-C$_4$)alkyl" includes methyl and ethyl groups, and straight-chained or branched propyl, and butyl groups. Particular alkyl groups are methyl, ethyl, n-propyl, isopropyl and tert-butyl. Derived expressions such as "(C$_1$-C$_4$)alkoxy", "(C$_1$-C$_4$)alkoxy(C$_1$-C$_4$)alkyl", or "hydroxy(C$_1$-C$_4$)alkyl" are to be construed accordingly.

As used herein, the expression "(C$_1$-C$_8$)perfluoroalkyl" means that all of the hydrogen atoms in said alkyl group are replaced with fluorine atoms. Illustrative examples include trifluoromethyl and pentafluoroethyl, and straight-chained or branched heptafluoropropyl, nonafluorobutyl, undecafluoropentyl and tridecafluorohexyl groups. Derived expression, "(C$_1$-C$_8$)perfluoroalkoxy", is to be construed accordingly.

"Halogen" or "halo" means chloro, fluoro, bromo, and iodo.

As used herein, "patient" means a warm blooded animal, such as for example rat, mice, dogs, cats, guinea pigs, and primates such as humans.

As used herein, the expression "pharmaceutically acceptable carrier" means a non-toxic solvent, dispersant, excipient, adjuvant, or other material which is mixed with the compound of the present invention in order to permit the formation of a pharmaceutical composition, i.e., a dosage form capable of administration to the patient. One example of such a carrier is pharmaceutically acceptable oil typically used for parenteral administration.

The term "pharmaceutically acceptable salts" as used herein means that the salts of the compounds of the present invention can be used in medicinal preparations. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, hydrobromic acid, nitric acid, sulfamic acid, sulfuric acid, methanesulfonic acid, 2-hydroxyethanesulfonic acid, p-toluenesulfonic acid, fumaric acid, maleic acid, hydroxymaleic acid, malic acid, ascorbic acid, succinic acid, glutaric acid, acetic acid, propionic acid, salicylic acid, cinnamic acid, 2-phenoxybenzoic acid, hydroxybenzoic acid, phenylacetic acid, benzoic acid, oxalic acid, citric acid, tartaric acid, glycolic acid, lactic acid, pyruvic acid, malonic acid, carbonic acid or phosphoric acid. The acid metal salts such as sodium monohydrogen orthophosphate and potassium hydrogen sulfate can also be formed. Also, the salts so formed may present either as mono- or di-acid salts and can exist substantially anhydrous or can be hydrated. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts, and salts formed with suitable organic ligands, e.g. quaternary ammonium salts.

The expression "stereoisomers" is a general term used for all isomers of the individual molecules that differ only in the orientation of their atoms in space. Typically it includes mirror image isomers that are usually formed due to at least one asymmetric center, (enantiomers). Where the compounds according to the invention possess two or more asymmetric centers, they may additionally exist as diastereoisomers, also certain individual molecules may exist as geometric isomers (cis/trans). Similarly, certain compounds of this invention may exist in a mixture of two or more structurally distinct forms that are in rapid equilibrium, commonly known as tautomers. Representative examples of tautomers include keto-enol tautomers, phenol-keto tautomers, nitroso-oxime tautomers, imine-enamine tautomers, etc. It is to be understood that all such isomers and mixtures thereof in any proportion are encompassed within the scope of the present invention.

As used herein, 'R' and 'S' are used as commonly used terms in organic chemistry to denote specific configuration of a chiral center. The term 'R' (rectus) refers to that configuration of a chiral center with a clockwise relationship of group priorities (highest to second lowest) when viewed along the bond toward the lowest priority group. The term 'S' (sinister) refers to that configuration of a chiral center with a counter-clockwise relationship of group priorities (highest to second lowest) when viewed along the bond toward the lowest priority group. The priority of groups is based upon sequence rules wherein prioritization is first based on atomic number (in order of decreasing atomic number). A listing and discussion of priorities is contained in *Stereochemistry of Organic Compounds*, Ernest L. Eliel, Samuel H. Wilen and Lewis N. Mander, editors, Wiley-Interscience, John Wiley & Sons, Inc., New York, 1994.

In addition to the (R)-(S) system, the older D-L system may also be used herein to denote absolute configuration, especially with reference to amino acids. In this system a Fischer projection formula is oriented so that the number 1 carbon of the main chain is at the top. The prefix 'D' is used to represent the absolute configuration of the isomer in which the functional (determining) group is on the right side of the carbon at the chiral center and 'L', that of the isomer in which it is on the left.

In a broad sense, the term "substituted" is contemplated to include all permissible substituents of organic compounds. In a few of the specific embodiments as disclosed herein, the term "substituted" means substituted with one or more substituents independently selected from the group consisting of $(C_1-C_6)$alkyl, $(C_2-C_6)$alkenyl, $(C_1-C_6)$perfluoroalkyl, phenyl, hydroxy, —$CO_2H$, an ester, an amide, $(C_1-C_6)$alkoxy, $(C_1-C_6)$thioalkyl, $(C_1-C_6)$perfluoroalkoxy, —$NH_2$, Cl, Br, I, F, —NH-lower alkyl, and —N(lower alkyl)$_2$. However, any of the other suitable substituents known to one skilled in the art can also be used in these embodiments.

"Therapeutically effective amount" means an amount of the compound which is effective in treating the named disease, disorder or condition.

The term "treating" refers to:

(i) preventing a disease, disorder or condition from occurring in a patient that may be predisposed to the disease, disorder and/or condition, but has not yet been diagnosed as having it;

(ii) inhibiting the disease, disorder or condition, i.e., arresting its development; and (iii) relieving the disease, disorder or condition, i.e., causing regression of the disease, disorder and/or condition.

Thus, in accordance with the practice of this invention there is provided a compound of the formula (Ia):

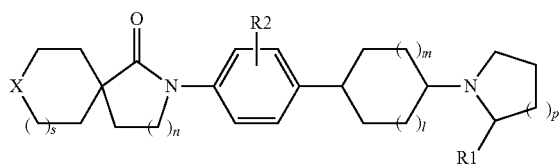

(Ia)

wherein:
l is 0 or 1;
m, n, p independently of each other are 0, 1 or 2;
s is 0 or 1;
X is O, $NR_5$ or $CHR_6$;
$R_1$ is hydrogen, $(C_1-C_4)$alkyl or $CF_3$;
$R_2$ is hydrogen, halogen, $(C_1-C_4)$alkyl, $(C_1-C_4)$alkoxy or $CF_3$;
$R_5$ is hydrogen, $(C_1-C_4)$alkyl or tert-butyloxycarbonyl (t-BOC); and
$R_6$ is hydrogen, OH or COOR; and wherein
R is hydrogen or $(C_1-C_4)$alkyl.

In another aspect of this aspect of this invention there is also provided a compound of formula (Ib):

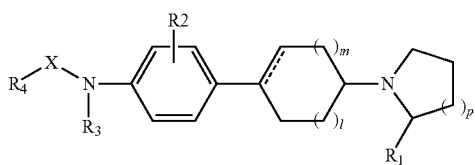

(Ib)

wherein:
l is 0 or 1;
m, and p independently of each other are 1 or 2;
Y is CO or $SO_2$;
---- is a single bond or a double bond;
$R_1$ is hydrogen, $(C_1-C_4)$alkyl or $CF_3$;
$R_2$ is hydrogen, halogen, $(C_1-C_4)$alkyl, $(C_1-C_4)$alkoxy or $CF_3$;
$R_3$ is hydrogen or $(C_1-C_4)$alkyl; and
$R_4$ is $(C_3-C_8)$cycloalkyl, substituted or unsubstituted heterocycle selected from piperidinyl, tetrahydropyranyl, substituted or unsubstituted heteroaryl selected from thienyl, furanyl, substituted or unsubstituted phenyl or benzyl; and wherein the substituents are selected from halogen, $(C_1-C_4)$alkyl, $(C_1-C_4)$alkoxy, $CF_3$, $OCF_3$ or $CH_3CO$.

This invention further includes various salts of the compounds of formulae (Ia) or (Ib) including various enantiomers or diastereomers of compounds of formulae (Ia) or (Ib). As noted hereinabove and by way of specific examples hereafter all of the salts that can be formed including pharmaceutically acceptable salts are part of this invention. As also noted hereinabove and hereafter all of the conceivable enantiomeric and diastereomeric forms of compounds of formula (I) are part of this invention.

In one of the embodiments, there is provided the compounds of formula (Ia) wherein
m is 1;
l and s independently of each other are 0 or 1;
p and n independently of each other are 0, 1 or 2;
X is O, $CH_2$, CHOH, $CH_3OCOCH$, NH or t-BOC-N;
$R_1$ is hydrogen or $CH_3$; and
$R_2$ is hydrogen or fluorine.

In another embodiment of this invention there is also provided a compound of formula (Ib), wherein
l is 0;
m and p are each 1;
Y is CO or $SO_2$;
---- is a single bond;
$R_1$ is $CH_3$;
$R_2$ and $R_3$ are hydrogen; and
$R_4$ is cyclopropyl, N-acetyl-piperidinyl, tetrahydropyranyl, thienyl, 3,5-dimethyl-isoxazol-4-yl, phenyl, 4-fluorophenyl, 3,4-difluorophenyl, 3-fluoro-5-methylphenyl, 4-chlorophenyl, 2-methylphenyl, 4-methylphenyl, 2-trifluoromethoxyphenyl, 4-trifluoromethoxyphenyl or benzyl.

In both of the above embodiments, the compounds may also include corresponding salts wherever possible including the pharmaceutically acceptable salts thereof.

In a further aspect of this invention the following compounds encompassed within the scope of compound of formula (Ia) of this invention without any limitation may be enumerated:

2-{4-[(S)-3-((S)-2-methyl-pyrrolidin-1-yl)-cyclopentyl]-phenyl}-8-oxa-2-aza-spiro[4.5]decan-1-one;

2-{4-[(S)-3-((S)-2-methyl-pyrrolidin-1-yl)-cyclopentyl]-phenyl}-2-aza-spiro[4.5]decan-1-one;

2-{4-[3-(2-methyl-pyrrolidin-1-yl)-cyclopentyl]-phenyl}-1-oxo-2,9-diaza-spiro[5.5]undecane-9-carboxylic acid tert-butyl ester;

8-hydroxy-2-{4-[3-(2-methyl-pyrrolidin-1-yl)-cyclopentyl]-phenyl}-2-aza-spiro[4.5]decan-1-one;

2-{4-[3-(2-methyl-pyrrolidin-1-yl)-cyclopentyl]-phenyl}-1-oxo-2-aza-spiro[4.5]decane-8-carboxylic acid methyl ester;

2-{4-[3-(2-methyl-pyrrolidin-1-yl)-cyclopentyl]-phenyl}-1-oxo-2,8-diaza-spiro[4.5]decane-8-carboxylic acid tert-butyl ester;
7-{4-[3-(2-methyl-pyrrolidin-1-yl)-cyclopentyl]-phenyl}-7-aza-spiro[4.5]decan-6-one;
2-{4-[3-(2-methyl-pyrrolidin-1-yl)-cyclopentyl]-phenyl}-2,9-diaza-spiro[5.5]undecan-1-one;
2-[4-(4-pyrrolidin-1-yl-cyclohexyl)-phenyl]-8-oxa-2-aza-spiro[4.5]decan-1-one;
2-{4-[4-((R)-2-methyl-pyrrolidin-1-yl)-cyclohexyl]-phenyl}-8-oxa-2-aza-spiro[4.5]decan-1-one;
2-{4-[4-((S)-2-methyl-piperidin-1-yl)-cyclohexyl]-phenyl}-8-oxa-2-aza-spiro[4.5]decan-1-one;
2-{4-[4-((S)-2-methyl-pyrrolidin-1-yl)-cyclohexyl]-phenyl}-8-oxa-2-aza-spiro[4.5]decan-1-one;
2-[2-fluoro-4-(4-pyrrolidin-1-yl-cyclohexyl)-phenyl]-1-oxo-2,8-diaza-spiro[4.5]decane-8-carboxylic acid tert-butyl ester;
2-{2-fluoro-4-[4-((R)-2-methyl-pyrrolidin-1-yl)-cyclohexyl]-phenyl}-1-oxo-2,8-diaza-spiro[4.5]decane-8-carboxylic acid tert-butyl ester;
2-[4-(4-azetidin-1-yl-cyclohexyl)-2-fluoro-phenyl]-1-oxo-2,8-diaza-spiro[4.5]decane-8-carboxylic acid tert-butyl ester;
2-{2-fluoro-4-[4-((S)-2-methyl-pyrrolidin-1-yl)-cyclohexyl]-phenyl}-1-oxo-2,8-diaza-spiro[4.5]decane-8-carboxylic acid tert-butyl ester;
2-{2-fluoro-4-[4-((S)-2-methyl-pyrrolidin-1-yl)-cyclohexyl]-phenyl}-2,8-diaza-spiro[4.5]decan-1-one hydrochloride;
2-{2-fluoro-4-[4-((R)-2-methyl-pyrrolidin-1-yl)-cyclohexyl]-phenyl}-2,8-diaza-spiro[4.5]decan-1-one hydrochloride;
2-[4-(4-azetidin-1-yl-cyclohexyl)-2-fluoro-phenyl]-2,8-diaza-spiro[4.5]decan-1-one; and
2-[2-fluoro-4-(4-pyrrolidin-1-yl-cyclohexyl)-phenyl]-2,8-diaza-spiro[4.5]decan-1-one.

In another aspect of this invention the following compounds encompassed within the scope of compound of formula (Ib) of this invention without any limitation may be enumerated:
{2-fluoro-4-[4-((S)-2-methyl-pyrrolidin-1-yl)-cyclohex-1-enyl]-phenyl}-carbamic acid benzyl ester;
1-acetyl-piperidine-4-carboxylic acid {4-[(S)-3-((S)-2-methyl-pyrrolidin-1-yl)-cyclopentyl]-phenyl}-amide;
thiophene-2-carboxylic acid {4-[(S)-3-((S)-2-methyl-pyrrolidin-1-yl)-cyclopentyl]-phenyl}-amide;
4-fluoro-N-{4-[(S)-3-((S)-2-methyl-pyrrolidin-1-yl)-cyclopentyl]-phenyl}-benzenesulfonamide;
5-fluoro-2-methyl-N-{4-[(S)-3-((S)-2-methyl-pyrrolidin-1-yl)-cyclopentyl]-phenyl}-benzamide;
3,5-dimethyl-isoxazole-4-carboxylic acid {4-[(S)-3-((S)-2-methyl-pyrrolidin-1-yl)-cyclopentyl]-phenyl}-amide;
cyclopropanesulfonic acid {4-[(S)-3-((S)-2-methyl-pyrrolidin-1-yl)-cyclopentyl]-phenyl}-amide;
tetrahydro-pyran-4-carboxylic acid {4-[(S)-3-((S)-2-methyl-pyrrolidin-1-yl)-cyclopentyl]-phenyl}-amide;
N-{4-[(S)-3-((S)-2-methyl-pyrrolidin-1-yl)-cyclopentyl]-phenyl}-benzamide;
3,4-difluoro-N-{4-[(S)-3-((S)-2-methyl-pyrrolidin-1-yl)-cyclopentyl]-phenyl}-benzenesulfonamide;
4-fluoro-N-{4-[(S)-3-((S)-2-methyl-pyrrolidin-1-yl)-cyclopentyl]-phenyl}-benzamide;
4-chloro-N-{4-[(S)-3-((S)-2-methyl-pyrrolidin-1-yl)-cyclopentyl]-phenyl}-benzamide;
2-methyl-N-{4-[(S)-3-((S)-2-methyl-pyrrolidin-1-yl)-cyclopentyl]-phenyl}-benzamide;
4-methyl-N-{4-[(S)-3-((S)-2-methyl-pyrrolidin-1-yl)-cyclopentyl]-phenyl}-benzamide;
N-{4-[(S)-3-((S)-2-methyl-pyrrolidin-1-yl)-cyclopentyl]-phenyl}-2-trifluoromethoxy-benzamide;
N-{4-[(S)-3-((S)-2-methyl-pyrrolidin-1-yl)-cyclopentyl]-phenyl}-4-trifluoromethoxy-benzamide; and
N-{4-[(S)-3-((S)-2-methyl-pyrrolidin-1-yl)-cyclopentyl]-phenyl}-2-phenyl-acetamide.

All of the above compounds may also include corresponding salts wherever possible including the pharmaceutically acceptable salts thereof. Specific salts of the compounds of this invention, without any limitation, are further enumerated hereinbelow by way of specific examples.

The compounds of this invention can be synthesized by any of the procedures known to one skilled in the art. Specifically, several of the starting materials used in the preparation of the compounds of this invention are known or are themselves commercially available. The compounds of this invention and several of the precursor compounds may also be prepared by methods used to prepare similar compounds as reported in the literature and as further described herein. For instance, see R. C. Larock, "Comprehensive Organic Transformations," VCH publishers, 1989.

It is also well known that in various organic reactions it may be necessary to protect reactive functional groups, such as for example, amino groups, to avoid their unwanted participation in the reactions. Conventional protecting groups may be used in accordance with standard practice and known to one of skilled in the art, for example, see T. W. Greene and P. G. M. Wuts in "Protective Groups in Organic Chemistry" John Wiley and Sons, Inc., 1991. For example, suitable amine protecting groups include without any limitation sulfonyl (e.g., tosyl), acyl (e.g., benzyloxycarbonyl or t-butoxycarbonyl) and arylalkyl (e.g., benzyl), which may be removed subsequently by hydrolysis or hydrogenation as appropriate. Other suitable amine protecting groups include trifluoroacetyl [—C(=O)CF$_3$] which may be removed by base catalyzed hydrolysis, or a solid phase resin bound benzyl group, such as a Merrifield resin bound 2,6-dimethoxybenzyl group (Ellman linker) or a 2,6-dimethoxy-4-[2-(polystyrylmethoxy)ethoxy]benzyl, which may be removed by acid catalyzed hydrolysis, for example with TFA.

More specifically, the compounds disclosed herein and various precursors used therefor can be synthesized according to the following procedures of Schemes 1-9, wherein $R_1$, $R_2$, $R_3$, $R_4$, $R_5$, $R_6$, X, Y, l, m, p, s and n are as defined for Formula (Ia) or (Ib) unless otherwise indicated.

Scheme 1 illustrates the preparation of intermediate compounds of formula (4). Commercially available carboxylic acid esters, such as methyl or ethyl esters, of formula (1) is treated with a suitable base, such as LDA in presence of HMPA in THF, followed by alkenyl halides of formula (2), to form the intermediate of formula (3). This reaction can be carried out using any of the procedures known to one skilled in the art, such as reported in the literature or any suitable modifications thereof. (Generally, see for example, Nagumo, S.; Matoba A.; et al, *Tetrahedron*, 2002, 58(49), 9871-9877; Stafford, J. A.; Heathcock, C. H. *J. Org. Chem.*, 1990, 55(20), 5433-5434).

Scheme 1

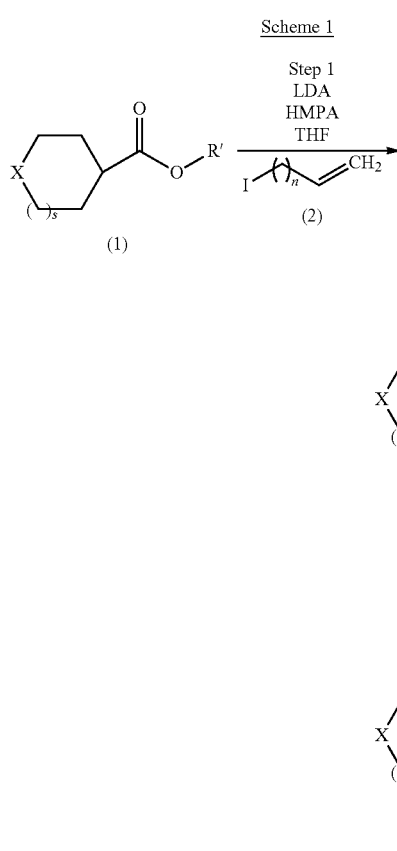

s = 0, 1; n = 1, 2, R' = methyl or ethyl.

In step 2, Scheme 1, the alkene of formula (3) is suitably oxidized using any of the procedures known to one skilled in the art to form the aldehyde of formula (4). For instance such cleavage reactions can be carried out using $OsO_4$ and $NaIO_4$ in propanol and water to form aldehyde of formula (4). Such a reaction can also be carried out by using ozonolysis which is known in the literature. Similarly, various other oxidative methods to cleave an olefinic bond to form an aldehyde can be employed to prepare intermediates of formula (4).

Scheme 2 illustrates the preparation of an intermediate of formula (10) wherein m is as defined herein. Accordingly, in step 1, Scheme 2, the boronic acid of formula (6) is condensed with a cyclic enone of formula (5), such as cyclo-pentenone or cyclohexenone by the reaction conditions known to one skilled in the art. For example, various such procedures reported in the literature can be enumerated (See for example, *J. Org. Chem.*, 2003, 9481-9484 and *J. Am. Chem. Soc.* 1998, 5579-5580).

Scheme 2

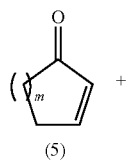

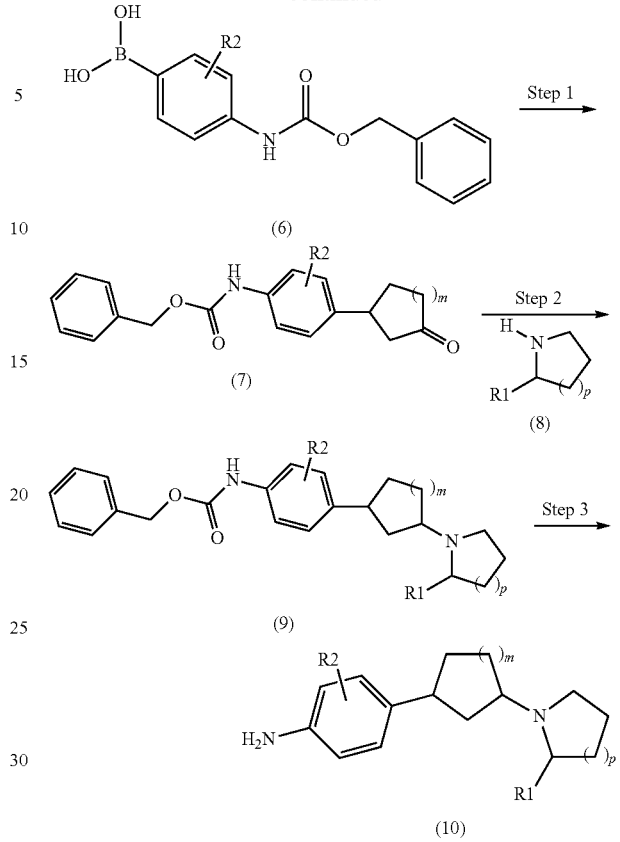

In Step 2, Scheme 2, the ketone of formula (7) can be easily condensed with commercially available amine of formula (8) to obtain the intermediate of formula (9). Such a reaction is carried out under typical reductive amination reaction conditions. For instance, such condensation reactions are generally carried out in the presence of reducing agents such as triacetoxyborohydride catalyzed by an acid, such as hydrochloric acid or acetic acid or trifluoroacetic acid, in an inert atmosphere, such as nitrogen atmosphere. The reaction can be carried out either at sub-ambient, ambient or super-ambient reaction temperatures and pressures. Typically, such reactions are carried out at room temperature under atmospheric pressure of nitrogen. The reaction mixture is then worked-up using procedures known to one skilled in the art to isolate the intermediate of formula (9). In Step 3, Scheme 2, the intermediate of formula (9) is subjected de-protection conditions, such as hydrogenation, to obtain the intermediate of formula (10).

Scheme 3 illustrates the synthesis of an intermediate of formula (14), wherein m is as defined herein. In Step 1, Scheme 3, the ketone of formula (7) is reduced using any of the reducing agents that can bring about such a reduction. For example, reducing agents such as $NaBH_4$, DIBAL-H, or alike, can be used to form an alcohol of formula (11).

In Step 2, Scheme 3, the alcohol of formula (11) is then treated with suitable groups to form a good leaving group, such as for example, methanesulfonyl chloride (or p-toluene sulfonyl chloride) to form the intermediate mesylate of formula (12). This reaction can be carried out using any of the procedures known to one skilled in the art, such as for example carrying out the reaction in the presence of a suitable base such as triethylamine and DMAP in a suitable organic solvent, preferably an aprotic solvent such as dichloromethane at sub-ambient to ambient temperature conditions.

In Step 3, Scheme 3, the intermediate of formula (12) is condensed with a desired pyrrolidine or piperidine of formula (8). Again, such condensation reactions can be carried out using any of the procedures known to one skilled in the art in order to obtain the intermediate of formula (13). Typically, such condensation reactions are carried out in the presence of a base such as potassium carbonate in the presence of solvents such as acetonitrile at ambient to super-ambient temperature conditions.

Finally, in Step 4, Scheme 3, the intermediate of formula (13) is then subjected to the de-protection conditions, such as hydrogenation, to give an Intermediate of formula (14). Again, such deprotection reactions can be carried out using any of the other known reaction conditions, such as for example treating under suitable acid agents.

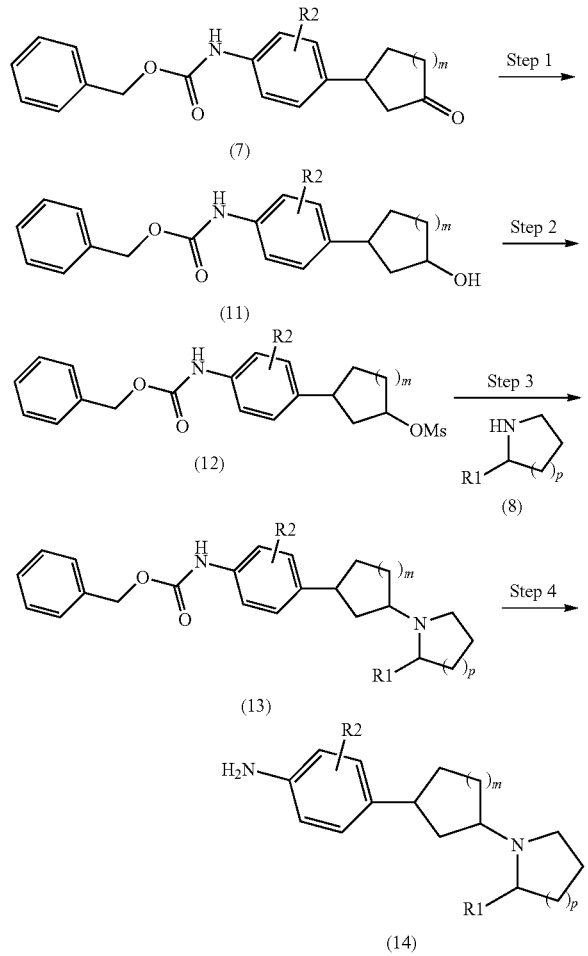

Scheme 4 illustrates the preparation of some of the compounds of formula (Ia), wherein m, and l are as defined herein.

In step 1, Scheme 4, the aldehyde of formula (4) is condensed with a desired intermediate of formula (14) by any of the known reductive amination procedures to form an intermediate of formula (15). For instance, such condensation reactions are generally carried out in the presence of reducing agents such as triacetoxyborohydride catalyzed by an acid, such as hydrochloric acid or acetic acid or trifluoroacetic acid, in an inert atmosphere, such as nitrogen atmosphere. The reaction can be carried out either at sub-ambient, ambient or super-ambient reaction temperatures and pressures. Typically, such reactions are carried out at room temperature under atmospheric pressure of nitrogen. The reaction mixture is then worked-up using procedures known to one skilled in the art to isolate the intermediate of formula (15). In step 2, Scheme 4, the cyclization is either carried out simultaneously in the same reaction vessel during condensation reaction in Step 1, Scheme 4 or is initiated by catalytic amount of base, such as potassium t-butoxide in aprotic solvents, such as THF, to form compound of formula (Ia).

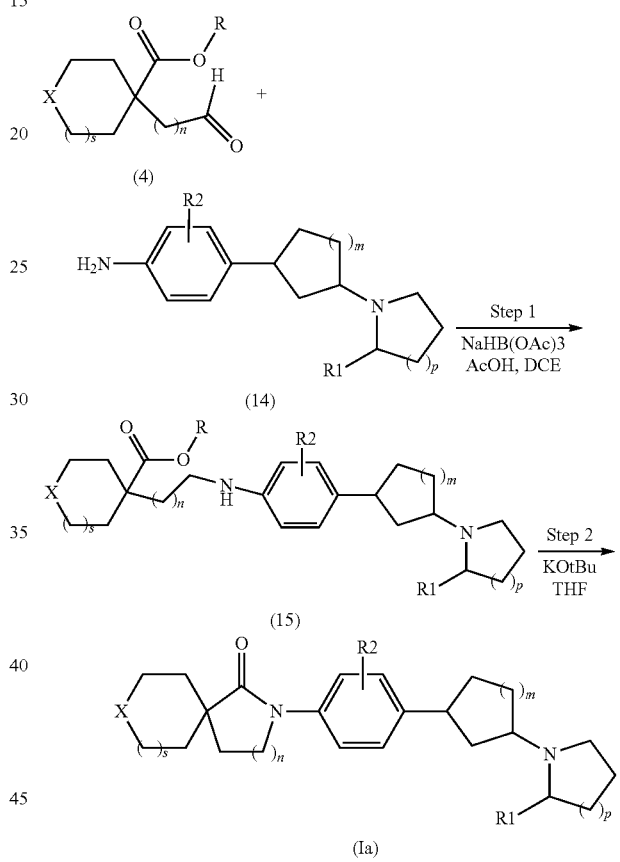

Scheme 5 illustrates the process for preparation of the intermediate of formula (23), where m and l are as defined herein. In Step 1, Scheme 5, the ketone of formula (16) is treated with a base, such as LDA at lower temperature, typically at around −78° C. to form an enolate of formula (18). The enolate (18) can suitably be trapped by a suitable counter ion such as for example the enolate (18) is trapped with triflate transferring reagent, typically using N-phenyl triflimide or N-(5-chloro-2-pyridyl)triflimide (17) to form an enolate triflate of formula (18) using conditions well known to one skilled in the art. For example, such reaction procedures are reported in the literature, see generally, D. L. Comins, A. Dehghani, *Tetrahedron Lett.,* 1992, 33, 6299-6302.

In Step 2, Scheme 5, the intermediate of formula (18) is coupled with a boronic acid of formula (19) using any of the known coupling methods. The coupling reaction conditions can also be modified in accordance with the starting materials used from the literature procedures in order to obtain the intermediate of formula (20). (see for example, H. N.

Nguyen, X. Huang, S. Buchwald, *J. Am. Chem. Soc*, 2003, 125, 11818-11819; D. J. Denhart, et al, *Bioorg. Med. Chem. Lett.*, 2009, 4031-4033; J. B. Evarts Jr., P. L. Fuchs, *Tetrahedron Lett.*, 2001, 42, 3673)

In Step 3, Scheme 5, the protection group on the intermediate of formula (20) is removed using any of the literature procedures. For instance, such deprotection can be achieved by reacting intermediate of formula (20) with TBAF or other fluoride reagents at ambient to super ambient temperature to get an intermediate alcohol of formula (21).

In Step 4, Scheme 5, the alcohol of formula (21) is treated with p-toluene sulfonyl chloride or methanesulfonyl chloride to form the intermediate of formula (22). This reaction can be carried out using any of the procedures known to one skilled in the art, such as, for example, carrying out the reaction in the presence of a suitable base such as triethylamine and DMAP in a suitable organic solvent, preferably an aprotic solvent such as dichloromethane at sub-ambient to ambient temperature conditions. The intermediate of formula (22) is then condensed with commercially available desired amine of for-

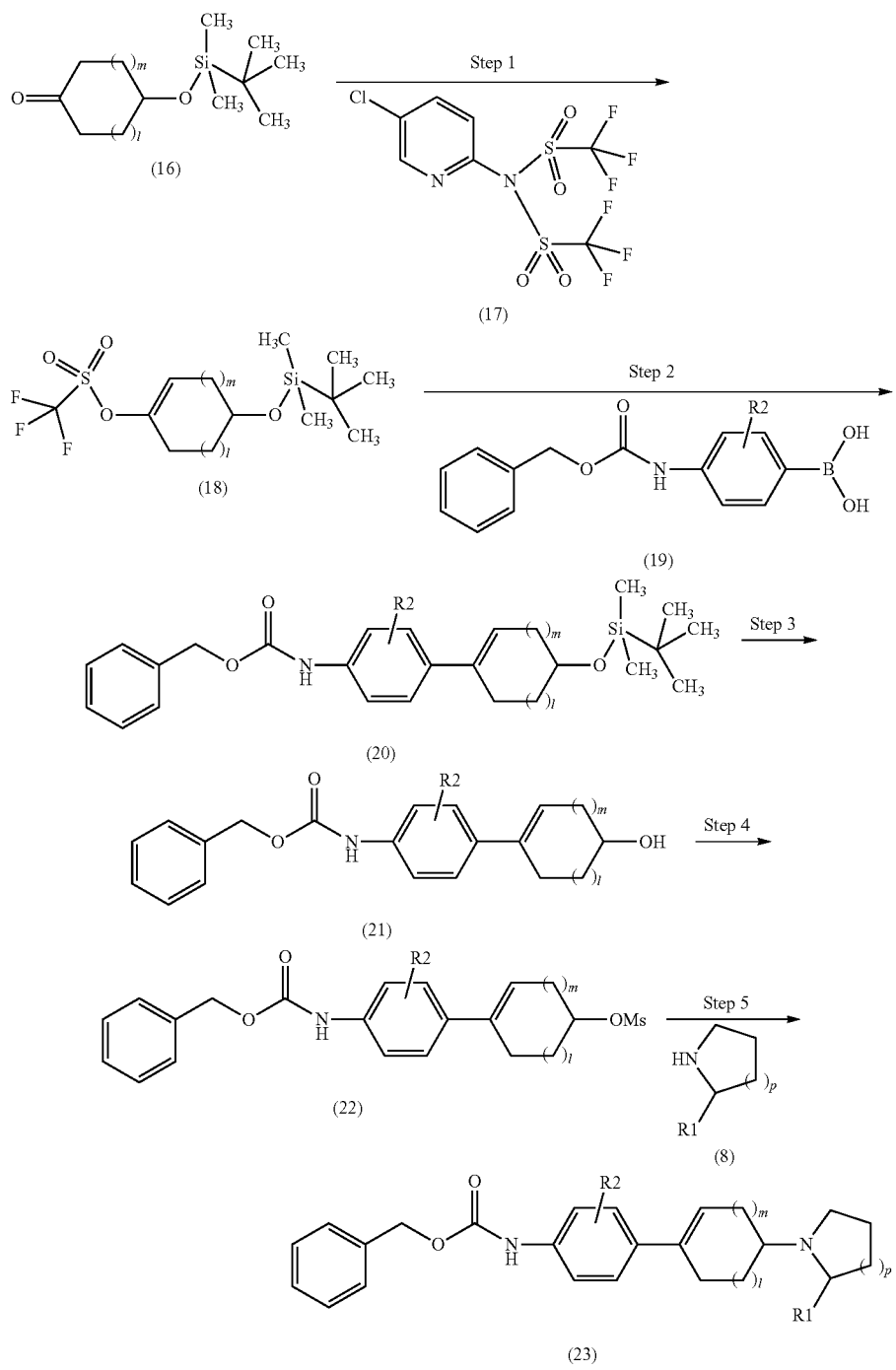

mula (8). Again, such condensation reactions can be carried out using any of the procedures known to one skilled in the art in order to obtain the intermediate of formula (23). Typically, such condensation reactions are carried out in the presence of a base such as potassium carbonate in the presence of solvents such as acetonitrile at ambient to super-ambient temperature conditions.

Scheme 6 illustrates the preparation of the intermediate of formula (24). The intermediate of formula (20) is subjected to any of the known deprotection procedures to obtain the debenzylated intermediate of formula (24). Typically, such debenzylation is carried out under hydrogenation reaction conditions. The hydrogenation conditions would not only remove the benzyl protection group but at the same time reduces the double bond to give the intermediate of formula (24). Such a hydrogenation reaction is carried out under hydrogen atmosphere at ambient temperature catalyzed by Pd—C (10%) in methanol or ethanol with or without co-solvent, such as ethyl acetate.

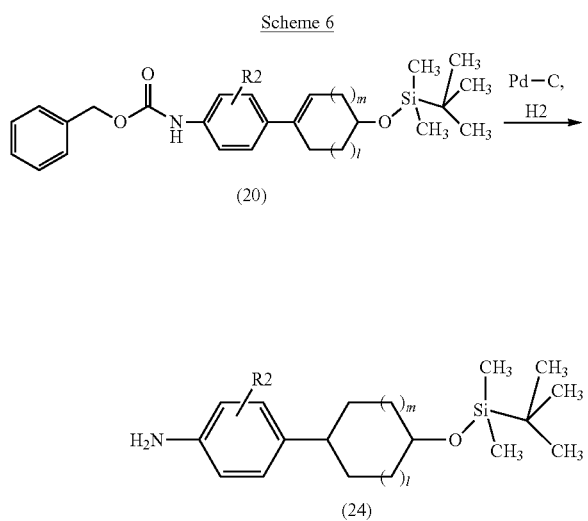

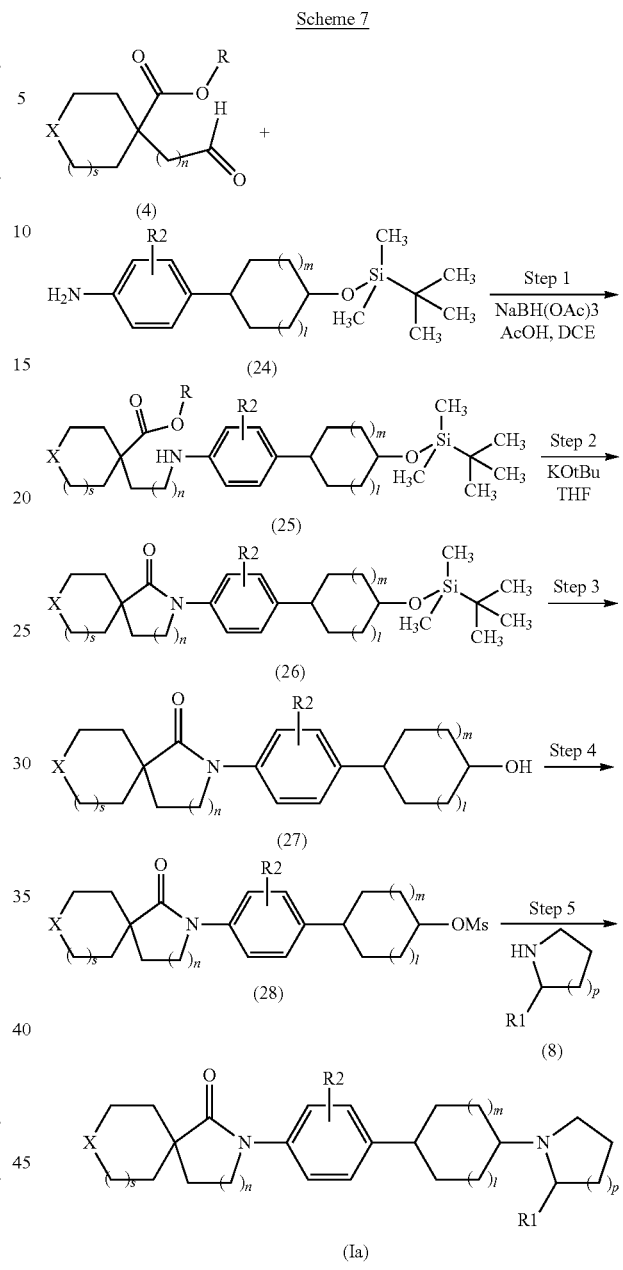

Scheme 7 illustrates another method for the preparation of some of the compounds of the formula (Ia), wherein m and l are as defined herein. In step 1, Scheme 7, the aldehyde of formula (4) is condensed with a desired intermediate of formula (24) by any of the known reductive amination procedures to form an intermediate of formula (25). For instance, such condensation reactions are generally carried out in the presence of reducing agents such as triacetoxyborohydride catalyzed by an acid, such as hydrochloric acid or acetic acid or trifluoroacetic acid, in an inert atmosphere, such as nitrogen atmosphere. The reaction can be carried out either at sub-ambient, ambient or super-ambient reaction temperatures and pressures. Typically, such reactions are carried out at room temperature under atmospheric pressure of nitrogen. The reaction mixture is then worked-up using procedures known to one skilled in the art to isolate the intermediate of formula (25). The cyclization either occurs simultaneously during Step 1, Scheme 7, or is initiated by catalytic amounts of a base, such as potassium t-butoxide in aprotic solvents, such as THF, to form the intermediate of formula (26).

In Step 3, Scheme 7, the intermediate of formula (26) is then treated with fluoride reagents, typically TBAF in THF at ambient to super-ambient temperatures to form an alcohol of formula (27).

In Step 4, Scheme 7, alcohol of formula (27) is treated with methanesulfonyl chloride or p-toluene sulfonyl chloride to form the intermediate of formula (28). This reaction can be carried out using any of the procedures known to one skilled in the art, such as, for example, carrying out the reaction in the presence of a suitable base such as triethylamine and DMAP in a suitable organic solvent, preferably an aprotic solvent such as dichloromethane at sub-ambient to ambient temperature conditions, typically at 0° C. for 30 min.

In Step 5, Scheme 7, the intermediate of formula (28) is condensed with a desired pyrrolidine or piperidine, or azetidine of formula (8). Again, such condensation reactions can be carried out using any of the procedures known to one skilled in the art in order to obtain the compound of formula (Ia). Typically, such condensation reactions are carried out in the presence of a base such as potassium carbonate in the presence of solvents such as acetonitrile at ambient to super-ambient temperature conditions.

Scheme 8 illustrates the preparation of compounds of formula (Ib) of this invention wherein ---- is a single bond using either Method A or Method B depending upon the availability of desired carboxylic acid of formula (29) either in the form of acid itself or its acid chloride.

In Method A, Scheme 8, the acid chloride of formula (29) can be reacted with the intermediate (14) using any of the conditions known to one skilled in the art. Typically, such conditions include without any limitations reaction of the acid chloride with the intermediate of formula (14) in a suitable organic solvent such as for example dichloromethane in the presence of a suitable base such as pyridine. Such reactions are generally carried out at sub-ambient temperature conditions, for example around 0° C., however ambient to super-ambient temperature conditions may also be suitable in certain situations depending upon the nature of the acid chloride and the intermediate (14).

Similarly, in Method B, Scheme 8, the carboxylic acid of formula (29) can be reacted with the intermediate of formula (14) under various reaction conditions known to one skilled in the art. For instance, the acid of formula (29) is reacted with intermediate of formula (14) at sub-ambient temperature conditions in the presence of suitable reagents such as for example a mixture of N-methylmorpholine, 1-hydroxybenzotriazole and EDC HCl, or other suitable peptide coupling reagents, such as TPTU, HOBt in the presence of iPr2NEt, in DCM and/or DMF.

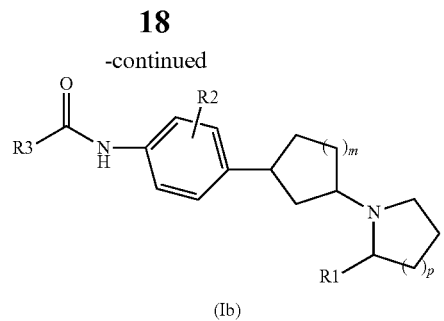

(Ib)

Z = Cl, OH

Scheme 9 illustrates the preparation of compounds of formula (Ib) of this invention wherein ---- is either a single bond or a double bond. In Step 1a, Scheme 9, the intermediate of formula (23) can be subjected to the hydrogenation conditions. Typically, such conditions include using Pd—C (10%) as catalyst, in a proper solvent, such as methanol or ethanol with or without using the co-solvent, such as EtOAc, DCM, at ambient temperature and hydrogen atmosphere. As already noted above, under such hydrogenation conditions it is possible to remove simultaneously the benzyl protection group as well as reduce the double bond to obtain the intermediate of formula (30).

On the other hand, in Step 1b, Scheme 9, the intermediate of formula (23) can also be treated with suitable reagents, such as for example, iodotrimethylsilane in acetonitrile to selectively remove the benzyl group using the reaction conditions which are well known to one skilled in the art to obtain the intermediate of formula (31) (see R. S. Lott, et al. *J. Chem. Soc., Chem. Commun.*, 1979, 495).

The intermediates of formulae (30) or (31) can then be converted into corresponding amides of formula (Ib) wherein ---- is either a single bond or a double bond using either Method A or Method B in the Step 2, Scheme 9 using the procedures described in Scheme 8 or by any of the other methods known in the art.

Scheme 8

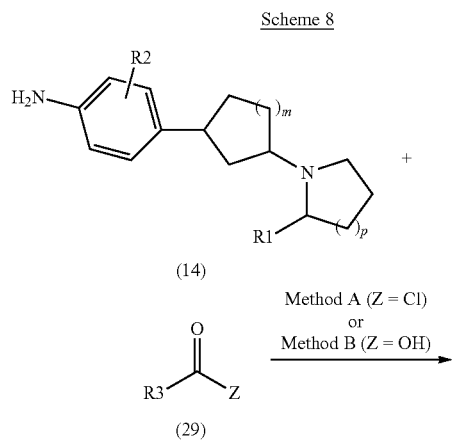

Scheme 9

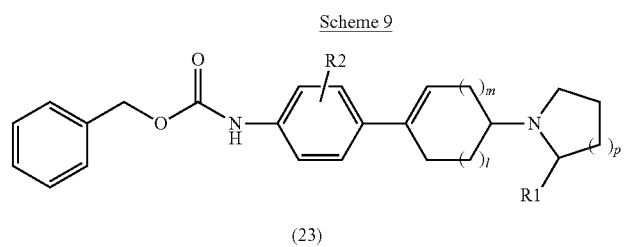

-continued

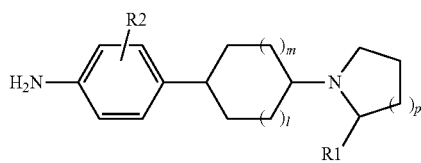

(30)

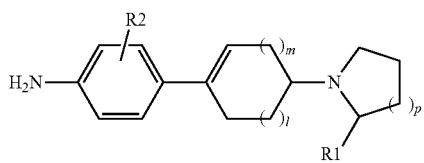

(31)

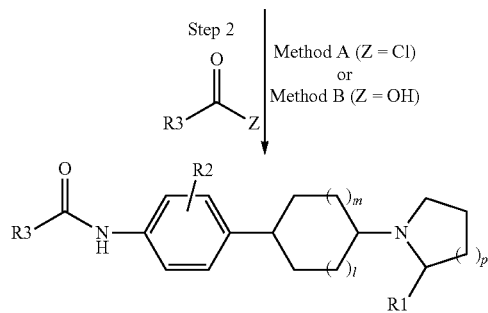

(Ib)

Z = Cl, OH.

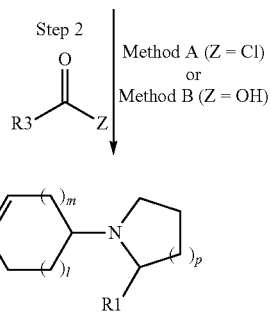

(Ic)

As already noted hereinabove, the compounds of this invention can readily be converted into salts. More particularly, the compounds of the present invention are basic, and as such compounds of this invention are useful in the form of a free base or in the form of a pharmaceutically acceptable acid addition salt thereof. Acid addition salts may be a more convenient form for use; and, in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial inhibitory effects inherent in the free base are not vitiated by side effects ascribable to the anions. Although pharmaceutically acceptable salts of said basic compound is preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures.

In another aspect of this embodiment, a specific disease, a disorder or a condition that can be prevented and/or treated with the compound of this invention include, without any limitation the following: sleep-related disorders (specific examples include without any limitation narcolepsy, attentional deficits, circadian rhythm sleep disorders, obstructive sleep apnea, periodic limb movement and restless leg syndrome, excessive sleepiness and drowsiness due to medication side-effect, etc.), neurological disorders (specific examples that may be enumerated include but not limited to dementia, Alzheimer's disease, multiple sclerosis, epilepsy and neuropathic pain), neuropsychological and cognitive disorders (a few of the specific examples include without any limitation include schizophrenia, attention deficit/hyperactivity disorder, Alzheimer's disease, depression, seasonal affective disorder, and cognitive impairment). Certain of the disorders also include cognitive impairment associated with schizophrenia (CIAS), anxiety disorders such as generalized anxiety, panic disorder and post-traumatic stress disorder, and major depressive disorder. Other disorders include dementia of Alzheimer type (DAT), cognitive deficits related to neurological diseases such as Alzheimer, Parkinson, Huntington, age related cognitive impairment, mild cognitive impairment, vascular dementia, Lewis Body dementia and any other cognition associated to cognitive deficits.

As described hereinbelow by way of specific examples, the compounds of formula (I) bind to the H3 receptors and demonstrate inverse agonism versus H3 functional activity. Therefore, the compounds of this invention may have utility in the treatment of diseases or conditions ameliorated with H3 receptor ligands. More specifically, the compounds of the present invention are H3 receptor ligands that modulate function of the H3 receptor by antagonizing the activity of the receptor. Further, the compounds of this invention may be inverse agonists that inhibit the basal activity of the receptor or they may be antagonists that completely block the action of receptor-activating agonists. Additionally, the compounds of this invention may also be partial agonists that partially block or partially activate the H3 receptor or they may be agonists that activate the receptor. Thus the compounds of this invention may act differentially as antagonists, inverse agonists and/or partial agonists depending on functional output, histamine tone and or tissue context. Accordingly, the differential activities of these compounds may allow for utility to ameliorate multiple disease states as specifically enumerated above.

Thus in one aspect of this invention there is provided a method of treating a disease in a patient, said disease selected from the group consisting of sleep related disorder, dementia, Alzheimer's disease, multiple sclerosis, cognitive disorder, attention deficit hyperactivity disorder and depression, comprising administering to said patient a therapeutically effective amount of a compound of formulae (Ia) or (Ib).

One of skill in the art readily appreciates that the pathologies and disease states expressly stated herein are not intended to be limiting rather to illustrate the efficacy of the compounds of the present invention. Thus it is to be understood that the compounds of this invention may be used to treat any disease caused by the effects of H3 receptors. That is, as noted above, the compounds of the present invention are modulators of H3 receptors and may be effectively administered to ameliorate any disease state which is mediated all or in part by H3 receptors.

All of the various embodiments of the compounds of this invention as disclosed herein can be used in the method of treating various disease states as described herein. As stated herein, the compounds used in the method of this invention are capable of inhibiting the effects of H3 receptor and thereby alleviating the effects and/or conditions caused due to the activity of H3.

In another embodiment of the method of this invention, the compounds of this invention can be administered by any of the methods known in the art. Specifically, the compounds of this invention can be administered by oral, intramuscular, subcutaneous, rectal, intratracheal, intranasal, intraperitoneal or topical route.

In another embodiment of this invention the compounds of formulae (Ia) or (Ib) of this invention or a pharmaceutically acceptable salt, an enantiomer, or a diastereomer thereof can be used to prepare medicaments and/or pharmaceutical compositions which can be used to inhibiting and/or modulating the effects of H3 receptor and thereby alleviating the effects and/or diseases and/or conditions caused due to the activity of H3. Specific diseases and/or conditions are those which are specifically enumerated as herein. Accordingly, the medicaments produced from the compounds of formulae (Ia) or (Ib) of this invention can be used to treat a patient suffering from any of the diseases that are believed to be caused due to the aforementioned effects of H3 receptors. Even more specifically, the compounds of formulae (Ia) or (Ib) of this invention can be used to treat various disease states as enumerated herein.

Finally, in yet another embodiment of this invention, there is also provided a pharmaceutical composition comprising a pharmaceutically acceptable carrier and a compound of formula (I), including enantiomers, stereoisomers, and tautomers of said compound and pharmaceutically acceptable salts, solvates or derivatives thereof, with said compound having the general structure shown in formula I as described herein.

As described herein, the pharmaceutical compositions of this invention feature H3 inhibitory activity and thus are useful in treating any disease, condition or a disorder caused due to the effects of H3 in a patient. Again, as described above, all of the preferred embodiments of the compounds of this invention as disclosed herein can be used in preparing the pharmaceutical compositions as described herein.

Preferably the pharmaceutical compositions of this invention are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. An erodible polymer containing the active ingredient may be envisaged. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Flavored unit dosage forms contain from 1 to 100 mg, for example 1, 2, 5, 10, 25, 50, 60, 70, 80, 90 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

The pharmaceutical compositions of this invention can be administered by any of the methods known in the art. In general, the pharmaceutical compositions of this invention can be administered by oral, intramuscular, subcutaneous, rectal, intratracheal, intranasal, intraperitoneal or topical route. The preferred administrations of the pharmaceutical composition of this invention are by oral and intranasal routes. Any of the known methods to administer pharmaceutical compositions by an oral or an intranasal route can be used to administer the composition of this invention.

In the treatment of various disease states as described herein, a suitable dosage level is about 0.01 to 250 mg/kg per day, preferably about 0.05 to 100 mg/kg per day, and especially about 0.05 to 20 mg/kg per day. The compounds may be administered on a regimen of 1 to 4 times per day.

This invention is further illustrated by the following examples which are provided for illustration purposes and in no way limit the scope of the present invention.

EXAMPLES

General

As used in the examples and preparations that follow, the terms used therein shall have the meanings indicated: "kg" refers to kilograms, "g" refers to grams, "mg" refers to milligrams, "μg" refers to micrograms, "mol" refers to moles, "mmol" refers to millimoles, "μmole" refers to micromoles, "nmole" refers to nanomoles, "L" refers to liters, "mL" or "ml" refers to milliliters, "μL" refers to microliters, "gal"

refers to gallons, "° C." refers to degrees Celsius, "$R_f$" refers to retention factor, "mp" or "m.p." refers to melting point, "dec" refers to decomposition, "bp" or "b.p." refers to boiling point, "mm of Hg" refers to pressure in millimeters of mercury, "cm" refers to centimeters, "nm" refers to nanometers, "abs." refers to absolute, "conc." refers to concentrated, "c" refers to concentration in g/mL, "DMSO" refers to dimethyl sulfoxide, "DMF" refers to N,N-dimethylformamide, "CU" refers to 1,1'-carbonyldiimidazole, "DCM" or "$CH_2Cl_2$" refers to dichloromethane, "DCE" refers to 1,2-dichloroethane, "HCl" refers to hydrochloric acid, "EtOAc" refers to ethyl acetate, "PBS" refers to Phosphate Buffered Saline, "PEG" refers to polyethylene glycol, "MeOH" refers to methanol, "$MeNH_2$" refers to methyl amine, "$N_2$" refers to nitrogen gas, "iPrOH" refers to isopropyl alcohol, "$Et_2O$" refers to ethyl ether, "LAH" refers to lithium aluminum hydride, "heptane" refers to n-heptane, "$PdCl_2(dppf)_2$" refers to 1,1'-bis(diphenylphosphino)ferrocene-palladium (II) dichloride DCM complex, "HBTU" refers to 2-(1H-benzotriazol-1-yl)-1,1,3,3-tetramethyluronium hexafluorophosphate, "CAS xxx-xx-x" refers to Chemical Abstract Service registration number; "BINAP" refers to 2,2'-bis(diphenylphosphino)-1,1'-binaphthyl; "LDA" refers to lithium diisopropylamide; "DABCO" refers to 1,4-diazabicyclo[2.2.2]octane; "$NaBH(OAc)_3$" refers to sodium triacetoxyborohydride; "DCE" refers to 1,2-dichloroethane; "DIBAL or DIBAL-H" refers to diisobutylaluminium hydride; "DIEA" refers to N,N-diisopropylethylamine; "DMAP" refers to 4-dimethylaminopyridine; "eq. or equiv." refers to equivalent; "$Et_3N$" refers to triethylamine; "HOBT or HOBt" refers to 1-hydroxybenzotriazole; "EDC" refers to ethyl-(3-dimethylamino-propyl)-carbodiimide; "TPTU" refers to [dimethylamino-(2-oxo-2H-pyridin-1-yloxy)-methylene]-dimethyl-ammonium tetrafluoro borate; "HATU" refers to 2-(1H-7-azabenzotriazol-1-yl)-1,1,3,3-tetramethyl uronium hexafluorophosphate methanaminium; "HMPA" refers to hexamethylphosphoramide; "HOAc" refers to acetic acid; "$Pd_2(dba)_3$" refers to tris(dibenzylideneacetone)dipalladium; "$Pd(PPh_3)_4$" refers tetrakis(triphenylphosphine)palladium (0); "SM" refers to starting material; "TBAF" refers to tetrabutylammonium fluoride; "CsF" refers to cesium fluoride, "MeI" refers to methyl iodide, "AcN," "MeCN" or "$CH_3CN$" refers to acetonitrile, "TFA" refers to trifluoroacetic acid, "THF" refers to tetrahydrofuran, "NMP" refers to 1-methyl-2-pyrrolidinone, "$H_2O$" refers to water, "BOC" refers to t-butyloxycarbonyl, "brine" refers to a saturated aqueous sodium chloride solution, "M" refers to molar, "mM" refers to millimolar, "µM" refers to micromolar, "nM" refers to nanomolar, "N" refers to normal, "TLC" refers to thin layer chromatography, "HPLC" refers to high performance liquid chromatography, "HRMS" refers to high resolution mass spectrum, "µCi" refers to microcuries, "i.p." refers to intraperitoneally, "i.v." refers to intravenously, anhyd=anhydrous; aq=aqueous; min=minute; hr=hour; d=day; sat.=saturated; s=singlet, d=doublet; t=triplet; q=quartet; m=multiplet; dd=doublet of doublets; br=broad; LC=liquid chromatograph; MS=mass spectrograph; ESI/MS=electrospray ionization/mass spectrograph; RT=retention time; M=molecular ion, "~"=approximately.

Reactions generally are run under a nitrogen atmosphere. Solvents are dried over magnesium sulfate and are evaporated under vacuum on a rotary evaporator. TLC analyses are performed with EM Science silica gel 60 F254 plates with visualization by UV irradiation. Flash chromatography is performed using Alltech prepacked silica gel cartridges. The $^1H$ NMR spectra are run at 300 MHz on a Gemini 300 or Varian Mercury 300 spectrometer with an ASW 5 mm probe, and usually recorded at ambient temperature in a deuterated solvent, such as $D_2O$, DMSO-$D_6$ or $CDCl_3$ unless otherwise noted. Chemical shifts values (δ) are indicated in parts per million (ppm) with reference to tetramethylsilane (TMS) as the internal standard.

High Pressure Liquid Chromatography-Mass Spectrometry (LCMS) experiments to determine retention times ($R_T$) and associated mass ions are performed using one of the following methods:

Mass Spectra (MS) are recorded using a Micromass mass spectrometer. Generally, the method used was positive electro-spray ionization, scanning mass m/z from 100 to 1000. Liquid chromatography was performed on a Hewlett Packard 1100 Series Binary Pump & Degasser; Auxiliary detectors used were: Hewlett Packard 1100 Series UV detector, wavelength=220 nm and Sedere SEDEX 75 Evaporative Light Scattering (ELS) detector temperature=46° C., $N_2$ pressure=4 bar.

LCT: Grad (AcN+0.05% TFA):($H_2O$+0.05% TFA)=5:95 (0 min) to 95:5 (2.5 min) to 95:5 (3 min). Column: YMC Jsphere 33×2 4 µM, 1 ml/min MUX: Column: YMC Jsphere 33×2, 1 ml/min Grad (AcN+0.05% TFA):(H2O+0.05% TFA)=5:95 (0 min) to 95:5 (3.4 min) to 95:5 (4.4 min).

LCT2: YMC Jsphere 33×2 4 µM, (AcN+0.05% TFA):(H2O+0.05% TFA)=5:95 (0 min) to 95:5 (3.4 min) to 95:5 (4.4 min)

QU: YMC Jsphere 33×2 1 ml/min, (AcN+0.08% formic acid):(H20+0.1% formic acid)=5:95 (0 min) to 95:5 (2.5 min) to 95:5 (3.0 min)

The following examples describe the procedures used for the preparation of various starting materials employed in the preparation of the compounds of this invention.

Intermediates

Intermediate (1)

4-(2-Oxo-ethyl)tetrahydro-pyran-4-carboxylic acid methyl ester

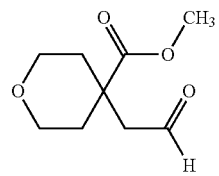

Step 1: 4-Allyl-tetrahydro-pyran-4-carboxylic acid methyl ester

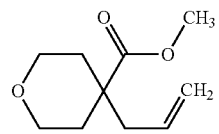

In a 250 mL round bottom flask was weighed 6.1 g (60 mmol) of diisopropylamine and dissolved in THF (100 mL).

This solution was cooled to −78° C. To this solution was added 37.5 mL of 1.6 M butyllithium in hexane, stirred for 15 min, warmed up to 0° C. for 20 min, re-cooled to −78° C.

To this mixture was added tetrahydro-pyran-4-carboxylic acid methyl ester (7.2 g, 50 mmol) in THF (10 mL). There was almost no color change (light a little bit). This was stirred at −78° C. using dry ice/acetone bath for 45 min. Then, a mixture of 5 g of HMPA and 10.92 g of allyl iodide was added via canula. At the end of about 90% addition of this mixture, white precipitate formed suddenly. This mixture was stirred at −78° C. for 20 min, then the dry ice/acetone bath was removed and the stirring was continued to allow the reaction mixture to warm to r.t. over 30 min. At which time the precipitate dissolved, the reaction mixture was poured into ice-water (100 mL) and ether (50 mL). The two layers were separated, and the aqueous layer was extracted with ether (3×50 mL). The combined organic layers were washed with brine, dried ($K_2CO_3$), filtered, and concentrated in vacuo to obtain 8.75 g (95% yield) of the title compound as a yellow liquid.

LC/MS: $R_T$=2.70 min. MS (ESI) m/z=185 (M+H$^+$)

1H NMR (300 MHz, CDCl3), δ: 5.55 (m, 1H), 5.02 (m, 2H), 3.85 (dt, 3.9 Hz, 12.0 Hz, 2H), 3.71 (s, 3H), 3.44 (dt, 2.4 Hz, 11.4 Hz, 2H), 2.30 (d, 7.5 Hz, 2H), 2.09 (m 2H), 1.54 (m, 2H).

Step 2: 4-Allyl-tetrahydro-pyran-4-carboxylic acid methyl ester (11 g, 59.78 mmol) was dissolved in iPrOH (300 mL). To this was added a aqueous solution of NaIO$_4$ (28 g, 130.4 mmol, 2.18 equiv.) in water (300 mL), followed by addition of OsO$_4$ (50 mg, crystals, in one portion) at rt. The solution was stirred with a mechanical stirrer at rt (water bath). After 30 min, milky cloudy mixture was formed. Stirring was continued for an additional period of 4 h. TLC (1% MeOH in DCM, and 5% MeOH in DCM) did not detect the SM. An aliquot was taken, dissolved in CDCl$_3$ and $^1$H NMR was run, which showed no alkene peak in the sample, and thus the reaction was judged to be complete. The reaction mixture was poured into ice water (200 mL) and EtOAc (200 mL). The two layers were separated and the aqueous layer was extracted with EtOAc (5×50 mL). More water was added to dissolve the solid to result in a clear solution. The combined extracts were washed with brine, and concentrated to dryness to get a liquid product. The liquid product was then subject to a distillation under reduced pressure to remove isopropanol. The remaining liquid was purified on a 80 g silica gel column, eluted with MeOH in DCM: 0% 0-5 min; 5-10% 5-25 min. 10-12% 25-60 min. Note: the product is not UV active. Anisaldehyde visualization was used. The product fractions were collected and concentrated to yield a liquid 6.6 g (60% yield) of the title compound.

LC/MS: $R_T$=1.26 min. MS (ESI) m/z=187 (M+H$^+$)

Intermediate (2)

4-(3-Oxo-propyl)tetrahydro-pyran-4-carboxylic acid methyl ester

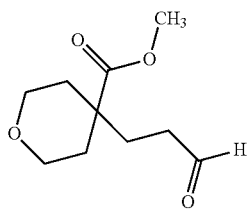

Step 1: 4-But-3-enyl-tetrahydro-pyran-4-carboxylic acid methyl ester

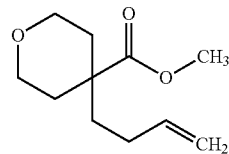

In a 250 mL round bottom flask was weighed 6.1 g (60 mmol) of diisopropylamine and dissolved in THF (100 mL). This solution was cooled to −78° C. To this solution was added 24 mL of 2 M butyllithium in hexane and stirred for 15 min, warmed up to 0° C. for 20 min, re-cooled to −78° C. To this mixture was added tetrahydro-pyran-4-carboxylic acid methyl ester (7.2 g, 50 mmol) in THF (10 mL). There was almost no color change (light a little bit). This was stirred at −78° C. for 45 min. Then, a mixture of 5 g of HMPA and bromo-butene (8.78 g, 65 mmol) was added slowly via cannula at −78° C. There was no noticeable change. When about half of this mixture was added, the dry ice-acetone bath was removed. When the addition was complete, the flask was submerged into an ice-water bath, stirred for 20 min; then at rt for 2 h. TLC (EtOAc/Heptane 1:1, paraldehyde visualization) showed the reaction was complete. The reaction mixture was poured into ice-water (100 mL) and ether (50 mL). The two layers were separated; the aqueous layer was extracted with ether (3×50 mL). The combined organic layers were washed with brine, dried ($K_2CO_3$), filtered, and concentrated in vacuo to obtain 10.4 g (87%) of the title product as a slightly yellow liquid. The material is pure enough to be used in the next step without further purification.

LCMS: $R_T$=3.07 min.; MS (ESI) m/z=199 (M+H).

1H NMR (CDCl3, 300 MHz) δ: 5.78 (ddt, 8.4 Hz, 11.7 Hz, 6.6 Hz, 1H), 4.97 (m, 2H), 3.90 (dt, 3.9 Hz, 11.7 Hz, 2H), 3.72 (s, 3H), 3.41 (dt, 2.6 Hz, 11.7 Hz, 2H), 2.10 (m, 2H), 1.98 (m, 2H), 1.58 (m, 4H).

Step 2: 4-But-3-enyl-tetrahydro-pyran-4-carboxylic acid methyl ester (6 g, 30 mmol) was dissolved in iPrOH (150 mL). To this was added a aqueous solution of NaIO$_4$ (14 g, 65.2 mmol, 2.18 equiv.) in water (150 mL), followed by addition of OsO$_4$ (25 mg, crystals, in one portion) at rt. The solution was stirred with a mechanical stirrer at rt (water bath). After 30 min, milky cloudy product was formed. Stirring was continued for 4 h. TLC (1% MeOH in DCM, and 5% MeOH in DCM) did not detect the starting material. An aliquot was taken and dissolved in CDCl$_3$ to run $^1$H NMR, there was no alkene peak in the sample. The reaction was judged to be complete. The reaction mixture was poured into ice water (200 mL) and EtOAc (200 mL). The two layers were separated and the aqueous layer was extracted with EtOAc (5×50 mL). More water was added to dissolve the solid resulting in a clear solution. The combined extracts were washed with brine, and concentrated to dryness to obtain a liquid product. The liquid product was subject to a distillation under reduced pressure to remove isopropanol. The remaining liquid was purified on a 50 g silica gel column, eluted with 50% EtOAc in Heptane. Note: the product is not UV active. Anisaldehyde visualization was used. The product fractions were collected and concentrated to yield 5.62 g (94% yield) of the title compound as a liquid.

LCMS: LC $R_T$=2.10 min.; MS (ESI) m/z=201 (M+H).

$^1$H 1H NMR (CDCl3, 300 MHz) δ: 9.74 m, 1H), 3.86 (dt, 3.6 Hz, 11.7 Hz, 2H), 3.72 (s, 3H), 3.41 (dt, 2.3 Hz, 11.7 Hz, 2H), 2.42 (m, 2H), 2.09 (m, 2H), 1.88 (m, 2H), 1.52 (m, 2H).

Intermediate (3)

4-(2-Oxo-ethyl)-piperidine-1,4-dicarboxylic acid 1-tert-butyl ester 4-ethyl ester

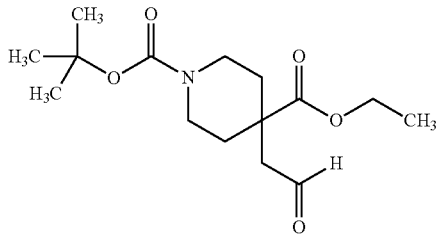 [SMILES: CCOC(=O)C1(CC=O)CCN(C(=O)OC(C)(C)C)CC1]

Step 1: 4-Allyl-piperidine-1,4-dicarboxylic acid 1-tert-butyl ester 4-ethyl ester

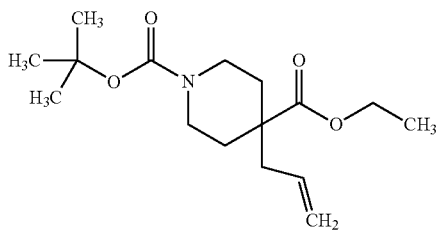 [SMILES: C=CCC1(C(=O)OCC)CCN(C(=O)OC(C)(C)C)CC1]

In a 250 mL round bottom flask was weighed 6.1 g (60 mmol) of diisopropylamine and dissolved in THF (100 mL). This solution was cooled to −78° C. (dry ice/acetone bath). To this solution was added 24 mL of 2.5 M (60 mmol) of butyl-lithium in hexane and stirred for 15 min, warmed up to 0° C. for 20 min, re-cooled to −78° C. To this mixture was added piperidine-1,4-dicarboxylic acid 1-tert-butyl ester 4-ethyl ester (12.87 g, 50 mmol) in THF (10 mL). There was almost no color change. This was stirred at −78° C. for 45 min. Then, a mixture of 5 g of HMPA and 10.92 g of allyl iodide was added via cannula. The solution was still clear, light yellow color. This mixture was stirred at −78° C. for 20 min, then the dry ice bath was removed and the stirring was continued to allow the reaction mixture warm to r.t. over 40 min. The reaction mixture was poured into ice (~50 g), saturated NH$_4$Cl aq. (50 mL) and ether (50 mL). The two layers were separated; the aqueous layer was extracted with ether (3×50 mL). The combined organic layers were washed with brine, dried (K$_2$CO$_3$), filtered, and concentrated in vacuo to obtain 15 g (100%) of the title compound as a yellow liquid, LCMS: LC $R_T$=3.45 min, MS (ESI) m/z=198, 242 (M−tBu).

1H NMR (300 MHz, CDCl3) δ: 1H NMR (300 MHz, CDCl3): 5.68 (m, 1H); 5.07 (, bs, 1H), 5.04 (d, 10.2 Hz, 1H), 4.17 (q, 7.2, 2H), 3.88 (broad d, 9 Hz, 2H), 2.9 (broad t, 12.9 Hz, 2H), 2.27 (d, 7.8 Hz, 2H), 2.1 (broad d, 13.2 Hz), 1.45 (s, 9H), 1.26 (t, 7.2 Hz, 3H).

Step 2: 4-Allyl-piperidine-1,4-dicarboxylic acid 1-tert-butyl ester 4-ethyl ester (2.97 g, 10 mmol) was dissolved in iPrOH (50 mL) and H$_2$O (10 mL). To this was added a aqueous solution of NaIO$_4$ (4.68 g, 21.8 mmol) in water (40 mL), followed by addition of OsO$_4$ (8.4 mg, crystals, in one portion) at rt. The solution was stirred at rt. After 30 min, milky cloudy formed. Stirring was continued overnight. TLC and LC/MS did not detect the SM, but it was still very milky. The reaction mixture was poured into ice water (20 mL) and EtOAc (30 mL). The two layers were separated and the aqueous layer was extracted with EtOAc (3×15 mL). The combined extracts were washed with brine, and concentrated to dryness to obtain a liquid. The liquid was subject to a distillation under reduced pressure to remove isopropanol. The remaining liquid was purified on a 50 g silica gel column, eluted with MeOH in DCM (0-5%). Note: the product is not UV active. Anisaldehyde visualization was used. The product fractions were collected and concentrated to yield 1.03 g (34% yield) of the title compound as a liquid.

LC/MS: $R_T$=2.84 min. MS (ESI) m/z=300 (M+H$^+$)

1H NMR (300 MHz, CDCl3) δ: 9.73 (t, 1.8 Hz, 1H), 4.22 (q, 7.2 Hz, 2H), 3.69 (m, 2H), 3.20 (m, 2H), 2.68 (m, 2H), 2.12 (m, 2H), 1.52 (m, 2H), 1.49 (s, 9H), 1.27 (t, 7.2 Hz, 3H)

Intermediate (4)

4-(3-Oxo-propyl)-piperidine-1,4-dicarboxylic acid 1-tert-butyl ester 4-ethyl ester

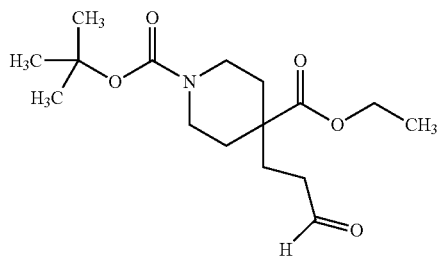 [SMILES: CCOC(=O)C1(CCC=O)CCN(C(=O)OC(C)(C)C)CC1]

Step 1: 4-But-3-enyl-piperidine-1,4-dicarboxylic acid 1-tert-butyl ester 4-ethyl ester

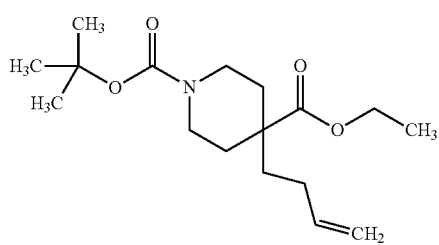 [SMILES: C=CCCC1(C(=O)OCC)CCN(C(=O)OC(C)(C)C)CC1]

A mixture of THF (160 mL) and diisopropyl amine (9.92 mL, 70.8 mmol, 1.2 eq) was cooled to −78° C. and a 2.5 M solution of n-BuLi in heptanes (28.3 mL, 70.8 mmol, 1.2 equiv.) was added slowly. The solution was stirred for 15 min, warmed to 0° C. for 20 min and cooled back to −78° C. Ethyl N-Boc-piperidine-4-carboxylate (11 mL, 59 mmol, 1 eq.) in 10 mL of THF was added drop-wise and stirred for 40 min before it was warmed to rt. The reaction mixture was stirred for 12 h, transferred to a separatory funnel, quenched with 500 mL of water and extracted with ethyl acetate (2×300 mL). The combined organics were dried over $Na_2SO_4$ and concentrated under vacuum to give the title compound as an yellow oil (13.9 g, 76%).

LC/MS: LC $R_T$=4.15 mins. MS (ESI) m/z=312 (M+H$^+$)

1H NMR (300 MHz, CDCl3) δ: 5.75 (ddt, 1H), 5.02 (d, 1H), 4.96 (t, 1H), 4.18 (q, 2H), 3.89-3.86 (m, 2H), 2.88 (t, 2H), 2.11 (d, 2H), 1.99-1.93 (m, 2H), 1.66-1.57 (m, 2H), 1.45 (s, 9H), 1.43-1.32 (m, 2H), 1.27 (t, 3H)

Step 2: 4-But-3-enyl-piperidine-1,4-dicarboxylic acid 1-tert-butyl ester 4-ethyl ester (13.5 g, 43.48 mmol, 1 eq) was dissolved in i-PrOH (217 mL) and a solution of $NaIO_4$ (20.23 g, 94.6 mmol, 2.18 eq) in 217 mL of water was added followed by $OsO_4$ (37 mg, 0.144 mmol, 0.003 eq). The reaction mixture was vigorously stirred for 6 h. The reaction mixture was then quenched with 1500 mL of water, transferred to a separatory funnel and extracted with ethyl acetate (3×200 mL). The combined organics were dried over $Na_2SO_4$ and purified by column chromatography on silica gel (300 g column, 30% EtOAc in heptanes; 50 mL/min). This afforded 8.5 g (63%) of the title compound as a beige oil.

LCMS: LC $R_T$=3.62 min, MS (ESI) m/z=314;

1H NMR (300 MHz, CDCl3) δ: 9.75 (s, 1H), 4.17 (q, 2H), 4.16-4.14 (m, 2H), 2.87 (t, 2H), 2.43 (dt, 2H), 2.10 (d, 2H), 1.85 (t, 2H), 1.45 (s, 9H), 1.36 (dd, 2H), 1.27 (t, 3H).

Intermediate (5)

1-(2-Oxo-ethyl)-cyclohexane-1,4-dicarboxylic acid dimethyl ester

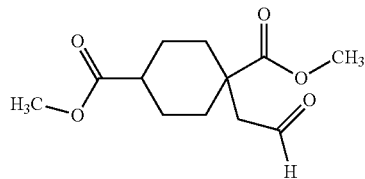

Step 1: 1-Allyl-cyclohexane-1,4-dicarboxylic acid dimethyl ester

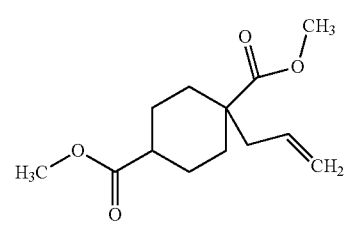 [SMILES: C=CCC1(C(=O)OC)CCC(C(=O)OC)CC1]

Diisopropylamine (4.55 g, 6.36 mL, 45 mmol) was dissolved in THF (100 mL) and cooled to −78° C. To this solution was added 2.5 M n-butyl lithium in hexane (18 mL, 45 mmol). The solution was stirred for 15 min, warmed up to 0° C. and stirred for an additional 20 min, then re-cooled to −78° C. Dimethyl 1,4-cyclohexanedicarboxylate (7.5 g, 37.5 mmol) in THF (10 mL) was then added and the reaction mixture was allowed to stir at −78° C. for 1 h followed by the addition of a mixture of hexamethyl-phosphoramide (HMPA) (5 g, 4.85 mL) and allyl iodide (8.19 g, 4.48 mL, 48.8 mmol). This mixture was stirred at −78° C. for 20 min. Then, the dry ice bath was removed and the stirring was continued to allow the reaction mixture to warm to room temperature over 1 h. The reaction mixture was poured into ice-water (100 mL) and ether (50 mL). The two layers were separated and the aqueous layer was extracted with ether (3×50 mL). The combined organic layers were washed with brine, dried over $Na_2SO_4$, and concentrated under vacuum to afford 9.23 g (97%) of the title compound.

Step 2: 1-Allyl-cyclohexane-1,4-dicarboxylic acid dimethyl ester (4.5 g, 17.71 mmol) was dissolved in 2-propanol (100 mL) and water (50 mL). To this was added an aqueous solution of $NaIO_4$ (9.5 g, 44.3 mmol) in water (50 mL), followed by addition of $OsO_4$ (0.025 g, crystals, in one portion). The reaction mixture was allowed to stir for 16 hours. Then, the reaction mixture was poured into ice water (50 mL) and ethyl acetate (EtOAc) (60 mL). The two layers were separated and the aqueous layer was extracted with EtOAc (3×50 mL). The combined organic solutions were washed with brine, and concentrated to dryness. The material was then purified over silica gel column eluting with ethyl acetate in heptanes (0-60%) to afford 3.09 g (72%) of the title compound.

LCMS: LC $R_T$=2.500 min, MS (ESI)=243 (M+H$^+$)

$^1$H NMR (CDCl$_3$), 300 MHz): δ 9.71 (s), 3.73 (s), 3.72-3.67 (m), 3.66 (s), 2.57 (s), 2.37-2.27 (m), 1.96-1.80 (m), 1.73-1.55 (m), 1.40-1.22 (m).

Intermediate (6)

1-(2-Oxo-ethyl)cyclohexanecarboxylic acid methyl ester

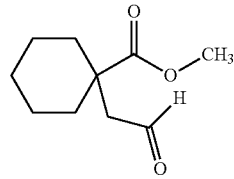

Step 1: 1-Allyl-cyclohexanecarboxylic acid methyl ester

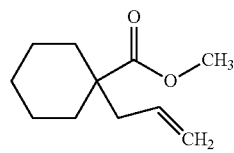

To a solution of diisopropylamine (10 mL, 72 mmol) in tetrahydrofuran (100 mL) pre-cooled to −69° C. was added a 2.5 M solution of n-butyllithium in hexanes (29 mL, 72 mmol) dropwise. Following addition, the reaction mixture was warmed to 0° C. for 30 min and then re-cooled to −70° C. To the mixture was added a solution of methyl cyclohexane carboxylate (8.9 mL, 60 mmol) in tetrahydrofuran (30 mL) dropwise. After stirring for 30 min, a solution of allyl iodide (7.2 mL, 78 mmol) in HMPA (5 mL) was added dropwise. The cooling bath was removed to allow the mixture to warm to 20° C. After 1.5 h, the reaction mixture was poured into H₂O (200 mL). The two layers were separated and the aqueous layer was extracted with Et₂O (100 mL). The organic solutions were combined and dried over K₂CO₃, filtered and concentrated to afford 11 g of the title compound as an oil.

Step 2: To a solution of 1-allyl-cyclohexanecarboxylic acid methyl ester (4 g, 21.5 mmol) in isopropanol (35 mL) was added a solution of sodium periodate (10.1 g, 47.3 mmol) in H₂O (35 mL) followed by the addition of osmium tetroxide (16 mg, 0.065 mmol). More Isopropanol (30 mL) and H₂O (35 mL) was added and the resulting suspension was stirred for 24 hours. Then, the reaction mixture was poured into ice/H₂O (200 mL) and extracted with EtOAc (2×200 mL). The organic solutions were combined and dried over Na₂SO₄, filtered and concentrated to provide a crude oil which was purified by flash column chromatography (10 to 60% EtOAc/heptane) to provide 1.24 g (31% yield over two steps) of the title compound as an oil.

¹H NMR (300 MHz, CDCl₃) δ: 9.72 (t, J=2.02 Hz, 1H), 3.71 (s, 3H), 2.64 (d, J=2.02 Hz, 2H), 2.04 (m, 2H), 1.57-1.37 (m, 8H)

Intermediate (7)

1-(3-Oxo-propyl)cyclopentanecarboxylic acid methyl ester

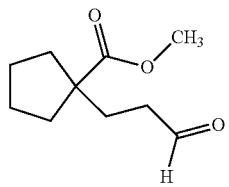

Step 1: 1-But-3-enyl-cyclopentanecarboxylic acid methyl ester

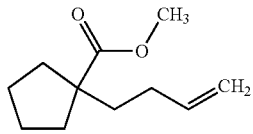

To a solution of diisopropylamine (10.5 mL, 75 mmol) in tetrahydrofuran (100 mL) pre-cooled to −75° C. was added a 2.5 M solution of n-butyllithium in hexanes (30 mL, 75 mmol) dropwise. Following addition, the reaction mixture was warmed to 0° C. for 30 min and then re-cooled to −75° C. To the mixture was added a solution of methyl cyclopentane carboxylate (8 g, 62 mmol) in tetrahydrofuran (40 mL) dropwise. After stirring for 30 min, a solution of 4-bromo-1-butene (8.2 mL, 81 mmol) in HMPA (6 mL) was added dropwise. The cooling bath was removed to allow the mixture to warm to 20° C. After 1.5 h, the reaction mixture was poured into ice/H₂O (200 mL). The two layers were separated and the aqueous layer was extracted with Et₂O (100 mL). The organic solutions were combined and dried over K₂CO₃, filtered and concentrated to afford the 12.1 g of the title compound as an oil. LC/MS: R_T=3.57 min. MS (ESI) m/z=183 (M+H⁺)

Step 2: To a solution of 1-but-3-enyl-cyclopentanecarboxylic acid methyl ester (4 g, 21.5 mmol) in Isopropanol (35 mL) was added a solution of sodium periodate (10.1 g, 47.3 mmol) in H₂O (35 mL) followed by the addition of osmium tetroxide (16 mg, 0.065 mmol). More Isopropanol (30 mL) and H₂O (35 mL) were added and the resulting suspension was stirred for 24 hours and then poured onto ice/H₂O (200 mL) and extracted with EtOAc (2×200 mL). The organic solutions were combined and dried over Na₂SO₄, filtered and concentrated to provide a crude oil which was purified by flash column chromatography (10 to 60% EtOAc/heptane) to provide 2.27 g (57% yield over two steps) of the title compound as an oil.

¹H NMR (300 MHz, CDCl₃) δ: 9.76 (s, 1H), 3.67 (s, 3H), 2.42 (t, J=7.70 Hz, 2H), 2.13 (m, 2H), 1.94 (t, J=7.70 Hz, 2H), 1.66 (m, 4H), 1.48 (m, 2H)

Intermediate (8)

4-(tert-Butyl-diphenyl-silanyloxy)-1-(2-oxo-ethyl)-cyclohexanecarboxylic acid methyl ester

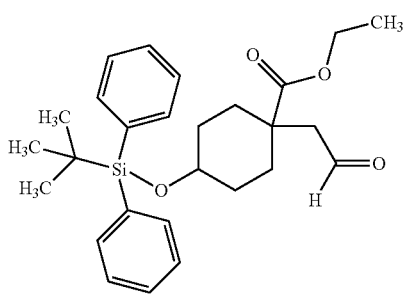 [SMILES: CCOC(=O)C1(CC=O)CCC(O[Si](c2ccccc2)(c2ccccc2)C(C)(C)C)CC1]

Step 1: 4-(tert-Butyl-diphenyl-silanyloxy)-cyclohexanecarboxylic acid ethyl ester

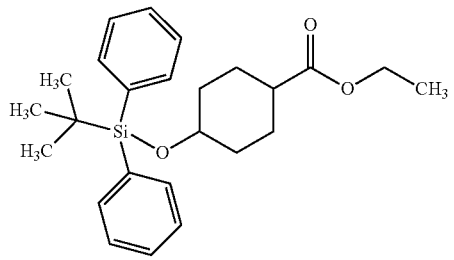 [SMILES: CCOC(=O)C1CCC(O[Si](c2ccccc2)(c2ccccc2)C(C)(C)C)CC1]

To a solution of ethyl 4-hydroxycyclohexane carboxylate (5 g, 29.03 mmol) in dichloromethane (200 mL) was added imidazole (4.97 g, 73 mmol) and tert-butylchlorodiphenylsilane (15.96 g, 15.2 mL, 58 mmol). The reaction mixture was allowed to stir at room temperature over night. The reaction mixture was poured into water (125 mL) in a separatory funnel and the phases were separated. The aqueous phase was extracted with dichloromethane (2×200 mL). The combined organic solutions were washed with brine, dried over Na₂SO₄, and concentrated under vacuum. Purification by column chromatography on silica gel eluting with ethyl acetate in heptanes (0-10%) afforded 10.55 g (89%) of the title compound.

Step 2: 1-Allyl-4-(tert-butyl-diphenyl-silanyloxy)-cyclohexanecarboxylic acid ethyl ester

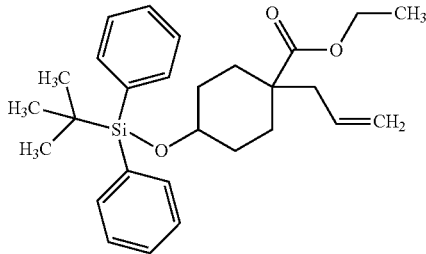 [SMILES: C=CCC1(C(=O)OCC)CCC(O[Si](c2ccccc2)(c2ccccc2)C(C)(C)C)CC1]

Diisopropylamine (3.14 g, 4.38 mL, 31 mmol) was dissolved in THF (100 mL) and cooled to −78° C. To this solution was added 2.5 M n-butyl lithium in hexane (12.4 mL, 31 mmol) and stirred for 15 min, warmed up to 0° C. and stirred for an additional min, then re-cooled to −78° C. 4-(tert-Butyl-diphenyl-silanyloxy)-cyclohexanecarboxylic acid ethyl ester (10.5 g, 25.6 mmol) in THF (15 mL) was then added and the reaction mixture was allowed to stir at −78° C. for 1 h followed by the addition of a mixture of hexamethyl-phosphoramide (HMPA) (7 mL) and allyl iodide (5.59 g, 33.3.0 mmol). This mixture was stirred at −78° C. for 20 min. Then, the dry ice bath was removed and the stirring was continued to allow the reaction mixture to warm to room temperature over 1 h. The reaction mixture was poured into ice-water (100 mL) and ether (50 mL). The two layers were separated; the aqueous layer was extracted with ether (3×50 mL). The combined organic layers were washed with brine, dried over $Na_2SO_4$, and concentrated under vacuum to afford 11.4 g (99%) of the title compound.

LC/MS: $R_T$=4.935 min. MS (ESI) m/z=451 (M+H$^+$)

Step 3: 1-Allyl-4-(tert-butyl-diphenyl-silanyloxy)-cyclohexanecarboxylic acid ethyl ester (5 g, 11.1 mmol) was dissolved in 2-propanol (100 mL) and water (50 mL). To this was added an aqueous solution of $NaIO_4$ (5.94 g, 27.8 mmol) in water (50 mL), followed by addition of $OsO_4$ (0.025 g, crystals, in one portion). The reaction mixture was allowed to stir for 16 hours at rt. The reaction mixture was poured into ice water (50 mL) and ethyl acetate (EtOAc) (60 mL). The layers were separated and the aqueous layer was extracted with EtOAc (3×50 mL). The combined organic layers were washed with brine, and concentrated to dryness. The resulting product was then purified over silica gel column eluting with ethyl acetate in heptanes (0-60%) to afford 4.45 g (87%) of the title compound.

LC/MS: $R_T$=4.551 min. MS (ESI) m/z=453 (M+H$^+$)

$^1$H NMR (CDCl$_3$), 300 MHz): δ 9.74 (s), 9.67 (s), 7.66 (d, J=6.23 Hz), 7.43-7.31 (m), 4.20 (q, j=6.96), 4.16-4.01 (m), 3.89-3.80 (m), 3.75-3.51 (m), 2.49 (d, J=2.2 Hz) 2.32-2.14 (m), 1.93-1.78 (m), 1.70-1.45 (m), 1.30-1.15 (m), 1.06 9 s), 105 (s), 0.92-0.83 (m).

Intermediate (9)

[4-((S)-3-Oxo-cyclopentyl)-phenyl]-carbamic acid benzyl ester

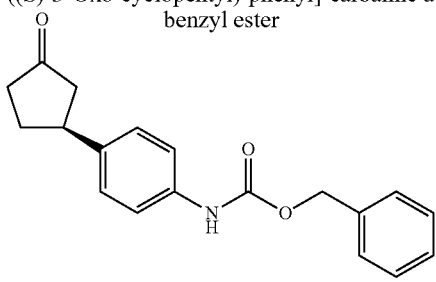

In a 50 mL round bottom flask was charged with Rh(acac)(C$_2$H$_4$)$_2$(acetylacetonatobis-(ethylene)rhodium (I), CAS 12082-47-2) (54 mg, 0.21 mmol, 3 mol %) and (S)-(+)-(3,5-dioxa-4-phospha-cyclohepta[2,1-a:3,4-a']dinaphthalen-4-yl)-diethylamine (from Strem Chemicals, Inc. CAS: 252288-04-3) (210 mg, 0.542 mmol, 7.5 mol %). To this was added 18 mL of dioxane and 1.8 mL of water. The flask was purged with N$_2$/vacuum cycle 3 times. The solution was stirred at rt for 5 min. 4-Benzyloxycarbonylamino-boronic acid (CAS 192804-36-7) (5.39 g, 19.8 mmol, 2.28 equiv.) was added in powder form and the solution was heated in a pre-heated oil bath set at 105° C. externally and was kept at that temperature for 5 min to ensure the inside and outside temperature was in equilibrium. To this was added slowly cyclopentenone (710 mg, 8.66 mmol, 1 equiv.) in liquid neat form drop-wise, and the resulting mixture was stirred at 105° C. (external temperature) for 35 min. The reaction was cooled to rt and quenched with NaHCO$_3$ aq (15 mL) and EtOAc 20 mL. The two layers were separated and the aqueous layer was extracted with EtOAc (2×20 mL). The combined extracts were washed with NaHCO$_3$ aq. (10 mL), and brine (10 mL), and dried (K$_2$CO$_3$). The solution was filtered through a silica gel pad, eluted with EtOAc. The filtrate was concentrated to dryness. The residue was dissolved in 30% EtOAc in heptane and loaded onto a 50 g silica gel column, eluted with 30% EtOAc in heptane to obtain a crude product. This was crystallized from 30% EtOAc in heptane to obtain 2.15 g (80% yield) of the title compound as a very white crystalline material.

m.p. 96.3-98.5° C.

LC/MS: $R_T$=3.20 min. MS (ESI) m/z=310 (M+H$^+$)

[a]$_D$=−28.4 in chloroform (c=0.5 g/100 mL); Chiral HPLC: ee=57.3%. Chiral HPLC conditions: Agilent 1200 HPLC system; CHIRALCEL OD-H, 150 mm×4.6 mm ID, 5 micron; Heptane:Ethanol=50:50; Flow rate: 0.70 mL/min; Detection: UV 220 nm; injection volume: 10 μL.

$^1$H NMR (300 MHz, CDCl$_3$) δ: 7.37 (m, 5H), 7.26-7.18 (m, 4H), 6.62 (s, 1H), 5.21 (s, 2H), 3.38 (m, 1H), 2.65 (dd, 7.5 Hz, 18.3 Hz, 1H), 2.50-2.23 (m, 4H), 1.95 (m, 1H).

Intermediate (10)

{4-[(S)-3-(2-Methyl-pyrrolidin-1-yl)-cyclopentyl]-phenyl}-carbamic acid benzyl ester

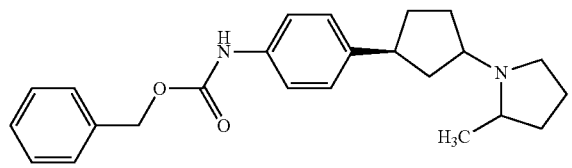 [SMILES: CC1CCCN1C1CC[C@H](c2ccc(NC(=O)OCc3ccccc3)cc2)C1]

[4-((S)-3-Oxo-cyclopentyl)-phenyl]-carbamic acid benzyl ester (618 mg, 2 mmol, 1 equiv.) was dissolved in DCE (20 mL). To this solution was transferred a solution of 2-methylpyrrolidine (212 mg, 2.5 mmol, 1.25 equiv.) in 3 mL of DCE, followed by acetic acid (360 mg, 6 mmol, 3 equiv) in DCE (2 mL), then by addition of powder NaBH(OAc)$_3$ (1.27 g, 6 mmol, 3 equiv.) in one portion under N$_2$ at r.t. The yellowish milky solution was stirred at r.t. 24 h. The reaction was diluted with DCM (20 mL) and quenched with 10 mL of NaHCO$_3$. The two layers were separated, and the aqueous layer was extracted with DCM (10 mL×2). The combined DCM extracts were washed with sodium bicarbonate (10 mL), brine (15 mL), dried (anhydrous potassium carbonate), filtered, and concentrated. The residue, a thick oil, was dissolved in DCM, and purified on a silica gel column to afford 0.61 g (81%) of the title compound.

LC/MS: $R_T$=2.74 min. MS (ESI) m/z=379(M+H$^+$)
$^1$H NMR in CDCl$_3$ showed two sets of signals in approximately 1:1 ratio.
$^1$H NMR (300 MHz, CDCl$_3$) δ: 7.54-7.13 (m), 6.68 (bs), 5.19 (s), 3.36-2.81 (m), 2.60 (m), 1.17 (m).

Intermediate (11)

[4-((S)-3-Hydroxy-cyclopentyl)-phenyl]-carbamic acid benzyl ester

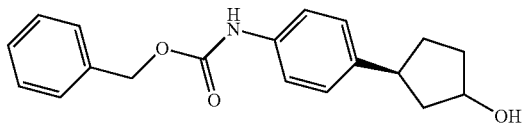 [SMILES: O=C(Nc1ccc([C@H]2CCC(O)C2)cc1)OCc1ccccc1]

[4-((S)-3-Oxo-cyclopentyl)-phenyl]-carbamic acid benzyl ester (150 mg, 0.5 mmol) was dissolved in EtOH (1 mL) and EtOAc (0.1 mL) to form a clear solution. To this solution was added powder NaBH$_4$ (50 mg) with stirring. The reaction was judged to be complete by TLC (30% EtOAc in heptane). The reaction was quenched by EtOAc (2 mL) and NaHCO$_3$ aq. solution (2 mL). The two layers were separated and the aqueous layer was extracted with EtOAc (2×2 mL). The combined extracts were washed with NaHCO$_3$ aq. (2 mL), brine (2 mL), and dried (K$_2$CO$_3$). The solution was filtered through a silica gel pad, eluted with EtOAc. The filtrate was concentrated to dryness to afford 155 mg (100%) of the title compound as a very white crystalline material. mp 99.0-100.6° C.
LC/MS: $R_T$=3.07 min. MS (ESI) m/z=312 (M+H$^+$)
$^1$H NMR in CDCl$_3$ showed two sets of signals in approximately 1:1.4 ratio.
$^1$H NMR (300 MHz, CDCl$_3$) δ: 7.41-7.15 (m), 6.63 (s), 5.20 (s), 4.51 (bs), 4.44 (bs), 3.35 (m), 3.00 (m), 2.44 (m), 2.21 (m), 2.09-1.42 (m).

Intermediate (12)

Methanesulfonic acid (S)-3-(4-benzyloxycarbonylamino-phenyl)-cyclopentyl ester

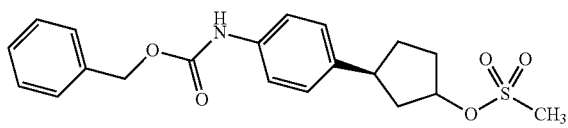 [SMILES: CS(=O)(=O)OC1CC[C@H](c2ccc(NC(=O)OCc3ccccc3)cc2)C1]

To a solution of [4-((S)-3-hydroxy-cyclopentyl)-phenyl]-carbamic acid benzyl ester (0.44 g, 1.4 mmol) in DCM (8 mL) was added Et$_3$N (214 mg, 0.3 mL, 2.12 mmol, 1.5 equiv.). The solution was cooled in an ice-water bath and then de-aerated by vacuum/nitrogen exchange. To this solution was transferred a solution of methanesulfonyl chloride (242 mg, 2.12 mmol, 1.5 equiv.) in DCM (2 mL). The clear solution was stirred with the ice-water bath on all the time for 1 h. TLC (50% EtOAc in heptane) indicated that the reaction was complete. The reaction was quenched by diluting with DCM (10 mL), followed by addition of NaHCO$_3$ aq. (5 mL). The two layers were separated and the aqueous layer was extracted with DCM (2×5 mL). The combined extracts were washed successively with NaHCO$_3$ aq. (5 mL), brine (5 mL) and dried (K$_2$CO$_3$). The solution was filtered through a silica gel pad, eluted with 5% MeOH in DCM. The filtrate was concentrated to dryness to obtain 510 mg (yield: 93%) of the title compound as an off-white wax-like solid material.
LC/MS: $R_T$=3.41 min. MS (ESI) m/z=390 (M+H$^+$)
$^1$H NMR in CDCl3 showed two sets of signals in approximately 1:1.4 ratio.
$^1$H NMR (300 MHz, CDCl3) δ: 7.41-7.15 (m), 6.6 (s), 5.25 (m), 5.20 (s), 3.35 (m), 3.00 (m), 2.44 (m), 2.21 (m), 2.09-1.42 (m).

Intermediate (13)

{4-[(S)-3-((S)-2-Methyl-pyrrolidin-1-yl)-cyclopentyl]-phenyl}-carbamic acid benzyl ester

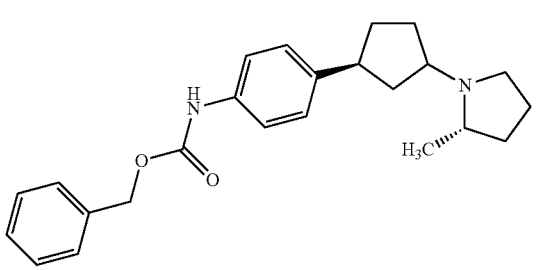 [SMILES: C[C@H]1CCCN1C1CC[C@H](c2ccc(NC(=O)OCc3ccccc3)cc2)C1]

Methanesulfonic acid (S)-3-(4-benzyloxycarbonylamino-phenyl)cyclopentyl ester (Intermediate 12) (510 mg, 1.31 mmol, 1 equiv.) was dissolved in 8 mL of anhydrous acetonitrile. This solution was transferred into a flask containing (S)-2-methyl-pyrrolidine (445 mg, 5.24 mmol, 4 equiv.) and K$_2$CO$_3$ (800 mg, 5.76 mmol, 4.4 equiv.). The suspension was de-gassed by vacuum/nitrogen exchange 3 times, and then, heated on an oil bath set at 80° C. under nitrogen with stirring for 16 h. TLC (5% MeOH in DCM for SM) showed the reaction was complete. Acetonitrile was removed in vacuo. The residue was taken in water (5 mL) and DCM (20 mL). The two layers were separated and the aqueous layer was extracted with DCM (2×10 mL). The combined extracts were washed with NaHCO$_3$ aq. (5 mL), brine (5 mL), and dried (K$_2$CO$_3$). The solution was filtered. The filtrate was concentrated in vacuo to obtain a crude product which was purified on a silica gel column eluting with 5% 7N ammonia methanolic solution in DCM to afford 410 mg (84%) of the title compound.
LC/MS: $R_T$=2.76 min. MS (ESI) m/z=379 (M+H$^+$)
$^1$H NMR in CDCl3 showed two sets of signals in approximately 1:1.4 ratio.
1H NMR (300 MHz, CDCl3) δ: 7.42-7.14 (m), 6.62 (s), 5.19 (s), 3.22 (m), 2.98 (m), 2.75 (m), 2.54 (m), 2.19-1.41 (m), 1.13 (d, 6.3 Hz), 1.12 (d, 6.3 Hz).

Intermediate (14)

4-[(S)-3-((S)-2-Methyl-pyrrolidin-1-yl)-cyclopentyl]-phenylamine

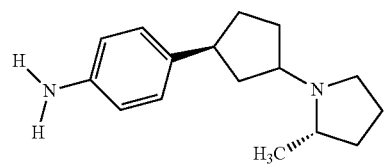 [SMILES: C[C@H]1CCCN1C1CC[C@H](c2ccc(N)cc2)C1]

{4-[(S)-3-((S)-2-Methyl-pyrrolidin-1-yl)-cyclopentyl]-phenyl}-carbamic acid benzyl ester (0.41 g, 1.08 mmol) was dissolved in MeOH (20 mL) to form a clear solution. The flask was flushed with nitrogen and Pd—C (10%) (50 mg) was added. The solution was stirred under $H_2$ atmosphere at rt for 4 h. TLC (5% of 7N ammonia methanolic solution in DCM) indicated that the reaction was complete. The solution was filtered through a Celite pad, rinsed with MeOH. The filtrate was concentrated in vacuo to obtain 0.27 g (100% yield) of the title compound as an oil.

This material was used as such in the subsequent steps.

LC/MS: $R_T$=0.20 min. MS (ESI) m/z=245 (M+H$^+$)

$^1$H NMR in CDCl$_3$ showed two sets of signals in approximately 1:1 ratio.

$^1$H NMR (300 MHz, CDCl$_3$) δ: 7.07 (d, 8.4 Hz), 7.02 (d, 8.4 Hz), 6.65 (d, 8.4 Hz), 3.57 (m), 3.33 (m), 3.19 (m), 2.97 (m), 2.72 (m), 2.32-1.69 (m), 1.58 (m), 1.24 (d, 6.0 Hz), 1.23 (d, 6.0 Hz).

Intermediate (15)

4-[(S)-3-(2-Methyl-pyrrolidin-1-yl)cyclopentyl]-phenylamine

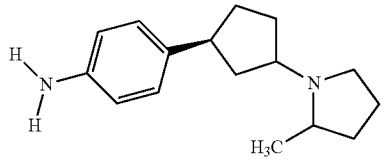

The title compound was prepared substantially in the same manner as the intermediate (14) by hydrogenation of {4-[(S)-3-(2-methyl-pyrrolidin-1-yl)-cyclopentyl]-phenyl}-carbamic acid benzyl ester (Intermediate 10).

$^1$H NMR (300 MHz, CDCl$_3$) δ: 7.07 (d, 8.4 Hz), 7.02 (d, 8.4 Hz), 6.65 (d, 8.4 Hz), 3.57 (m), 3.33 (m), 3.19 (m), 2.97 (m), 2.72 (m), 2.32-1.69 (m), 1.58 (m), 1.24 (d, 6.0 Hz), 1.23 (d, 6.0 Hz).

Intermediate (16)

Trifluoro-methanesulfonic acid 4-(tert-butyl-dimethyl-silanyloxy)-cyclohex-1-enyl ester

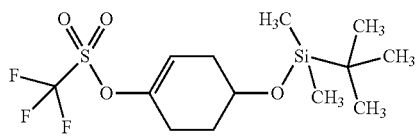 [SMILES: CC(C)(C)[Si](C)(C)OC1CC=C(OS(=O)(=O)C(F)(F)F)CC1]

LDA (0.8 M, 32 mL, 25.47 mmol, 1 equiv.) was cooled to −78° C. To this was added a solution of 4-(tert-butyl-dimethyl-silanyloxy)-cyclohexanone (5.82 g, 25.47 mmol, 1 equiv.) in THF (30 mL). The solution was stirred at −78° C. for 30 min. To this enolate was transferred a solution of Pyr-NTf2 (CAS 145100-51-2; 10 g, 25.47 mmol, 1 equiv.) in THF (60 mL) and kept stirring at −78° C. for 2 h. The reaction was diluted with EtOAc (50 mL) and NH$_4$Cl aq. (50 mL). The two layers were separated, and the aqueous layer was extracted with EtOAc (2×20 mL). The combined EtOAc extracts were washed with sodium bicarbonate (20 mL), brine (20 mL), dried (anhydrous potassium carbonate), filtered, and concentrated in vacuo to afford a liquid product. This was purified on a 120 g silica gel column eluted with 10% EtOAc in heptane to obtain 9 g (98% yield) of the title compound as a colorless liquid.

TLC: Rf=0.9 (silica gel, 30% EtOAc in heptane)

$^1$H NMR (300 MHz, CDCl3) δ: 5.60 (bs, 1H), 4.01 (m, 1H), 2.61-2.10 (m, 4H), 1.80 (m, 1H), 0.91 (s, 9H), 0.002 (s, 6H).

Intermediate (17)

{4-[4-(tert-Butyl-dimethyl-silanyloxy)-cyclohex-1-enyl]-phenyl}-carbamic acid benzyl ester

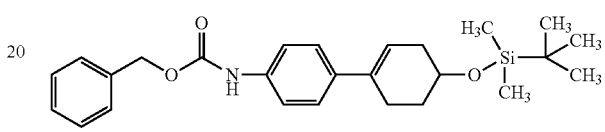

4-Benzyloxycarbonylamino-benzene boronic acid (1.42 g, 5.25 mmol, 1.5 equiv.) and LiCl (420 mg, 10.5 mmol, 3 equiv.) was placed in a 25 mL round bottom flask. To this was added Na$_2$CO$_3$ (2M) (7 mL) and EtOH (7 mL) to form a nice suspension. To this was transferred a solution of trifluoromethanesulfonic acid 4-(tert-butyl-dimethyl-silanyloxy)-cyclohex-1-enyl ester (1.26 g, 3.5 mmol, 1 equiv.) in toluene (18 mL). This suspension was subjected to a vacuum/nitrogen exchange three times. Pd(PPh$_3$)$_4$ (CAS 14221-01-3) (203 mg, 0.05 mmol, 7.5 mol %) was then added. The brown mixture was heated in an oil bath at 100° C. (external) for 50 min when the suspension became dark. At which time the TLC showed that the reaction was complete. The reaction was diluted with EtOAc (20 mL) and water (10 mL). The two layers were separated, and the aqueous layer was extracted with EtOAc (10 mL×2). The combined EtOAc extracts were washed with sodium bicarbonate (5 mL), brine (5 mL), dried (anhydrous potassium carbonate), filtered, and concentrated in vacuo to obtain a crude product. This was purified on a silica gel column eluted with 30% EtOAc in heptane to afford 1.5 g (98% yield) of the title compound as a crystalline white solid.

LC/MS: $R_T$=4.71 min. MS (ESI) m/z=438 (M+H$^+$)

$^1$H NMR (300 MHz, CDCl3) δ: 7.40-7.21 (m, 9H), 6.57 (bs, 1H), 5.85 (bs, 1H), 5.11 (s, 2H), 3.89, (m), 1, 2.50-2.24 (m, 3H), 2.08 (m, 1H), 1.83 (m, 1H), 1.67 (m, 1H), 0.82 (s, 9H, 0.0093 (s, 6H).

Intermediate (18)

4-[4-(tert-Butyl-dimethyl-silanyloxy)-cyclohexyl]-phenylamine

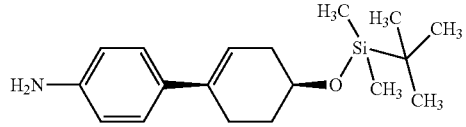

{4-[4-(tert-Butyl-dimethyl-silanyloxy)-cyclohex-1-enyl]-phenyl}-carbamic acid benzyl ester (Intermediate 16) (350 mg, 0.8 mmol) was dissolved in EtOAc (35 mL). After de-gas by vacuum/nitrogen exchange, Pd—C (70 mg) was added. The reaction mixture was first purged with nitrogen and then hydrogen introduced by vacuum/hydrogen purge cycle. The reaction mixture was stirred at rt overnight when TLC (30% EtOAc in heptane, UV) could not detect the starting material. The reaction mixture was filtered through a celite pad, rinsed with EtOAc. The filtrate was concentrated in vacuo. The residue was purified on a silica gel column, eluted with 10-20% EtOAc in heptane to obtain the title compound as an oil which solidified on standing 130 mg (0.42 mmol, 53% yield).

LC/MS: $R_T$=3.62 min. MS (ESI) m/z=306 (M+H$^+$)
$^1$H NMR (300 MHz, CDCl$_3$) δ: 7.02 (m, 2H), 6.63 (m, 2H), 4.03 (bs, 1H), 3.53 (bs, 2H), 2.38 (m, 1H), 1.75 (m, 2H), 1.87 (m, 2H), 1.55 (m, 2H), 1.53 (m, 2H), 0.91 (s, 9H), 0.04 (s, 6H).

nOe observed between signals of 7.02 and 2.38/1.87/1.55 ppm; 2.38 and 1.55/1.53; 4.03 and 1.75/1.53 ppm. nOe support the 1,4-cis-configuration.

Intermediate (19)

Cis-2-{4-[4-(tert-Butyl-dimethyl-silanyloxy)-cyclohexyl]-phenyl}-8-oxa-2-aza-spiro[4.5]decan-1-one

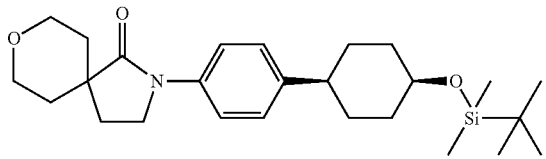 [SMILES: CC(C)(C)[Si](C)(C)O[C@H]1CC[C@@H](c2ccc(N3CCC4(CCOCC4)C3=O)cc2)CC1]

4-[4-(tert-Butyl-dimethyl-silanyloxy)-cyclohexyl]-phenylamine (Intermediate 18) (520 mg, 1.7 mmol, 1 equiv) was dissolved in DCE (15 mL). To this solution was transferred a solution of 4-(2-oxo-ethyl)-tetrahydro-pyran-4-carboxylic acid methyl ester (Intermediate 1) (317 mg, 1.7 mmol, 1 equiv.) in DCE (5 mL). To this clear solution was then added acetic acid (310 mg, 5.27 mmol, 3.1 equiv), in DCM (2 mL), followed by addition of powder NaBH(OAc)$_3$ (1080 mg, 5.1 mmol, 3 equiv.) in one portion under N$_2$ at r.t. The yellowish milky solution was stirred at r.t. overnight. The reaction was diluted with DCM (10 mL) and quenched with 10 mL NaHCO$_3$. The two layers were separated, and the aqueous layer was extracted with DCM (2×10 mL). The combined DCM extracts were washed with sodium bicarbonate (10 mL), brine (15 mL), dried (anhydrous potassium carbonate), filtered, and concentrated to obtain an intermediate product with MS of 476. The intermediate product obtained above was dissolved in THF (30 mL). To this solution was added a solution of potassium t-butoxide (1 M in THF) 1 mL (1 mmol, 1.1 equiv.) at r.t. The clear solution turned a little bit cloudy. After 5 min, TLC (2.5% of MeOH in DCM) showed the reaction was complete (spot to spot), LC/MS detected the product peak of 444 (t 2.491 min). The reaction mixture was quenched by dilution with EtOAc (20 mL) and water (10 mL). The two layers were separated. The aqueous layer was extracted with EtOAc (2×10 mL). The combined DCM extracts were washed with brine, dried (K$_2$CO$_3$), filtered, and concentrated on rotavap to yield a crude product. This material was dissolved in DCM (1 mL), loaded onto a 25 g of silica gel column, eluted with 2.5% MeOH in DCM to obtain the title compound.

LC/MS: $R_T$=4.58 min. MS (ESI) m/z=444 (M+H$^+$)
$^1$H NMR (300 MHz, CDCl3) δ: 7.50 (m, 2H), 7.17 (m, 2H), 3.99 (m, 2H), 3.95 (bs, 1H), 3.73 (t, 6.3 Hz, 2H), 3.52 (m, 2H), 2.43 (t, 11.1 Hz, 1H), 2.09 (m, 4H), 1.86 (m, 2H), 1.71 (m, 2H), 1.60-1.36 (m, 6H).

Intermediate (20)

2-[4-(4-Hydroxy-cyclohexyl)-phenyl]-8-oxa-2-aza-spiro[4.5]decan-1-one

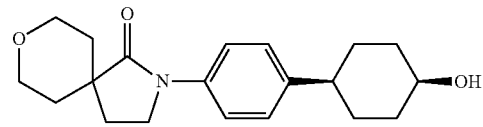 [SMILES: O=C1N(c2ccc([C@H]3CC[C@@H](O)CC3)cc2)CCC12CCOCC2]

Cis-2-{4-[4-(tert-butyl-dimethyl-silanyloxy)-cyclohexyl]-phenyl}-8-oxa-2-aza-spiro[4.5]decan-1-one (intermediate 19) (500 mg, 1.13 mmol) was dissolved in THF (10 mL). To this solution at rt was added TBAF (1 M in THF) (2.9 mL, 2.9 mmol, 2.5 equiv.). The reaction mixture was then heated to 60° C. (external) for 5 h. After the reaction was complete (TLC, 5% MeOH in DCM), the reaction was diluted with EtOAc (5 mL), quenched with NH$_4$Cl (aq. saturated, 5 mL). The two layers were separated and the aq. layer was extracted with EtOAc (2×15 mL). The EtOAc solution was combined, washed with NH$_4$Cl aq, NaHCO$_3$ aq, and brine (10 mL each), sequentially, and dried over K$_2$CO$_3$, filtered and concentrated. The crude product was purified on a silica gel column, eluted with 5% MeOH in DCM to afford 0.375 g (100% yield) of the title compound as a white solid.

LC/MS: $R_T$=2.69 min. MS (ESI) m/z=330 (M+H$^+$)
$^1$H NMR (300 MHz, CDCl3) δ: 7.57 (m, 2H), 7.24 (m, 2H), 4.13 (bs, 1H), 4.05 (dt, 4.2 Hz, 11.4 Hz, 2H), 3.79 (t, 7.2 Hz, 2H), 3.58 (dt, 2.7 Hz, 11.4 Hz, 2H), 2.53 (m, 1H), 2.13 (m, 4H), 1.90 (m, 4H), 1.56-1.41 (m, 3H).

Intermediate (21)

Cis-Methanesulfonic acid 4-[4-(1-oxo-8-oxa-2-aza-spiro[4.5]dec-2-yl)-phenyl]-cyclohexyl ester

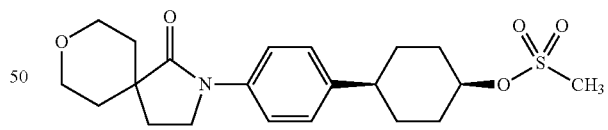

To a solution of cis-2-[4-(4-hydroxy-cyclohexyl)-phenyl]-8-oxa-2-aza-spiro[4.5]decan-1-one (Intermediate 20) (280 mg. 0.85 mmol) in DCM (5 mL) was added Et$_3$N (20.2 mL, 1.7 mmol, 2 equiv.). The solution was cooled to an ice-water bath and then de-aerated by vacuum/nitrogen exchange. To this solution was transferred a solution of methanesulfonyl chloride (146 mg, 1.2 mmol, 1.5 equiv.) in DCM (2 mL). The clear solution was stirred with the ice-water bath on all the time for 1 h. TLC (50% EtOAc in heptane) indicated that the reaction was complete. The reaction was quenched by diluting with DCM (10 mL), followed by addition of NaHCO$_3$ aq. (5 mL). The two layers were separated and the aqueous layer was extracted with DCM (2×5 mL). The combined extracts were washed successively with NaHCO$_3$ aq. (5 mL), brine (5 mL) and dried (K₂CO₃). The solution was filtered through a silica gel pad, eluted with 5% MeOH in DCM to afford 300 mg (87%) of the title compound as a white solid.

LC/MS: R$_T$=2.99 min. MS (ESI) m/z=408 (M+H⁺)

¹H NMR (300 MHz, CDCl3) δ: 7.60 (d, 8.7 Hz, 2H), 7.25 (d, 8.7 Hz, 2H), 5.07 (bs, 1H), 4.03 (dt, 4.2 Hz, 11.7 Hz, 2H), 3.80 (t, 6.9 Hz, 2H), 3.59 (dt, 2.5 Hz, 11.7 Hz, 2H), 3.05 (s, 3H), 2.53 (m, 1H), 2.14-2.03 (m, 6H), 1.91-1.71 (m, 6H), 1.46 (m, 2H).

Intermediate (22)

{4-[4-(tert-Butyl-dimethyl-silanyloxy)-cyclohex-1-enyl]-2-fluoro-phenyl}-carbamic acid benzyl ester

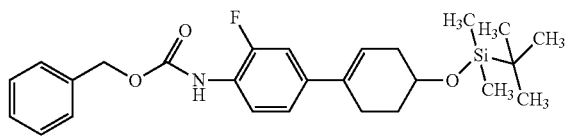 [SMILES: CC(C)(C)[Si](C)(C)OC1CC=C(c2ccc(NC(=O)OCc3ccccc3)c(F)c2)CC1]

4-Benzyloxycarbonylamino-3-fluoro-benzene boronic acid (2.53 g, 8.75 mmol, 1.25 equiv.) and LiCl (840 mg, 21 mmol, 3.0 equiv.) was placed in a 125 mL round bottom flask equipped with a condenser. To this was added aq. Na₂CO₃ (2 M, 14 mL) and EtOH (14 mL) to form a nice suspension. To this was transferred a solution of trifluoromethanesulfonic acid 4-(tert-butyl-dimethyl-silanyloxy)-cyclohex-1-enyl ester (2.52 g, 7 mmol, 1 equiv.) in toluene (36 mL). This suspension was subjected to a vacuum/nitrogen exchange three times. Pd(PPh₃)₄ (CAS 14221-01-3) (406 mg, 0.10 mmol, 7.5 mol %) was then added. The brown mixture was heated in an oil bath at 100° C. for 40 min when the suspension became dark. TLC showed the reaction was complete. The reaction was diluted with ether (20 mL) and water (20 mL). The two layers were separated, and the aqueous layer was extracted with Et₂O (2×10 mL). The combined Et₂O extracts were washed with sodium bicarbonate (5 mL), brine (5 mL) and dried (anhydrous potassium carbonate). The solution was passed through a short Celite/silica gel pad, eluted with EtOAc. The filtrate was concentrated in vacuo to obtain a crude product. This was purified on silica gel column to get a solid. The solid was crystallized in 10% EtOAc in heptane to get 2.45 g (77%) of the title compound as a white crystalline solid. mp 116.1-119° C.

LC/MS: R$_T$=4.78 min. MS (ESI) m/z=456 (M+H⁺)

¹H NMR (300 MHz, CDCl3) δ: 8.00 (m, 1H), 7.42 (m, 5H), 7.14-7.04 (m, 2H), 6.87 (s, 1H), 5.95 (bs, 1H), 5.21 (s, 2H), 3.96 (m, 1H), 2.44 (m, 3H), 2.16 (m, 1H), 1.91 (m, 1H), 1.74 (m, 1H), 0.90 (s, 9H), 0.086 (s, 6H).

Intermediate (23)

[2-Fluoro-4-(4-hydroxy-cyclohex-1-enyl)-phenyl]-carbamic acid benzyl ester

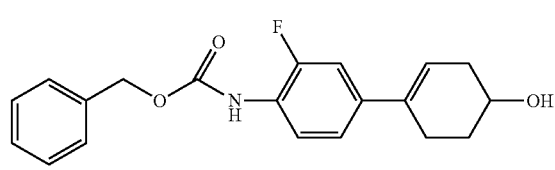 [SMILES: O=C(Nc1ccc(C2=CCC(O)CC2)cc1F)OCc1ccccc1]

{4-[4-(tert-Butyl-dimethyl-silanyloxy)-cyclohex-1-enyl]-2-fluoro-phenyl}-carbamic acid benzyl ester (340 mg, 0.75 mmol) was dissolved in THF (10 mL). To this solution at rt was added TBAF (1M in THF) (2 mL, 2 mmol). The reaction mixture was stirred at rt overnight. After the reaction was complete (TLC, 5% MeOH in DCM), the reaction was diluted with EtOAc (5 mL), quenched with NaHCO₃ (saturated, 5 mL). The two layers were separated and the aq. layer was extracted with EtOAc (15 mL×2). The EtOAc solution was combined, washed with NaHCO₃ aq, and brine (10 mL each), sequentially, and dried over K₂CO₃, filtered, concentrated. The crude product was purified on a silica gel column, eluted with 5% MeOH in DCM to obtain 230 mg (92% yield) of the title compound as a tan solid.

LC/MS: R$_T$=3.24 min. MS (ESI) m/z=342 (M+H⁺)

¹H NMR (300 MHz, CDCl3) δ: 8.02 (m, 1H), 7.42 (m, 5H), 7.14-7.04 (m, 2H), 6.88 (s, 1H), 5.98 (bs, 1H), 5.22 (s, 2H), 4.05 (bs, 1H), 2.53 (m, 3H), 2.21 (m, 1H), 1.99 (m, 1H), 1.82 (m, 1H).

Intermediate (24)

Methanesulfonic acid 4-(4-benzyloxycarbonylamino-3-fluoro-phenyl)-cyclohex-3-enyl ester

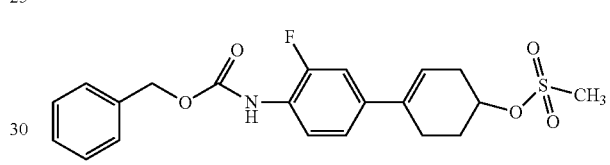

To a solution of [2-fluoro-4-(4-hydroxy-cyclohex-1-enyl)-phenyl]-carbamic acid benzyl ester (230 mg. 0.67 mmol) in DCM (5 mL) was added Et₃N (0.2 mL, 1.7 mmol, 2 equiv.). The solution was cooled to an ice-water bath and then de-aerated by vacuum/nitrogen exchange. To this solution was transferred a solution of methanesulfonyl chloride (146 mg, 1.2 mmol, 1.5 equiv.) in DCM (2 mL). The clear solution was stirred in an ice-water bath for 1 h. TLC (50% EtOAc in heptane) indicated that the reaction was complete. The reaction was quenched by diluting with DCM (10 mL), followed by addition of NaHCO₃ aq. (5 mL). The two layers were separated and the aqueous layer was extracted with DCM (2×5 mL). The combined extracts were washed with NaHCO₃ aq. (5 mL), brine (5 mL), and dried (K₂CO₃). The solution was filtered through a silica gel pad, eluted with 5% MeOH in DCM to afford 248 mg (88%) of the title compound.

LC/MS: R$_T$=3.54 min. MS (ESI) m/z=420 (M+H⁺)

¹H NMR (300 MHz, CDCl3) δ: 8.10 (m, 1H), 7.42 (m, 5H), 7.14-7.04 (m, 2H), 6.88 (s, 1H), 5.98 (bs, 1H), 5.22 (s, 2H), 4.05 (bs, 1H), 3.05 (s, 3H), 2.53 (m, 4H), 2.21 (m, 2H)

Intermediate (25)

{4-[4-(tert-Butyl-dimethyl-silanyloxy)-cyclohexyl]-2-fluoro-phenyl}-carbamic acid benzyl ester

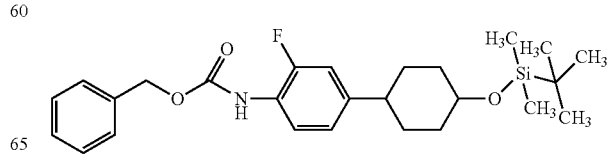

Step 1: 4-[4-(tert-Butyl-dimethyl-silanyloxy)-cyclohexyl]-2-fluoro-phenylamine

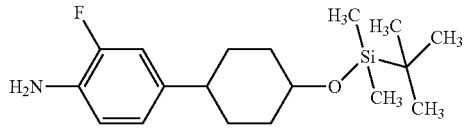 [SMILES: CC(C)(C)[Si](C)(C)OC1CCC(c2ccc(N)c(F)c2)CC1]

{4-[4-(tert-Butyl-dimethyl-silanyloxy)-cyclohex-1-enyl]-2-fluoro-phenyl}-carbamic acid benzyl ester (1.08 g, 2.37 mmol) was dissolved in MeOH (120 mL) and DCM (5 mL) to form a clear solution. The flask was flushed with nitrogen and Pd—C (10%) (108 mg) was added. The solution was stirred under hydrogen atmosphere at rt for 4 h. TLC (30% and 50% EtOAc in Heptane) indicated that the reaction was complete. The solution was filtered through a Celite pad, rinsed with MeOH. The filtrate was concentrated in vacuo to obtain 0.85 g (100% yield) of the title compound as an oil. This material was used immediately in the following reaction.

LC showed two components. Component one: $R_T$=4.39 min, 32%, MS (ESI) m/z 324; Component two: $R_T$=4.56 min, 68%, MS (ESI) m/z 324.

$^1$H NMR showed two sets of the signals in a ratio of approximately 2:1.

$^1$H NMR (300 MHz, CDCl3) δ: 6.72 (m), 3.98 (bs), 3.54 (bs), 2.33 (m), 1.88 (m), 1.74 (m), 1.51 (m), 1.38 (m), 0.87 (s), 0.85 (s), 0.025 (s), 0.0013 (s).

Step 2: 4-[4-(tert-Butyl-dimethyl-silanyloxy)-cyclohexyl]-2-fluoro-phenylamine (0.85 g, 2.4 mmol) was dissolved in DCM (20 mL). To this solution was transferred a solution of CbzCl (560 mg, 3.28 mmol, 1.3 equiv.) in 5 mL of DCM, followed by addition of powder anhydrous $K_2CO_3$ (0.99 g, 7.2 mmol, 3 equiv.). The reaction mixture was stirred at 0° C. to rt. overnight. The reaction was quenched by dilution with DCM (10 mL), followed by addition of $NaHCO_3$ aq. (5 mL). The two layers were separated and the aqueous layer was extracted with DCM (2×5 mL). The combined extracts were washed with $NaHCO_3$ aq. (5 mL), brine (5 mL) and dried ($K_2CO_3$). The solution was filtered and the filtrate was concentrated in vacuo to obtain the title compound.

LC showed two components. Component one: $R_T$=4.82 min, 34%, MS (ESI) m/z: 458; Component two: $R_T$=4.95 min, 66%, MS (ESI) m/z: 458.

$^1$H NMR showed two sets of the signals in a ratio of approximately 2:1.

$^1$H NMR (300 MHz, CDCl3) δ: 7.90 (m), 7.34-7.21 (m), 6.76 (bs), 5.16 (s), 3.99 (bs), 3.56 (bs), 2.39 (m), 1.90 (m), 1.81 (m), 1.74 (m), 1.70 (m), 1.49 (m), 1.39 (m), 0.87 (s), 0.85 (s), 0.024 (s), 0.0027 (s).

Intermediate (26)

2-{4-[4-(tert-Butyl-dimethyl-silanyloxy)-cyclohexyl]-2-fluoro-phenyl}-1-oxo-2,8-diaza-spiro[4.5]decane-8-carboxylic acid tert-butyl ester

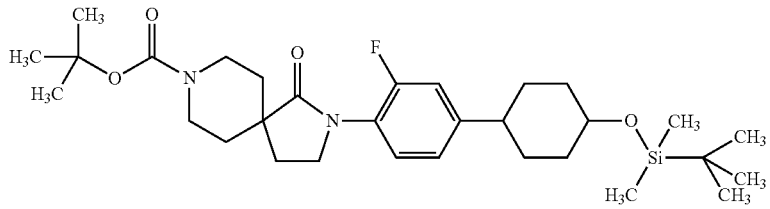 [SMILES: CC(C)(C)OC(=O)N1CCC2(CC1)CCN(c1ccc(C3CCC(O[Si](C)(C)C(C)(C)C)CC3)cc1F)C2=O]

Step 1: 4-[4-(tert-Butyl-dimethyl-silanyloxy)-cyclohexyl]-2-fluoro-phenylamine (520 mg, 1.7 mmol, 1 equiv) was dissolved in DCE (15 mL). To this solution was transferred a solution of 4-(2-oxo-ethyl)-piperidine-1,4-dicarboxylic acid 1-tert-butyl ester 4-ethyl ester (598 mg, 2.07 mmol, 1 equiv.) in DCE (5 mL). To this clear solution was then added acetic acid (372 mg, 6.21 mmol, 3 equiv) in DCM (2 mL), followed by addition of powder NaBH(OAc)$_3$ (1.31 g, 6.2 mmol, 3 equiv.) in one portion under $N_2$ at rt. The yellowish milky solution was stirred at rt overnight. The reaction was diluted with DCM (10 mL) and quenched with 10 mL of aqueous $NaHCO_3$. The two layers were separated, and the aqueous layer was extracted with DCM (10 mL×2). The combined DCM extracts were washed with sodium bicarbonate (10 mL), brine (15 mL), dried (anhydrous potassium carbonate), filtered, and concentrated to obtain the title compound as a liquid and was used in next step without further purification.

MS (ESI) m/z=607 (M+H). TLC $R_f$=0.75 (50% of EtOAc in heptane, UV).

LC showed two components. Component one: $R_T$=1.90 min, 12%, MS (ESI) m/z: 607; Component two: $R_T$=1.96 min, 88%, MS (ESI) m/z: 607.

$^1$H NMR (300 MHz, CDCl3) δ: 6.79 (m), 6.51 (m), 4.13 (q, 7.2 Hz), 3.98 (s), 3.82 (m), 3.08 (m), 2.33 (m), 2.11 (m), 1.86-1.66 (m), 1.52-1.47 (m), 1.40 (s), 1.20 (t, 7.2 Hz), 0.87 (s).

Step 2: The compound obtained above was dissolved in THF (30 mL). To this solution was added a solution of potassium t-butoxide (1M in THF) 2 mL (2 mmol, 1 equiv.) at r.t. The clear solution turned a little bit cloudy. After 30 min, the TLC (50% EtOAc in heptane) showed that the reaction was complete (spot to spot), LC/MS (ESI) detected the product peak of 561. The reaction mixtures were quenched by dilution with EtOAc (20 mL) and water (10 mL). The two layers were separated. The aqueous layer was extracted with EtOAc (2×10 mL). The combined DCM extracts were washed with brine, dried ($K_2CO_3$), filtered, and concentrated on rotavap to yield a crude product. This material was dissolved in DCM (1 mL), loaded onto a 25 g of silica gel column, eluted with 50% EtOAc in heptane to afford 0.72 g (62% over 2 steps) of the title compound as a light yellow solid. TLC $R_f$=0.60 (50% of EtOAc in heptane, UV).

LC showed two components. Component one: $R_T$=1.68 min, 13%, MS (ESI) m/z: 561; Component two: $R_T$=1.74 min, 87%, MS (ESI) m/z: 561.

$^1$H NMR (300 MHz, CDCl3) δ: 6.79 (m), 6.52 (m), 3.98 (s), 3.83 (m), 3.08 (m), 2.87 (m), 2.33 (m), 2.11 (m), 1.88-1.67 (m), 1.54-1.46 (m), 1.40 (s), 0.87 (s).

Intermediate (27)

2-[2-Fluoro-4-(4-hydroxy-cyclohexyl)-phenyl]-1-oxo-2,8-diaza-spiro[4.5]decane-8-carboxylic acid tert-butyl ester

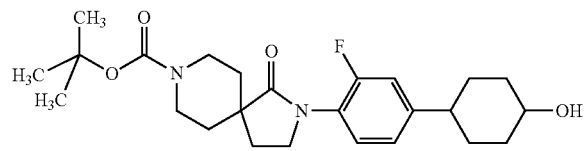 [SMILES: CC(C)(C)OC(=O)N1CCC2(CC1)CCN(c1ccc(C3CCC(O)CC3)cc1F)C2=O]

2-{4-[4-(tert-Butyl-dimethyl-silanyloxy)-cyclohexyl]-2-fluoro-phenyl}-1-oxo-2,8-diaza-spiro[4.5]decane-8-carboxylic acid tert-butyl ester (720 mg, 1.29 mmol) was dissolved in THF (10 mL). To this solution at rt was added TBAF (1M in THF) (2 mL, 2 mmol, 1.5 equiv.). The reaction mixture was then heated to 60° C. (bath set) for 5 h. The reaction was complete (TLC, 5% MeOH in DCM). The reaction was diluted with EtOAc (5 mL), quenched with NaHCO$_3$ (saturated aqueous solution, 5 mL). The two layers were separated and the aq. layer was extracted with EtOAc (15 mL×2). The EtOAc solution was combined, washed with brine (10 mL), and dried over K$_2$CO$_3$, filtered, and concentrated. The crude product was purified on a silica gel column eluted with 5% MeOH in DCM to afford 0.53 g (93% yield) of the title compound as a white solid.

LC showed two components. Component one: $R_T$=1.15 min, 12%, MS (ESI) m/z: 447; Component two: $R_T$=1.18 min, 88%, MS (ESI) m/z: 447.

$^1$H NMR (300 MHz, CDCl3) δ: 7.29 (m), 7.03 (m), 3.98 (s), 4.14 (m), 4.01 (m), 3.74 (m), 3.10 (m), 2.51 (m), 2.11 (m), 1.89 (m), 1.71-1.54 (m), 1.47 (s), 0.92 (s).

Intermediate (28)

2-[2-Fluoro-4-(4-methanesulfonyloxy-cyclohexyl)-phenyl]-1-oxo-2,8-diaza-spiro[4.5]decane-8-carboxylic acid tert-butyl ester

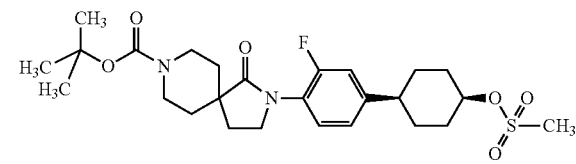 [SMILES: CC(C)(C)OC(=O)N1CCC2(CC1)CCN(c1ccc([C@H]3CC[C@@H](OS(C)(=O)=O)CC3)cc1F)C2=O]

To a solution of 2-[2-fluoro-4-(4-hydroxy-cyclohexyl)-phenyl]-1-oxo-2,8-diaza-spiro[4.5]decane-8-carboxylic acid tert-butyl ester (530 mg, 1.18 mmol) in DCM (8 mL) was added Et3N (179 mg, 0.3 mL, 1.77 mmol, 1.5 equiv.). The solution was cooled to an ice-water bath and then de-aerated by vacuum/nitrogen exchange. To this solution was transferred a solution of methanesulfonyl chloride (202 mg, 1.77 mmol, 1.5 equiv.) in DCM (2 mL). The clear solution was stirred with the ice-water bath on all the time for 1 h. TLC (5% MeOH in DCM) indicated that the reaction was complete. The reaction was quenched by diluting with DCM (10 mL), followed by addition of NaHCO$_3$ aq. (5 mL). The two layers were separated and the aqueous layer was extracted with DCM (2×5 mL). The combined extracts were washed with NaHCO$_3$ aq. (5 mL), brine (5 mL) and dried (K$_2$CO$_3$). The solution was filtered through a silica gel pad, eluted with 5% MeOH in DCM. The filtrate was concentrated to dryness and purified again on a silica gel column, eluted with 5% MeOH in DCM to eliminate the minor component to afford 0.4 g (64% yield) of the title compound as an off-white wax-like solid material.

LC showed a single component. $R_T$=1.23 min, MS (ESI) m/z: 525 (M+H$^+$).

$^1$H NMR (300 MHz, CDCl3) δ: 7.29 (m, 1H), 7.01 (m, 2H), 5.06 (bs, 1H), 3.99 (m, 2H), 3.75 (t, 6.9 Hz, 2H), 3.10 (m, 2H), 3.05 (s, 3H), 2.58 (m, 1H), 2.22 (m, 2H), 2.13 (m, 2H), 1.95 (m, 2H), 1.78 (m, 4H), 1.56 (m, 4H), 1.47 (s, 9H).

EXAMPLES

Example 1

2-{4-[(S)-3-((S)-2-Methyl-pyrrolidin-1-yl)-cyclopentyl]-phenyl}-8-oxa-2-aza-spiro[4.5]decan-1-one

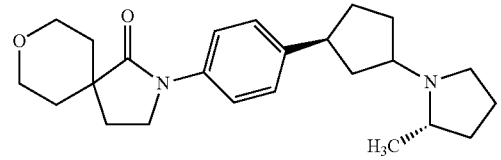 [SMILES: C[C@H]1CCCN1C1CC[C@H](c2ccc(N3CCC4(CCOCC4)C3=O)cc2)C1]

Step 1: 4-[(S)-3-((S)-2-methyl-pyrrolidin-1-yl)-cyclopentyl]-phenylamine (Intermediate 14) was dissolved in DCE (3 mL). To this solution was transferred a solution of 4-(2-oxo-ethyl)-tetrahydro-pyran-4-carboxylic acid methyl ester (Intermediate 1) (53 mg, 0.285 mmol, 1 equiv.) in DCE (1 mL). To this clear solution was then added acetic acid (352 mg, 0.86 mmol, 3.0 equiv), in DCE (1 mL), followed by addition of powder NaBH(OAc)$_3$ (182 mg, 0.86 mmol, 3 equiv.) in one portion under N$_2$ at r.t. The yellowish milky solution was stirred at r.t. for 2 h. TLC (5% 7N NH$_3$ methanol in DCM) indicated that the reaction was complete. LCMS detected product at 0.63 min, MS 415. The reaction was diluted with DCM (10 mL) and quenched with 10 mL NaHCO$_3$. The two layers were separated, and the aqueous layer was extracted with DCM (10 mL×2). The combined DCM extracts were washed with sodium bicarbonate (10 mL), brine (15 mL), dried (anhydrous potassium carbonate), filtered, and concentrated to obtain a compound which was used in the next step.

Step 2: The compound obtained above was dissolved in THF (5 mL). To this solution was added a solution of potassium t-butoxide (1 M in THF) 0.2 mL (0.2 mmol, 1 equiv.) at r.t. The clear solution turned a little bit cloudy. After 5 min, TLC (2.5% of MeOH in DCM) showed the reaction was complete (spot to spot), LC/MS detected the product peak of 444 (t 2.491 min). The reaction mixture was quenched by dilution with EtOAc (20 mL) and water (10 mL). The two layers were separated. The aqueous layer was extracted with EtOAc (2×10 mL). The combined DCM extracts were washed with brine, dried (K$_2$CO$_3$), filtered, and concentrated on rotavap to yield a crude product. This material was dissolved in DCM (1 mL), loaded onto a 10 g of silica gel column eluted with 5% of 7N NH$_3$ solution of MeOH in DCM to afford 60 mg (55% yield over two steps) of the title compound as a waxy solid.

LC: R$_T$=2.21 min, MS (ESI) m/z: 383 (M+H$^+$). $^1$H NMR indicated two sets of signals in approximately 1:1 ratio. No attempt has been made to assign the spectrum unambiguously. Rather, the spectrum was recorded as follows $^1$H NMR (300 MHz, CDCl3) δ: 7.57 (d, 8.7 Hz), 7.24 (d, 8.7 Hz), 4.03 (dt, 4.2 Hz, 11.7 Hz), 3.79 (t, 6.9 Hz), 3.58 (dt, 2.6 Hz, 11.4 Hz), 3.23 (m), 3.01 (m), 2.78 (m), 2.56 (m), 2.23-1.56 (m), 1.46 (m), 1.14 (d, 6.3 Hz), 1.13 (d, 6.3 Hz).

Example 2

2-{4-[(S)-3-((S)-2-Methyl-pyrrolidin-1-yl)-cyclopentyl]-phenyl}-2-aza-spiro[4.5]decan-1-one

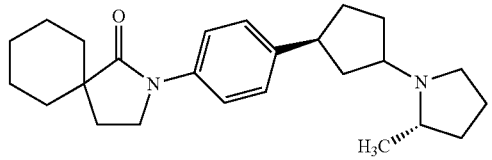 [SMILES: C[C@H]1CCCN1C1CC[C@H](c2ccc(N3CCC4(CCCCC4)C3=O)cc2)C1]

The title compound was synthesized in the manner essentially the same as the Example 1 by condensing 1-(2-oxo-ethyl)-cyclohexanecarboxylic acid methyl ester (Intermediate 6) with 4-[(S)-3-((S)-2-methyl-pyrrolidin-1-yl)-cyclopentyl]-phenylamine (Intermediate 14), and subsequently cyclization.

LC: R$_T$=2.77 min, MS (ESI) m/z: 381 (M+H$^+$).
LC/MS: R$_T$=min. MS (ESI) m/z=(M+H$^+$)

$^1$H NMR indicated two sets of signals in approximately 1:1 ratio. No attempt has been made to assign the spectrum unambiguously. Rather, the spectrum was recorded as follows:

$^1$H NMR (300 MHz, CDCl$_3$) δ: 7.57 (d, 8.7 Hz), 7.23 (d, 8.7 Hz), 3.73 (t, 6.9 Hz), 3.22 (m), 2.99 (m), 2.75 (m), 2.54 (m), 2.07 (m), 1.94 (m), 1.75 (m), 1.51 (m), 1.35 (m), 1.13 (d, 6.3 Hz), 1.12 (d, 6.3 Hz).

Example 3

2-{4-[3-(2-Methyl-pyrrolidin-1-yl)-cyclopentyl]-phenyl}-1-oxo-2,9-diaza-spiro[5.5]undecane-9-carboxylic acid tert-butyl ester

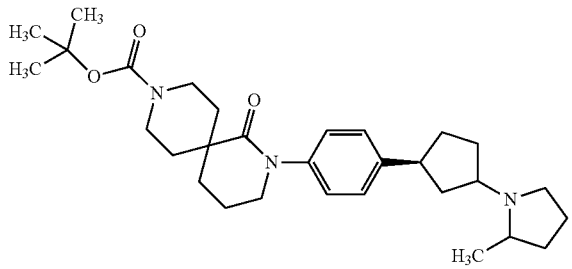 [SMILES: CC1CCCN1C1CC[C@H](c2ccc(N3CCCC4(CCN(C(=O)OC(C)(C)C)CC4)C3=O)cc2)C1]

The title compound was synthesized in the manner essentially the same as the Example 1 by condensing (2-oxo-ethyl)-cyclohexanecarboxylic acid methyl ester (Intermediate 4) with 4-[(S)-3-(2-methyl-pyrrolidin-1-yl)cyclopentyl]-phenylamine (Intermediate 15), and subsequently cyclization.

LC/MS: R$_T$=2.84 min. MS (ESI) m/z=496 (M+H$^+$)

$^1$H NMR indicated two sets of signals. No attempt has been made to assign the spectrum unambiguously. Rather, the spectrum was recorded as follows:

$^1$H NMR (300 MHz, CDCl3) δ: 7.26 (m), 7.11 (m), 3.80 (m), 3.62 (m), 3.29 (m), 3.23 (m), 2.78 (m), 2.53 (m), 2.23-1.63 (m), 1.46 (s), 1.11 (m).

Example 4

8-Hydroxy-2-{4-[3-(2-methyl-pyrrolidin-1-yl)-cyclopentyl]-phenyl}-2-aza-spiro[4.5]decan-1-one

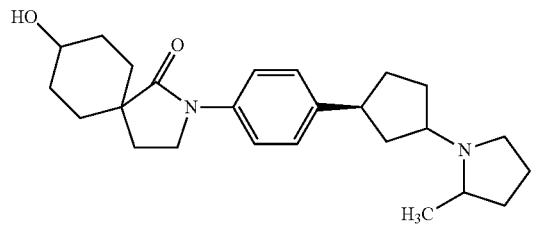 [SMILES: CC1CCCN1C1CC[C@H](c2ccc(N3CCC4(CCC(O)CC4)C3=O)cc2)C1]

The title compound was synthesized in the manner essentially the same as the Example 1 by condensing 4-(tert-butyl-diphenyl-silanyloxy)-1-(2-oxo-ethyl)-cyclohexanecarboxylic acid methyl ester (Intermediate 8) with 4-[(S)-3-(2-methyl-pyrrolidin-1-yl)-cyclopentyl]-phenylamine (Intermediate 15), and subsequently cyclization, followed by de-protection with TBAF in THF at 60° C. for 5 h.

LC: R$_T$=2.31 min, MS (ESI) m/z: 397 (M+H$^+$). $^1$H NMR indicated two sets of signals. No attempt has been made to assign the spectrum unambiguously. Rather, the spectrum was recorded as follows:

$^1$H NMR (300 MHz, CDCl3) δ: 7.55 (m), 7.26 (m), 3.92 (m), 3.76 (m), 3.55 (m), 3.21 (m), 3.00 (m), 2.77 (m), 2.54 (m), 2.17-1.41 (m), 1.13 (d, 6.0 Hz), 1.11 (d, 6.0 Hz).

Example 5

2-{4-[3-(2-Methyl-pyrrolidin-1-yl)-cyclopentyl]-phenyl}-1-oxo-2-aza-spiro[4.5]decane-8-carboxylic acid methyl ester

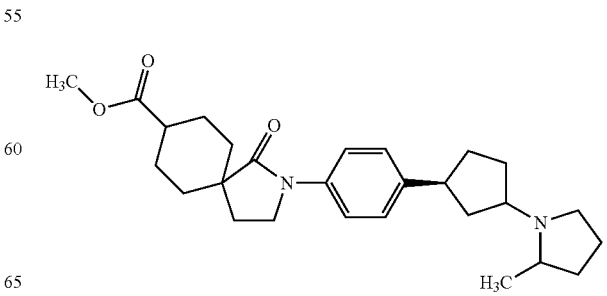

The title compound was synthesized in the manner essentially the same as the Example 1 by condensing 1-(2-oxo-ethyl)-cyclohexane-1,4-dicarboxylic acid dimethyl ester (Intermediate 5) with 4-[(S)-3-(2-methyl-pyrrolidin-1-yl)-cyclopentyl]-phenylamine (Intermediate 15), and subsequently cyclization.

LC/MS: $R_T$=2.72 min. MS (ESI) m/z=439 (M+H$^+$)

$^1$H NMR indicated two sets of signals. No attempt has been made to assign the spectrum unambiguously. Rather, the spectrum was recorded as follows:

$^1$H NMR (300 MHz, CDCl3) δ: 7.55 (m), 7.25 (m), 3.76 (m), 3.74 (m), 3.70 (s), 3.55 (m), 3.21 (m), 3.00 (m), 2.79 (m), 2.53 (m), 2.27 (m), 2.00 (m), 1.74 (m), 1.45 (m), 1.13 (d, 6.0 Hz), 1.11 (d, 6.0 Hz).

Example 6

2-{4-[3-(2-Methyl-pyrrolidin-1-yl)-cyclopentyl]-phenyl}-1-oxo-2,8-diaza-spiro[4.5]decane-8-carboxylic acid tert-butyl ester

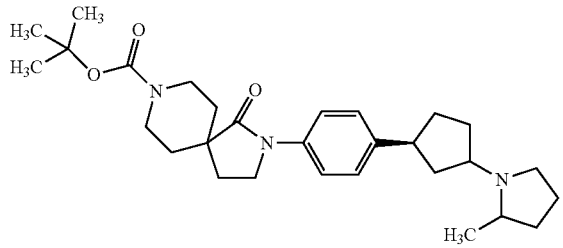 [SMILES: CC1CCCN1C1CC[C@H](c2ccc(N3CCC4(CCN(C(=O)OC(C)(C)C)CC4)C3=O)cc2)C1]

The title compound was synthesized in the manner essentially the same as the Example 1 by condensing 4-(3-oxo-propyl)-piperidine-1,4-dicarboxylic acid 1-tert-butyl ester 4-ethyl ester (Intermediate 4) with 4-[(S)-3-(2-methyl-pyrrolidin-1-yl)-cyclopentyl]-phenylamine (Intermediate 15), and subsequently cyclization.

LC: $R_T$=2.90 min, MS (ESI) m/z: 482 (M+H$^+$). $^1$H NMR indicated two sets of signals. No attempt has been made to assign the spectrum unambiguously. Rather, the spectrum was recorded as follows:

$^1$H NMR (300 MHz, CDCl3) δ: 7.04 (m), 6.64 (m), 4.02 (m), 3.53 (m), 3.08 (m), 2.98 (m), 2.77 (m), 2.53 (m), 2.18-1.62 (m), 1.47 (s), 1.12 (d, 6.0 Hz), 1.11 (d, 6.0 Hz).

Example 7

7-{4-[3-(2-Methyl-pyrrolidin-1-yl)-cyclopentyl]-phenyl}-7-aza-spiro[4.5]decan-6-one

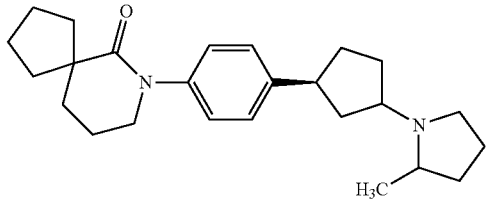 [SMILES: CC1CCCN1C1CC[C@H](c2ccc(N3CCCC4(CCCC4)C3=O)cc2)C1]

The title compound was synthesized in the manner essentially the same as the Example 1 by condensing 1-(3-oxo-propyl)-cyclopentanecarboxylic acid methyl ester (Intermediate 7) with 4-[(S)-3-(2-methyl-pyrrolidin-1-yl)cyclopentyl]-phenylamine (Intermediate 15), and subsequently cyclization.

LC: $R_T$=2.77 min, MS (ESI) m/z: 381 (M+H$^+$).

$^1$H NMR indicated two sets of signals. No attempt has been made to assign the spectrum unambiguously. Rather, the spectrum was recorded as follows:

$^1$H NMR (300 MHz, CDCl3) δ: 7.03 (m), 6.64 (m), 3.63 (m), 3.56 (m), 3.23 (m), 3.03 (m), 2.77 (m), 2.56 (m), 2.22-1.45 (m), 1.13 (d, 6.0 Hz), 1.12 (d, 6.0 Hz).

Example 8

2-{4-[3-(2-Methyl-pyrrolidin-1-yl)-cyclopentyl]-phenyl}-2,9-diaza-spiro[5.5]undecan-1-one hydrochloride

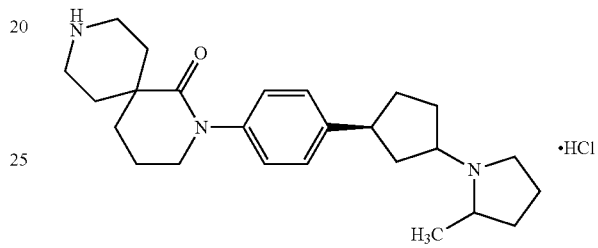

2-{4-[3-(2-Methyl-pyrrolidin-1-yl)-cyclopentyl]-phenyl}-1-oxo-2,8-diaza-spiro[4.5]decane-8-carboxyl ic acid tert-butyl ester (example 3) (22 mg, 0.044 mmol) was treated with 4 M HCl (0.5 mL, 2 mmol, excess) in dioxane and methanol (0.5 mL) at rt for 4 h when TLC (10% MeOH in DCM) showed the reaction was complete. The volatiles were removed in vacuo and the residue was dried under high vacuum for 2 h to obtain 20 mg (100% yield) of the title compound as a gummy solid.

LC/MS: $R_T$=2.27 min. MS (ESI) m/z=396 (M+H$^+$)

Example 9

2-[4-(4-Pyrrolidin-1-yl-cyclohexyl)-phenyl]-8-oxa-2-aza-spiro[4.5]decan-1-one

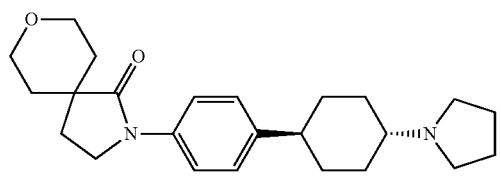 [SMILES: O=C1N(c2ccc([C@H]3CC[C@H](N4CCCC4)CC3)cc2)CCC12CCOCC2]

Cis-Methanesulfonic acid 4-[4-(1-oxo-8-oxa-2-aza-spiro[4.5]dec-2-yl)-phenyl]-cyclohexyl ester (Intermediate 21) (30 mg, 0.07 mmol, 1 equiv.) and pyrrolidine (20 mg, 0.28 mmol, 4 equiv.) were dissolved in anhydrous CH$_3$CN (2 mL). To this colorless solution was added powder K$_2$CO$_3$ at r.t. The suspension was heated in an oil bath maintained at 80° C. for 24 h. The suspension was concentrated to dryness. The residue was taken in water (2 mL) and DCM (2 mL). The two layers were separated, and the aqueous layer was extracted with DCM (2 mL×2). The combined DCM extracts were washed with sodium bicarbonate (2 mL), brine (2 mL), dried (anhydrous potassium carbonate), filtered, and concentrated in vacuo. The crude product was purified on a silica gel column, eluted with 5% of MeOH in DCM and 5% 7N NH₃ of MeOH solution in DCM to obtain the title compound.

LC/MS: $R_T$=2.23 min. MS (ESI) m/z=383 (M+H⁺)

The trans-stereochemistry is confirmed by NMR (2D ROESY) as shown below:

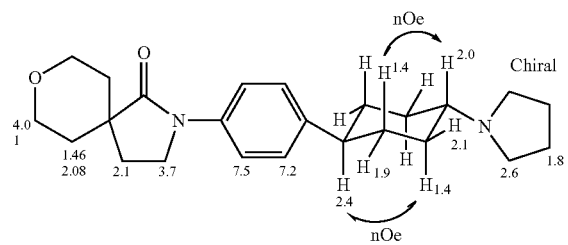 [SMILES: O=C1N(c2ccc(C3CCC(N4CCCC4)CC3)cc2)CCC12CCOCC2]

Example 10

2-{4-[4-((R)-2-Methyl-pyrrolidin-1-yl)-cyclohexyl]-phenyl}-8-oxa-2-aza-spiro[4.5]decan-1-one

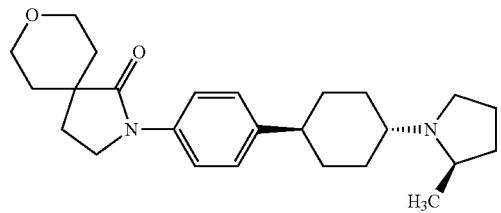 [SMILES: C[C@@H]1CCCN1[C@H]1CC[C@H](c2ccc(N3CCC4(CCOCC4)C3=O)cc2)CC1]

The title compound was synthesized in the manner essentially the same as the Example 9 by condensing cis-methanesulfonic acid 4-[4-(1-oxo-8-oxa-2-aza-spiro[4.5]dec-2-yl)-phenyl]-cyclohexyl ester (Intermediate 21) (30 mg, 0.07 mmol, 1 equiv.) and (R)-2-methylpyrrolidine.

LC/MS: $R_T$=2.33 min. MS (ESI) m/z=397 (M+H⁺)

¹H NMR (300 MHz, CDCl3) δ: 7.57 (d, 8.7 Hz, 2H), 7.23 (d, 8.7 Hz, 2H), 4.03 (bs, 2H), 3.79 (m, 2H), 3.58 (m, 2H), 2.94 (m, 2H), 2.61 (q, 7.8 Hz, 1H), 2.56 (m, 1H), 2.48 (m, 1H), 2.15 (m, 2H), 2.13 (m, 2H), 2.09 (m, 2H), 2.06-1.40 (m, 6H), 1.72 (m, 2H), 1.46 (m, 4H), 1.08 (d, 6.3 Hz, 3H).

Example 11

2-{4-[4-((S)-2-Methyl-piperidin-1-yl)-cyclohexyl]-phenyl}-8-oxa-2-aza-spiro[4.5]decan-1-one

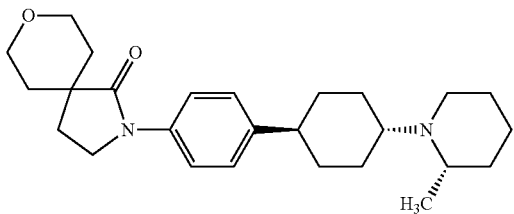 [SMILES: C[C@H]1CCCCN1[C@H]1CC[C@H](c2ccc(N3CCC4(CCOCC4)C3=O)cc2)CC1]

The title compound was synthesized in the manner essentially the same as the Example 9 by condensing cis-methanesulfonic acid 4-[4-(1-oxo-8-oxa-2-aza-spiro[4.5]dec-2-yl)-phenyl]-cyclohexyl ester (Intermediate 21) (30 mg, 0.07 mmol, 1 equiv.) and (S)-2-methyl-piperidine.

LC/MS: $R_T$=2.49 min. MS (ESI) m/z=411 (M+H⁺)

¹H NMR (300 MHz, CDCl3) δ: 7.57 (d, 8.7 Hz, 2H), 7.22 (d, 8.7 Hz, 2H), 4.05 (td, 4.2 Hz, 11.7 Hz, 2H), 3.79 (t, 7.2 Hz, 2H), 3.57 (dt, 2.7 Hz, 11.1 Hz, 2H), 2.91 (m, 2H), 2.62 (q, 7.8 Hz, 1H), 2.44 (m, 3H), 2.15 (m, 2H), 2.13 (m, 2H), 2.06-1.40 (m, 6H), 1.72 (m, 5H), 1.46 (m, 4H), 1.11 (d, 6.3 Hz, 3H).

Example 12

2-{4-[4-((S)-2-Methyl-pyrrolidin-1-yl)-cyclohexyl]-phenyl}-8-oxa-2-aza-spiro[4.5]decan-1-one

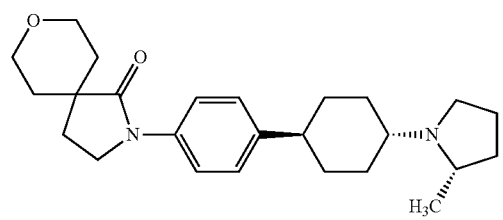 [SMILES: C[C@H]1CCCN1[C@H]1CC[C@H](c2ccc(N3CCC4(CCOCC4)C3=O)cc2)CC1]

The title compound was synthesized in the manner essentially the same as the Example 9 by condensing cis-methanesulfonic acid 4-[4-(1-oxo-8-oxa-2-aza-spiro[4.5]dec-2-yl)-phenyl]-cyclohexyl ester (Intermediate 21) (30 mg, 0.07 mmol, 1 equiv.) and (S)-2-methylpyrrolidine.

LC/MS: $R_T$=2.24 min. MS (ESI) m/z=397 (M+H⁺)

¹H NMR (300 MHz, CDCl3) δ: 7.57 (d, 8.7 Hz, 2H), 7.23 (d, 8.7 Hz, 2H), 4.03 (td, 4.2 Hz, 11.7 Hz, 2H), 3.79 (t, 7.2 Hz, 2H), 3.58 (dt, 2.7 Hz, 11.1 Hz, 2H), 2.94 (m, 2H), 2.61 (q, 7.8 Hz, 1H), 2.56 (m, 1H), 2.48 (m, 1H), 2.15 (t, 7.2 Hz, 2H), 2.13 (m, 2H), 2.09 (m, 2H), 2.06-1.40 (m, 6H), 1.72 (m, 2H), 1.46 (m, 4H), 1.08 (d, 6.3 Hz, 3H).

Example 13

2-[2-Fluoro-4-(4-pyrrolidin-1-yl-cyclohexyl)-phenyl]-1-oxo-2,8-diaza-spiro[4.5]decane-8-carboxylic acid tert-butyl ester

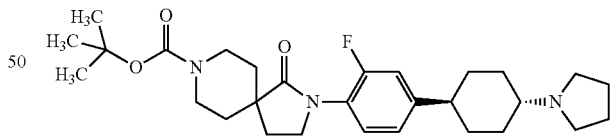

2-[2-Fluoro-4-(4-methanesulfonyloxy-cyclohexyl)-phenyl]-1-oxo-2,8-diaza-spiro[4.5]decane-8-carboxylic acid tert-butyl ester (Intermediate 28) (150 mg, 0.3 mmol, 1 equiv.) and pyrrolidine (84.3 mg, 1.19 mmol) were dissolved in anhydrous CH₃CN (2 mL). To this colorless solution was added powder K₂CO₃ at r.t. The suspension was heated in an oil bath maintained at 80° C. for 24 h. The suspension was concentrated to dryness. The residue was taken in water (2 mL) and DCM (2 mL). The two layers were separated, and the aqueous layer was extracted with DCM (2 mL×2). The combined DCM extracts were washed with sodium bicarbonate (2 mL), brine (2 mL), dried (anhydrous potassium carbonate), filtered, and concentrated in vacuo. The crude product was purified on a silica gel column, eluted with 5% of MeOH in DCM and 5% 7N NH$_3$ of MeOH solution in DCM to afford the title compound.

LC/MS: R$_T$=2.92 min. MS (ESI) m/z=500 (M+H$^+$)

The trans-stereochemistry is confirmed by NMR (2D ROESY) as shown below:

Example 14

2-{2-Fluoro-4-[4-((R)-2-methyl-pyrrolidin-1-yl)-cyclohexyl]-phenyl}-1-oxo-2,8-diaza-spiro[4.5]decane-8-carboxylic acid tert-butyl ester The title compound was synthesized in the same manner as Example 13 by condensing 2-[2-fluoro-4-(4-methanesulfonyloxy-cyclohexyl)-phenyl]-1-oxo-2,8-diaza-spiro[4.5]decane-8-carboxylic acid tert-butyl ester (Intermediate 28) (150 mg, 0.3 mmol, 1 equiv.) with (R)-2-methyl-pyrrolidine (101.2 mg, 1.19 mmol) to obtain 45 mg (67% yield) of the compound.

LC/MS: R$_T$=2.95 min. MS (ESI) m/z=514 (M+H$^+$)

$^1$H NMR (300 MHz, CDCl3) δ: 7.28 (m, 1H), 7.01 (m, 2H), 4.01 (m, 2H), 3.74 (t, 6.9 Hz, 2H), 3.10 (m, 2H), 2.97 (m, 2H), 2.61 (m, 2H), 2.49 (m, 1H), 2.12 (t, 6.9 Hz, 4H), 1.95 (m, 6H), 1.60 (m, 8H), 1.47 (s, 9H), 1.09 (d, 6.3 Hz, 3H).

Example 15

2-[4-(4-Azetidin-1-yl-cyclohexyl)-2-fluoro-phenyl]-1-oxo-2,8-diaza-spiro[4.5]decane-8-carboxylic acid tert-butyl ester The title compound was synthesized in the same manner as Example 13 by condensing 2-[2-fluoro-4-(4-methanesulfonyloxy-cyclohexyl)-phenyl]-1-oxo-2,8-diaza-spiro[4.5]decane-8-carboxylic acid tert-butyl ester (Intermediate 28) (150 mg, 0.3 mmol, 1 equiv.) with azetidine (67.8 mg, 1.19 mmol) to obtain 55 mg (85% yield) of the compound.

LC/MS: R$_T$=2.84 min. MS (ESI) m/z=486 (M+H$^+$)

$^1$H NMR (300 MHz, CDCl3) δ: 7.28 (m, 1H), 6.98 (m, 2H), 3.99 (m, 2H), 3.74 (t, 6.9 Hz, 2H), 3.20 (d, 6.9 Hz, 4H), 3.10 (m, 2H), 2.46 (m, 1H), 2.08 (m, 4H), 1.91 (m, 5H), 1.77 (bs, 2H), 1.49 (m, 4H), 1.47 (s, 9H), 1.12 (m, 2H).

Example 16

2-{2-Fluoro-4-[4-((S)-2-methyl-pyrrolidin-1-yl)-cyclohexyl]-phenyl}-1-oxo-2,8-diaza-spiro[4.5]decane-8-carboxylic acid tert-butyl ester The title compound was synthesized in the same manner as Example 13 by condensing 2-[2-fluoro-4-(4-methanesulfonyloxy-cyclohexyl)-phenyl]-1-oxo-2,8-diaza-spiro[4.5]decane-8-carboxylic acid tert-butyl ester (Intermediate 28) (150 mg, 0.3 mmol, 1 equiv.) with (S)-2-methyl-pyrrolidine (101.2 mg, 1.19 mmol) to obtain 67 mg (88% yield) of the compound.

LC/MS: LC R$_T$=2.96 min. MS (ESI) m/z=514 (M+H$^+$)

$^1$H NMR (300 MHz, CDCl3) δ: 7.28 (m, 1H), 7.01 (m, 2H), 4.01 (m, 2H), 3.74 (m, 2H), 3.10 (m, 2H), 2.97 (m, 2H), 2.61 (m, 2H), 2.49 (m, 1H), 2.13 (m, 4H), 1.95 (m, 6H), 1.62 (m, 8H), 1.47 (s, 9H), 1.09 (d, 6.3 Hz, 3H).

Example 17

2-{2-Fluoro-4-[4-((S)-2-methyl-pyrrolidin-1-yl)-cyclohexyl]-phenyl}-2,8-diaza-spiro[4.5]decan-1-one hydrochloride 2-{2-Fluoro-4-[4-((S)-2-methyl-pyrrolidin-1-yl)-cyclohexyl]-phenyl}-1-oxo-2,8-diaza-spiro[4.5]decane-8-carboxylic acid tert-butyl ester was dissolved in 0.5 mL of methanol and cooled to ice-water bath. To this solution was added 0.5 mL of 4M HCl in dioxane (excess). The clear solution was stirred at r.t. overnight. The solvent was evaporated and the residue was further dried under reduced pressure to obtain the title compound as a gummy semi-solid.

LC/MS: LC R$_T$=2.11 min. MS (ESI) m/z=414 (M+H$^+$)

$^1$H NMR (300 MHz, DMSO-d6) δ: 9.89 (bs, 1H), 8.82 (bs, 1H), 8.59 (bs, 1H), 7.36 (m, 1H), 7.17 (m, 2H), 3.70 (m, 3H), 3.41 (m, 2H), 3.05 (m, 2H), 2.44 (m, 3H), 2.16 (m, 6H), 1.92 (m, 6H), 1.72 (m, 3H), 1.59 (m, 4H), 1.39 (d, 6.6 Hz, 3H).

Example 18

2-{2-Fluoro-4-[4-((R)-2-methyl-pyrrolidin-1-yl)-cyclohexyl]-phenyl}-2,8-diaza-spiro[4.5]decan-1-one hydrochloride

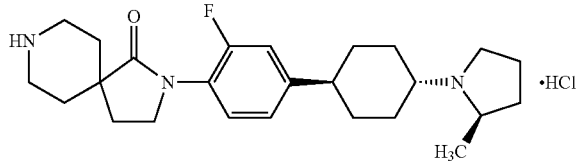

The title compound was prepared in the same manner as Example 17 by using hydrochloric acid in dioxane to hydrolyze 2-{2-fluoro-4-[4-((R)-2-methyl-pyrrolidin-1-yl)-cyclohexyl]-phenyl}-1-oxo-2,8-diaza-spiro[4.5]decane-8-carboxylic acid tert-butyl ester.

LC/MS: LC $R_T$=2.08 min. MS (ESI) m/z=414 (M+H$^+$)

$^1$H NMR (300 MHz, DMSO-d6) δ: 10.01 (bs, 1H), 8.88 (bs, 1H), 8.63 (bs, 1H), 7.37 (m, 1H), 7.15 (m, 2H), 3.72 (d, 6.6 Hz, 3H), 3.40 (m, 2H), 3.05 (m, 2H), 2.57 (m, 3H), 2.16 (d, 6.6 Hz, 6H), 1.92 (m, 6H), 1.70 (m, 3H), 1.61 (m, 4H), 1.40 (d, 6.6 Hz, 3H).

Example 19

2-[4-(4-Azetidin-1-yl-cyclohexyl)-2-fluoro-phenyl]-2,8-diaza-spiro[4.5]decan-1-one hydrochloride

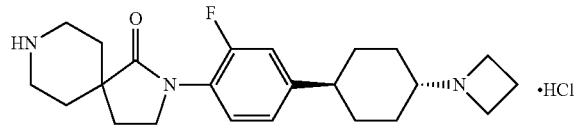 [SMILES: O=C1N(c2ccc([C@H]3CC[C@H](N4CCC4)CC3)cc2F)CCC12CCNCC2 ; Cl]

The title compound was prepared in the same manner as Example 17 by using hydrochloric acid in dioxane to hydrolyze 2-[4-(4-azetidin-1-yl-cyclohexyl)-2-fluoro-phenyl]-1-oxo-2,8-diaza-spiro[4.5]decane-8-carboxylic acid tert-butyl ester LC/MS: LC $R_T$=1.87 min. MS (ESI) m/z=386 (M+H$^+$)

$^1$H NMR (300 MHz, DMSO-d6) δ: 10.73 (bs, 1H), 8.85 (bs, 1H), 8.63 (bs, 1H), 7.37 (m, 1H), 7.17 (m, 2H), 4.03 (m, 4H), 3.69 (t, 6.6 Hz, 3H), 3.14 (m, 1H), 3.04 (m, 2H), 2.44 (m, 2H), 2.17 (m, 3H), 2.00 (m, 3H), 1.91 (m, 3H), 1.72 (m, 2H), 1.39 (m, 4H).

Example 20

2-[2-Fluoro-4-(4-pyrrolidin-1-yl-cyclohexyl)-phenyl]-2,8-diaza-spiro[4.5]decan-1-one hydrochloride

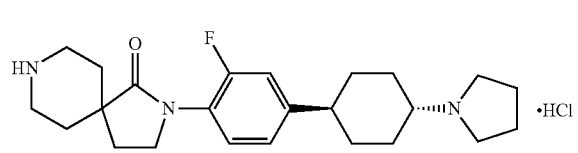 [SMILES: O=C1N(c2ccc([C@H]3CC[C@H](N4CCCC4)CC3)cc2F)CCC12CCNCC2 ; Cl]

The title compound was prepared in the same manner as Example 17 by using hydrochloric acid in dioxane to hydrolyze 2-[2-fluoro-4-(4-pyrrolidin-1-yl-cyclohexyl)-phenyl]-1-oxo-2,8-diaza-spiro[4.5]decane-8-carboxylic acid tert-butyl ester.

LC $R_T$=2.07 min, MS (ESI) m/z: 400;

$^1$H NMR (300 MHz, DMSO-d6) δ: 10.32 (bs, 1H), 8.74 (bs, 1H), 8.54 (bs, 1H), 7.36 (m, 1H), 7.15 (m, 2H), 3.70 (t, 6.6 Hz, 3H), 3.50 (m, 2H), 3.05 (m, 4H), 2.44 (m, 3H), 2.17 (m, 6H), 1.94 (m, 6H), 1.72 (m, 3H), 1.55 (m, 4H).

Example 21

{2-Fluoro-4-[4-((S)-2-methyl-pyrrolidin-1-yl)-cyclohex-1-enyl]-phenyl}-carbamic acid benzyl ester

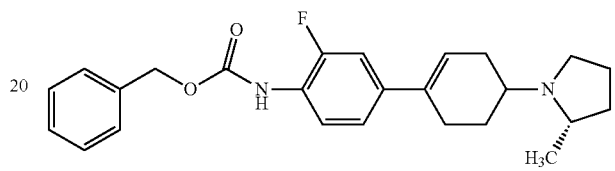

Methanesulfonic acid 4-(4-benzyloxycarbonylamino-3-fluoro-phenyl)-cyclohex-3-enyl ester (200 mg, 0.47 mmol, 1 equiv.) was dissolved in 5 mL of anhydrous acetonitrile. This solution was transferred into a flask containing (S)-2-methyl-pyrrolidine (159 mg, 1.88 mmol, 4 equiv.) and K$_2$CO$_3$ (285 mg, 2.07 mmol, 4.4 equiv.). The suspension was de-aerated by vacuum/nitrogen exchange 3 times, and then, heated on an oil bath set at 80° C. externally with stirring under nitrogen for 16 h. TLC (5% MeOH in DCM for SM) showed the reaction is complete. Acetonitrile was removed in vacuo. The residue was taken in water (5 mL) and DCM (10 mL). The two layers were separated and the aqueous layer was extracted with DCM (2×10 mL). The combined extracts were washed with NaHCO$_3$ aq. (5 mL), brine (5 mL) and dried (K$_2$CO$_3$). The solution was filtered. The filtrate was concentrated in vacuo to obtain a crude product. The crude product was purified on a silica gel column, eluted with DCM, followed by 5% MeOH in DCM and 5% of 7N NH$_3$-MeOH in DCM. The combined fractions containing the product were concentrated to yield the title compound.

LC $R_T$=2.9 min, MS (ESI) m/z: 409; $^1$H NMR in CDCl$_3$ showed two sets of signals. No attempt has been made to assign the spectrum unambiguously. Rather, the spectrum was recorded as follows:

$^1$H NMR (300 MHz, CDCl$_3$) δ: 8.03 (m,), 7.42 (m), 7.14-7.04 (m), 6.89 (s), 6.04 (bs), 5.22 (s), 4.11 (bs), 3.39 (m), 3.08 (m), 2.77 (m), 2.51 (m), 2.38 (m), 2.03 (m), 1.79 (m), 1.64 (m), 1.28 (m), 1.23 (d, 6.0 Hz), 1.19 (d, 6.0 Hz).

Example 22

1-Acetyl-piperidine-4-carboxylic acid {4-[(S)-3-((S)-2-methyl-pyrrolidin-1-yl)-cyclopentyl]-phenyl}-amide

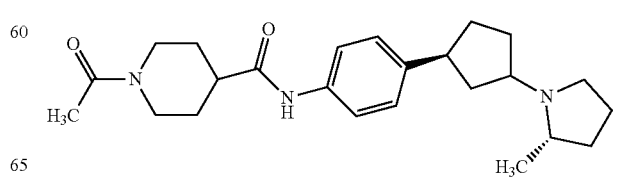

4-[(S)-3-((S)-2-Methyl-pyrrolidin-1-yl)-cyclopentyl]-phenylamine (Intermediate 14) was dissolved in DCE (1 mL). To this solution was transferred a solution of 1-acetyl-piperidine-4-carboxylic acid chloride in DCE (1 mL), followed by pyridine (0.5 mL). The solution was stirred at r.t. for 2 h when TLC (5% of 7N NH$_3$ MeOH in DCM) and LC/MS showed that the reaction was complete. The reaction was quenched with polymer bound diethylenetriamine (4 mmol/g) (0.1 g) and the suspension was stirred for 30 min. Then, 10 mL of DCM was added to the suspension and the suspension was filtered through a celite pad, rinsed with DCM and 10% MeOH in DCM. The crude product was purified on a silica gel column eluted with 5% of 7N NH$_3$ MeOH in DCM to obtain 15.9 mg (63%) of the title compound as a gummy solid.

LC R$_T$=2.06 min, MS (ESI) m/z: 398; $^1$H NMR in CDCl3 showed two sets of signals. No attempt has been made to assign the spectrum unambiguously. Rather, the spectrum was recorded as follows:

$^1$H NMR (300 MHz, CDCl3) δ: 8.03 (m,), 7.41 (m), 7.19 (m), 4.73 (s), 4.62 (m), 3.90 (m), 3.17 (m), 2.98 (m), 2.73 (m), 2.03 (m), 2.51 (m), 2.11 (s), 2.08-1.56 (m), 1.45 (m), 1.12 (d, 6.3 Hz), 1.10 (d, 6.3 Hz).

Example 23

Thiophene-2-carboxylic acid {4-[(S)-3-((S)-2-methyl-pyrrolidin-1-yl)-cyclopentyl]-phenyl}-amide

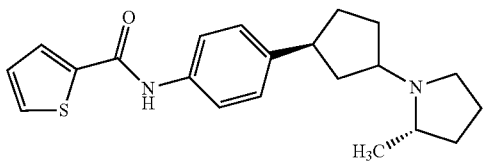 [SMILES: C[C@H]1CCCN1C1CC[C@H](c2ccc(NC(=O)c3cccs3)cc2)C1]

The procedures as set forth in Example 22 were substantially repeated by employing the appropriate starting materials and reagents to obtain 14.2 mg (71%) of the title compound as a gummy solid.

LC R$_T$=2.40 min, MS (ESI) m/z: 355; $^1$H NMR in CDCl$_3$ showed two sets of signals. No attempt has been made to assign the spectrum unambiguously. Rather, the spectrum was recorded as follows:

$^1$H NMR (300 MHz, CDCl3) δ: 7.59 (m), 7.20 (m), 3.37 (m), 3.24 (m), 3.02 (m), 2.75 (m), 2.27 (m), 2.02 (m), 1.80 (m), 1.58 (m), 1.28 (d, 6.3 Hz), 1.22 (d, 6.3 Hz).

Example 24

4-Fluoro-N-{4-[(S)-3-((S)-2-methyl-pyrrolidin-1-yl)-cyclopentyl]-phenyl}-benzenesulfonamide

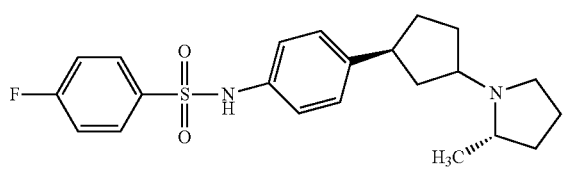

The procedures as set forth in Example 22 were substantially repeated by employing the appropriate starting materials and reagents to obtain 16.1 mg of the title compound (62% yield).

LC R$_T$=2.57 min, MS (ESI) m/z: 403; $^1$H NMR in CDCl$_3$ showed two sets of signals. No attempt has been made to assign the spectrum unambiguously. Rather, the spectrum was recorded as follows:

$^1$H NMR (300 MHz, CDCl$_3$) δ: 7.76-6.97 (m), 4.73 (bs), 3.19 (m), 2.99 (m), 2.76 (m), 2.54 (m), 2.19-1.60 (m), 1.50 (m), 1.26 (d, 6.3 Hz), 1.10 (d, 6.3 Hz).

Example 25

5-Fluoro-2-methyl-N-{4-[(S)-3-((S)-2-methyl-pyrrolidin-1-yl)-cyclopentyl]-phenyl}-benzamide

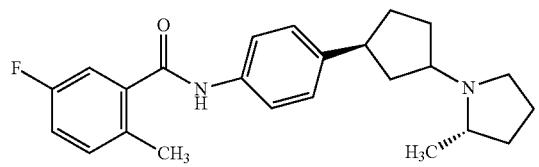 [SMILES: Cc1ccc(F)cc1C(=O)Nc1ccc([C@H]2CCC(N3CCC[C@@H]3C)C2)cc1]

The procedures as set forth in Example 22 were substantially repeated by employing the appropriate starting materials and reagents to obtain 15.2 mg of the title compound (66% yield).

LC R$_T$=2.62 min, MS (ESI) m/z: 381; $^1$H NMR in CDCl$_3$ showed two sets of signals. No attempt has been made to assign the spectrum unambiguously. Rather, the spectrum was recorded as follows:

$^1$H NMR (300 MHz, CDCl$_3$) δ: 7.52 (m), 7.26-7.04 (m), 4.74 (s), 3.35-2.84 (m), 2.68 (m), 2.51 (s), 2.44 (s), 2.29-1.71 (m), 1.55 (m), 1.25 (d, 6.3 Hz), 1.19 (d, 6.3 Hz).

Example 26

3,5-Dimethyl-isoxazole-4-carboxylic acid {4-[(S)-3-((S)-2-methyl-pyrrolidin-1-yl)-cyclopentyl]-phenyl}-amide

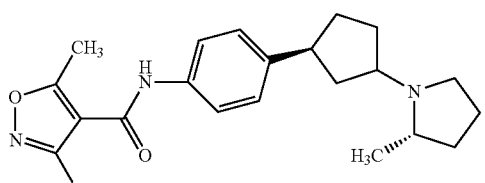

The procedures as set forth in Example 22 were substantially repeated by employing the appropriate starting materials and reagents to obtain 14.7 mg of the title compound (68% yield).

LC R$_T$=2.82 min, MS (ESI) m/z: 368; $^1$H NMR in CDCl3 showed two sets of signals in approximately 1:3 ratio. No attempt has been made to assign the spectrum unambiguously. Rather, the spectrum was recorded as follows:

$^1$H NMR (300 MHz, CDCl3) δ: 7.47 (d, 8.7 Hz), 7.46 (d, 8.7 Hz), 7.26 (d, 8.7 Hz), 7.23 (d, 8.7 Hz), 3.79-7.08

(m), 2.65 (s), 2.63 (s), 2.48 (s), 2.44 (s), 2.31-2.12 (m), 2.08-1.71 (m), 1.64-1.51 (m), 1.25 (d, 6.3 Hz), 1.20 (d, 6.3 Hz).

Example 27

Cyclopropanesulfonic acid {4-[(S)-3-((S)-2-methyl-pyrrolidin-1-yl)cyclopentyl]-phenyl}-amide

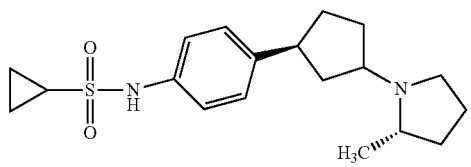 [SMILES: C[C@H]1CCCN1C1CC[C@H](c2ccc(NS(=O)(=O)C3CC3)cc2)C1]

The procedures as set forth in Example 22 were substantially repeated by employing the appropriate starting materials and reagents to obtain 13.9 mg of the title compound (72% yield).

LC $R_T$=2.20 min, MS (ESI) m/z: 349; $^1$H NMR in CDCl$_3$ showed two sets of signals. No attempt has been made to assign the spectrum unambiguously. Rather, the spectrum was recorded as follows:

$^1$H NMR (300 MHz, CDCl3) δ: 7.22-6.65 (m), 3.56 (m), 3.20 (m), 3.00 (m), 2.75 (m), 2.52 (m), 2.18-1.56 (m), 1.46 (m), 1.26 (m), 1.11 (d, 6.3 Hz), 0.95 (d, 6.3 Hz).

Example 28

Tetrahydro-pyran-4-carboxylic acid {4-[(S)-3-((S)-2-methyl-pyrrolidin-1-yl)-cyclopentyl]-phenyl}-amide

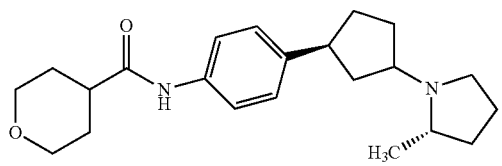 [SMILES: C[C@H]1CCCN1C1CC[C@H](c2ccc(NC(=O)C3CCOCC3)cc2)C1]

4-[(S)-3-((S)-2-Methyl-pyrrolidin-1-yl)-cyclopentyl]-phenylamine (Intermediate 14) (40 mg, 0.16 mmol) was dissolved in DCM (2 mL). To this solution was transferred a solution of tetrahydro-pyran-4-carboxylic acid chloride (71.3 mg, 0.5 mmol, 3.0 equiv.) in DCM (1 mL), followed by pyridine (0.5 mL). The solution was stirred at r.t. for 2 h when TLC (5% of 7N NH$_3$ MeOH in DCM) and LC/MS showed that the reaction was complete. The reaction was quenched by addition of polymer bound diethylenetriamine (4 mmol/g) (0.1 g) and the suspension was stirred for 30 min. Then, 10 mL of DCM was added to the suspension and the suspension was filtered through a celite pad, rinsed with DCM and 10% MeOH in DCM. The crude product was purified on a silica gel column eluted with 5% of 7N NH$_3$ MeOH in DCM to obtain 50 mg (87% yield) of the title compound.

LC $R_T$=2.52 min, MS (ESI) m/z: 357. $^1$H NMR in CDCl$_3$ showed two sets of signals. No attempt has been made to assign the spectrum unambiguously. Rather, the spectrum was recorded as follows:

$^1$H NMR (300 MHz, CDCl3) δ: 7.51-7.09 (m), 4.06 (m), 4.03 (m), 3.99 (m), 3.95 (m), 3.66 (m), 3.55 (m), 3.44 (m, 3.21 (m), 3.01 (m), 2.54 (m), 2.36-1.67 (m), 1.49 (d, 6.3 Hz), 1.26 (d, 6.3 Hz).

Example 29

N-{4-[(S)-3-((S)-2-Methyl-pyrrolidin-1-yl)-cyclopentyl]-phenyl}-benzamide

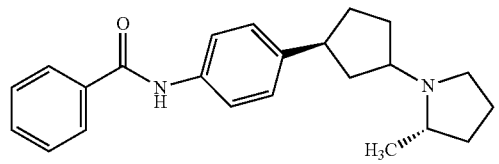 [SMILES: C[C@H]1CCCN1C1CC[C@H](c2ccc(NC(=O)c3ccccc3)cc2)C1]

The title compound was synthesized essentially in the same manner as Example 28 by employing 4-[(S)-3-((S)-2-methyl-pyrrolidin-1-yl)-cyclopentyl]-phenylamine (Intermediate 14) and benzoyl chloride.

LC $R_T$=2.85 min, MS (ESI) m/z: 349. $^1$H NMR in CDCl$_3$ showed two sets of signals. No attempt has been made to assign the spectrum unambiguously. Rather, the spectrum was recorded as follows:

$^1$H NMR (300 MHz, CDCl$_3$) δ: 7.96-7.19 (m), 3.46 (m), 3.32 (m), 2.88 (m), 2.39 (m), 2.22-1.82 (m), 1.65 (m), 1.31 (d, 6.3 Hz), 1.26 (d, 6.3 Hz).

Example 30

3,4-Difluoro-N-{4-[(S)-3-((S)-2-methyl-pyrrolidin-1-yl)-cyclopentyl]-phenyl}-benzenesulfonamide

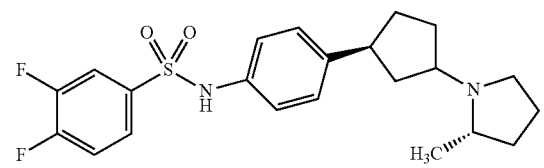 [SMILES: C[C@H]1CCCN1C1CC[C@H](c2ccc(NS(=O)(=O)c3ccc(F)c(F)c3)cc2)C1]

The title compound was synthesized essentially in the same manner as Example 28 by employing 4-[(S)-3-((S)-2-methyl-pyrrolidin-1-yl)-cyclopentyl]-phenylamine (Intermediate 14) and 3,4-difluorobenzene sulfonyl chloride.

LC $R_T$=2.99 min, MS (ESI) m/z: 421. $^1$H NMR in CDCl$_3$ showed two sets of signals. No attempt has been made to assign the spectrum unambiguously. Rather, the spectrum was recorded as follows:

¹H NMR (300 MHz, CDCl3) δ: 7.72-7.51 (m), 7.29-6.98 (m), 3.41 (m), 3.24 (m), 2.97 (m), 2.84 (m), 2.31 (m), 2.06-1.88 (m), 1.62 (m), 1.28 (d, 6.0 Hz), 1.26 (d, 6.0 Hz).

Example 31

4-Fluoro-N-{4-[(S)-3-((S)-2-methyl-pyrrolidin-1-yl)-cyclopentyl]-phenyl}-benzamide

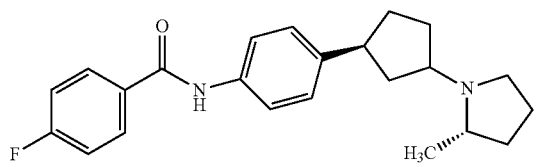 [SMILES: C[C@H]1CCCN1C1CC[C@H](c2ccc(NC(=O)c3ccc(F)cc3)cc2)C1]

The title compound was synthesized essentially in the same manner as Example 28 by employing 4-[(S)-3-((S)-2-methyl-pyrrolidin-1-yl)-cyclopentyl]-phenylamine (Intermediate 14) and 4-fluorobenzoyl chloride.

LC $R_T$=2.93 min, MS (ESI) m/z: 367. ¹H NMR in CDCl$_3$ showed two sets of signals. No attempt has been made to assign the spectrum unambiguously. Rather, the spectrum was recorded as follows:

¹H NMR (300 MHz, CDCl$_3$) δ: 7.97-7.11 (m), 3.43 (m), 3.28 (m), 2.83 (m), 2.33 (m), 2.19-1.80 (m), 1.62 (m), 1.28 (d, 6.3 Hz), 1.27 (d, 6.3 Hz).

Example 32

4-Chloro-N-{4-[(S)-3-((S)-2-methyl-pyrrolidin-1-yl)-cyclopentyl]-phenyl}-benzamide

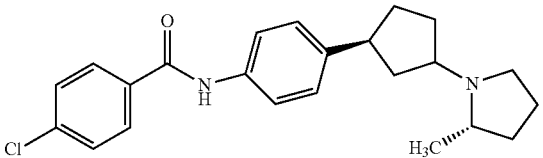 [SMILES: C[C@H]1CCCN1C1CC[C@H](c2ccc(NC(=O)c3ccc(Cl)cc3)cc2)C1]

The title compound was synthesized essentially in the same manner as Example 28 by employing 4-[(S)-3-((S)-2-methyl-pyrrolidin-1-yl)-cyclopentyl]-phenylamine (Intermediate 14) and 4-chlorobenzoyl chloride.

LC $R_T$=3.06 min, MS (ESI) m/z: 383.

Example 33

2-Methyl-N-{4-[(S)-3-((S)-2-methyl-pyrrolidin-1-yl)-cyclopentyl]-phenyl}-benzamide

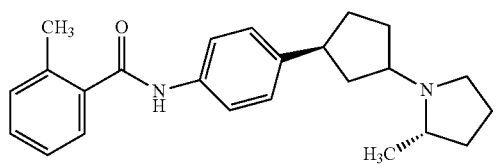 [SMILES: Cc1ccccc1C(=O)Nc1ccc([C@H]2CCC(N3CCC[C@@H]3C)C2)cc1]

The title compound was synthesized essentially in the same manner as Example 28 by employing 4-[(S)-3-((S)-2-methyl-pyrrolidin-1-yl)-cyclopentyl]-phenylamine (Intermediate 14) and 2-methylbenzoyl chloride.

LC $R_T$=3.84 min, MS (ESI) m/z: 363. ¹H NMR in CDCl$_3$ showed two sets of signals. No attempt has been made to assign the spectrum unambiguously. Rather, the spectrum was recorded as follows:

¹H NMR (300 MHz, CDCl$_3$) δ: 7.51-7.13 (m), 3.64-3.34 (m), 3.10 (m), 2.50 (s), 2.11 (m), 1.79 (m), 1.67 (m), 1.41 (d, 6.3 Hz), 1.26 (d, 6.3 Hz).

Example 34

4-Methyl-N-{4-[(S)-3-((S)-2-methyl-pyrrolidin-1-yl)-cyclopentyl]-phenyl}-benzamide

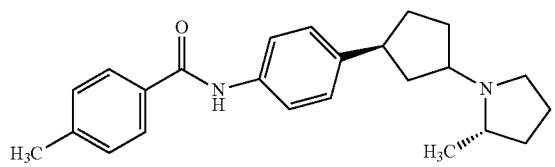 [SMILES: Cc1ccc(C(=O)Nc2ccc([C@H]3CCC(N4CCC[C@@H]4C)C3)cc2)cc1]

The title compound was synthesized essentially in the same manner as Example 28 by employing 4-[(S)-3-((S)-2-methyl-pyrrolidin-1-yl)cyclopentyl]-phenylamine (Intermediate 14) and 4-methylbenzoyl chloride.

LC $R_T$=3.01 min, MS (ESI) m/z: 363.

Example 35

N-{4-[(S)-3-((S)-2-Methyl-pyrrolidin-1-yl)-cyclopentyl]-phenyl}-2-trifluoromethoxy-benzamide

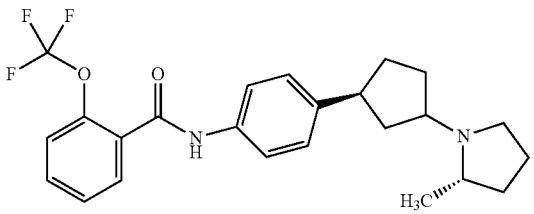 [SMILES: C[C@H]1CCCN1C1CC[C@H](c2ccc(NC(=O)c3ccccc3OC(F)(F)F)cc2)C1]

The title compound was synthesized essentially in the same manner as Example 28 by employing 4-[(S)-3-((S)-2-methyl-pyrrolidin-1-yl)-cyclopentyl]-phenylamine (Intermediate 14) and 2-trifluoromethoxybenzoyl chloride.

LC $R_T$=3.04 min, MS (ESI) m/z: 433.

Example 36

N-{4-[(S)-3-((S)-2-Methyl-pyrrolidin-1-yl)-cyclopentyl]-phenyl}-4-trifluoromethoxy-benzamide

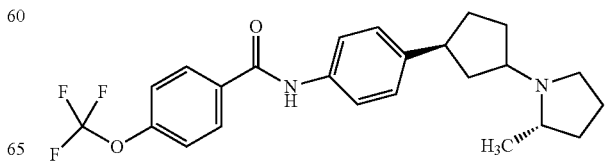

The title compound was synthesized essentially in the same manner as Example 28 by employing 4-[(S)-3-((S)-2-methyl-pyrrolidin-1-yl)-cyclopentyl]-phenylamine (Intermediate 14) and 4-trifluoromethoxybenzoyl chloride.

LC $R_T$=3.25 min, MS (ESI) m/z: 433

Example 37

N-{4-[(S)-3-((S)-2-Methyl-pyrrolidin-1-yl)-cyclopentyl]-phenyl}-2-phenyl-acetamide

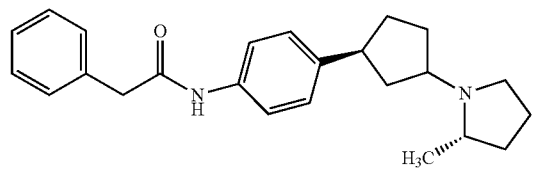 [SMILES: C[C@H]1CCCN1C1CC[C@H](c2ccc(NC(=O)Cc3ccccc3)cc2)C1]

The title compound was synthesized essentially in the same manner as Example 28 by employing 4-[(S)-3-((S)-2-methyl-pyrrolidin-1-yl)-cyclopentyl]-phenylamine (Intermediate 14) and phenacetyl chloride.

LC $R_T$=2.89 min, MS (ESI) m/z: 363.

Biological Examples

Example 38

This example demonstrates the efficacy of compounds of this invention as H3 receptor ligands. The compounds of this invention have been demonstrated to displace [$^3$H]-Methylhistamine radioligand binding to mammalian cell membranes expressing rhesus (*Macacca Mulatta*) H3 receptor. Additionally, the compounds of this invention can also be tested by GTPγS radioligand binding assay to inhibit rhesus H3 constitutive functional activity in cell membranes. This inhibition of basal rhesus H3-mediated GTPγS radioligand binding would demonstrate that the compounds of this invention will find utility as inverse agonists. These compounds are believed to decrease rhesus H3 GTPγS radioligand binding by 0-40% below basal levels.

Rhesus H3 membranes were prepared from the Flp-In T-REx 293 Cell Line (Invitrogen) stably transfected with pcDNA5/FRT/TO (Invitrogen) containing the rhesus monkey (*Macacca Mulatta*) 445 amino acid H3 receptor. (Genbank #AY231164). Stably transfected cultures were amplified in tissue culture flasks by standard tissue culture methods and induced to express rhesus H3 by exposure to 500 ng/ml tetracycline (Cellgro) for 24 hours. After induction, cells were dissociated from flasks utilizing Cell Stripper (Cellgro). Cells were centrifuged (1K×g, 5 min) and pellet frozen in an ethanol-dry ice bath to disrupt cell membranes. Frozen cell pellet was re-suspended in 5 mM HEPES (pH 7.4, Invitrogen) at 10 ml/1000 cm2 of harvested cells. The cell suspension was drawn through an 18 gauge needle (2-3×) followed by a 23 gauge needle (2-3×) to further disrupt cell membranes. The cell suspension was centrifuged (40K×g, 30 min). Cell membrane pellet was re-suspended in 5 mM HEPES (pH 7.4, Invitrogen) at a final protein concentration of 10 mg/ml. Rhesus H3 membranes were stored under liquid nitrogen prior to use in [$^3$H]-Methylhistamine and GTPγS radioligand binding assays.

Rhesus H3 radioligand binding assay was performed using rhesus H3 receptor membranes (prepared as described above), [3H]-Methylhistamine (Perkin Elmer) and WGA SPA beads (wheat germ agglutinin scintillation proximity assay) beads (Amersham). The assay was performed in 96-well Opti-Plates (Packard). Each reaction contained 50 μl rhesus H3 membranes (20-30 μg total protein), 50 μl WGA SPA beads (0.1 μg) and 50 μl of 83 Ci/mmol [$^3$H]-Methylhistamine (final concentration 2 nM) and 50 μl of tested compound. The compounds of this invention and/or vehicle were diluted with binding buffer from 10 mM DMSO stocks. Assay plates were sealed with TopSeal (Perkin Elmer) and mixed on shaker (25° C., 1 hour). Assay plates were read on TopCount scintillation counter (Packard). Results were analyzed by Hill transformation and Ki values were determined by Cheng-Prusoff equation. The observed binding data for the compounds of this invention including a few of the intermediates as noted are summarized in Table 1.

TABLE 1

| Ex. No. | Rhesus H3 Binding ki (M) |
|---|---|
| 1 | 1.19E−08 |
| 2 | 1.28E−08 |
| 3 | 1.79E−08 |
| 4 | 7.52E−08 |
| 5 | 4.41E−08 |
| 6 | 2.68E−08 |
| 7 | 2.75E−08 |
| 8 | 6.07E−09 |
| 9 | 1.12E−07 |
| 10 | 3.53E−08 |
| 11 | 3.94E−08 |
| 12 | 6.10E−09 |
| 13 | 3.79E−07 |
| 14 | 6.61E−09 |
| 15 | 2.20E−07 |
| 16 | 4.42E−08 |
| 17 | 8.43E−08 |
| 18 | 1.13E−08 |
| 19 | 8.22E−08 |
| 20 | 1.37E−07 |
| 21 | 6.88E−09 |
| Intermediate (10) | 6.54E−08 |
| Intermediate (13) | 3.74E−08 |
| 22 | 1.18E−07 |
| 23 | 4.65E−08 |
| 24 | 1.24E−08 |
| 25 | 4.57E−08 |
| 26 | 6.01E−09 |
| 27 | 3.40E−08 |
| 28 | 3.37E−08 |
| 29 | 7.53E−08 |
| 30 | 2.74E−08 |
| 31 | 3.49E−08 |
| 32 | 6.55E−08 |
| 33 | 3.26E−08 |
| 34 | 9.87E−08 |
| 35 | 1.36E−07 |
| 36 | 4.85E−08 |
| 37 | 7.14E−08 |

Example 39

This example illustrates how to study the efficacy of the compounds of this invention in increasing the wakefulness in animal models.

Male Sprague Dawley rats (Charles River, France) weighing 250±10 g are anaesthetized with ZOLETIL® 50 (60 mg/kg ip) and mounted in a stereotaxic apparatus. Cortical electrodes (small stainless steel screw electrodes of 0.9 mm in diameter) are screwed into the bone over the sensorimotor cortex (1.5 mm lateral to the median suture and 1.5 mm behind the fronto-parietal suture), the visual cortex (1.5 mm lateral to the median suture and 1.5 mm in front of the parieto-occipital suture) and over the cerebellum (reference electrode). Cortical electrodes are attached to a connector (Winchester, 7-lead) and fixed with dental cement to the cranium.

After three weeks of post-operative recovery, animals are placed in plexiglass cylinders (60 cm diameter) with free access to food and water. The temperature of the room is kept constant (21±1° C.) and lights are on from 7 a.m. to 7 p.m. The rats are recorded from 10 a.m. to 4 p.m. during three consecutive days: control day (D1), drug day (D2) and post drug day (D3). Vehicle (D1 and D3) or drug (D2) are administered 15 min before the recording.

Activity in sensorimotor and visual cortices are recorded by comparison with the reference electrode placed over the cerebellar cortex. Three stages are differentiated:
- wakefulness (W) characterized by low voltage fast electrocortical (ECoG) activity;
- NREM sleep (non rapid eye movement or slow wave sleep: SWS) characterized by an increase in electrocortical activity; development of high-amplitude slow waves with some bursts of sleep spindles;
- REM sleep (rapid eye movement or paradoxical sleep: PS) characterized by hypersynchronization of the theta rhythm in the visual area.

Analysis of the ECoG signal is performed automatically by means of a computerized system discriminating between the various sleep phases using sequential spectral analysis of ten seconds periods (Deltamed's software "Coherence").

The compounds of this invention can be dissolved in 0.6% MTC tween and administered by oral route (po). The volume of injection is usually about 0.5 ml/100 g of body weight.

Two types of analysis can be used to quantify the effects of the compounds of this invention on sleep-wakefulness variables: the one hour-period and the six hour-period analysis.

The results are expressed in minutes (one hour-period analysis) or as the percentage of the control values (100%). Statistical analysis of the data can be carried out using the Student's t test for paired values to determine significant variations from control values.

Example 40

Stress-Induced Ultrasonic Vocalizations Test in Adult Rats

This example illustrates how to study the efficacy of the compounds of this invention as antidepressive agents in animal models.

The procedure used can be adapted from the technique described by Van Der Poel A. M, Noach E. J. K, Miczek K. A (1989) Temporal patterning of ultrasonic distress calls in the adult rat: effects of morphine and benzodiazepines. Psychopharmacology 97:147-8. Rats are placed for a training session in a cage with a stainless steel grid floor (MED Associates, Inc., St. Albans, Vt.). Four electric shocks (0.8 mA, 3 s) are delivered every 7 s and ultrasonic vocalizations (UV, 22 KHz) are subsequently recorded with the Ultravox system (Noldus, Wageningen, The Netherlands) during 2 min. A modified ultrasound detector (Mini-3 bat model) connected to a microphone is used to transform ultrasonic sound into audible sound. The signal is then filtered and sent to a computer where the Ultravox software recorded each bout of UV that lasted more than 10 ms. Rats are selected on the basis of their UV duration (>40 s) and subjected to the test, 4 h after training. For the test, rats are placed in the same cage as that used for training. One electric shock (0.8 mA, 3 s) is delivered and UV (duration and frequency) are subsequently recorded with the Ultravox system during 2 min. The compounds of this invention can be administered p.o. 60 min before testing.

Example 41

Forced-Swimming Test in Rats

This example further illustrates how to the study of efficacy of the compounds of this invention as antidepressive agents in animal models.

The procedure that can be used is a modification of that described by Porsolt et al. (1977) Depression: a new animal model sensitive to antidepressant treatments. Nature 266: 730-2. Rats are placed in individual glass cylinder (40 cm height, 17 cm diameter) containing water (21° C.) to a height of 30 cm. Two swimming sessions are conducted (a 15-min training session followed 24 h later by a 6-min test). After each swimming session, rats are placed under a heating lamp to avoid hypothermia. The duration of immobility is measured during the 6-min test. The compounds of this invention can be administered p.o. twice (15 min after training session and 60 min before the test).

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:
1. A compound of formula (Ia):

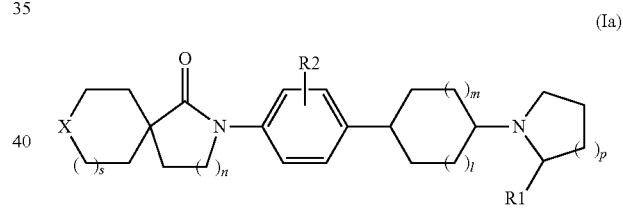

wherein:
l is 0 or 1;
m and p independently of each other are;
n is 0, 1 or 2;
s is 0 or 1;
X is O, $NR_5$ or $CHR_6$;
$R_1$ is hydrogen, $(C_1-C_4)$alkyl or $CF_3$;
$R_2$ is hydrogen, halogen, $(C_1-C_4)$alkyl, $(C_1-C_4)$alkoxy or $CF_3$;
$R_5$ is hydrogen, $(C_1-C_4)$alkyl or tert-butyloxycarbonyl (t-BOC); and
$R_6$ is hydrogen, OH or COOR; and wherein
R is hydrogen or $(C_1-C_4)$alkyl;
or a salt thereof or an enantiomer or a diastereomer thereof.
2. The compound according to claim 1, wherein
m is 1;
l and s independently of each other are 0 or 1;
n is 0, 1 or 2;
p is 1;
X is O, $CH_2$, CHOH, $CH_3OCOCH$, NH or t-BOC-N;
$R_1$ is hydrogen or $CH_3$; and
$R_2$ is hydrogen or fluorine;
or a salt thereof or an enantiomer or a diastereomer thereof.

3. The compound of claim 1 selected from the group consisting of:
- 2-{4-[(S)-3-((S)-2-methyl-pyrrolidin-1-yl)-cyclopentyl]-phenyl}-8-oxa-2-aza-spiro[4.5]decan-1-one;
- 2-{4-[(S)-3-((S)-2-methyl-pyrrolidin-1-yl)-cyclopentyl]-phenyl}-2-aza-spiro[4.5]decan-1-one;
- 2-{4-[3-(2-methyl-pyrrolidin-1-yl)-cyclopentyl]-phenyl}-1-oxo-2,9-diaza-spiro[5.5]undecane-9-carboxylic acid tert-butyl ester;
- 8-hydroxy-2-{4-[3-(2-methyl-pyrrolidin-1-yl)-cyclopentyl]-phenyl}-2-aza-spiro[4.5]decan-1-one;
- 2-{4-[3-(2-methyl-pyrrolidin-1-yl)-cyclopentyl]-phenyl}-1-oxo-2-aza-spiro[4.5]decane-8-carboxylic acid methyl ester;
- 2-{4-[3-(2-methyl-pyrrolidin-1-yl)-cyclopentyl]-phenyl}-1-oxo-2,8-diaza-spiro[4.5]decane-8-carboxylic acid tert-butyl ester;
- 7-{4-[3-(2-methyl-pyrrolidin-1-yl)-cyclopentyl]-phenyl}-7-aza-spiro[4.5]decan-6-one; and
- 2-{4-[3-(2-methyl-pyrrolidin-1-yl)-cyclopentyl]-phenyl}-2,9-diaza-spiro[5.5]undecan-1-one;

or a salt thereof.

4. A pharmaceutical composition comprising a compound of formula (Ia) according to claim 1 or a pharmaceutically acceptable salt thereof or an enantiomer or a diastereomer thereof in combination with at least one pharmaceutically acceptable excipient, diluent or a carrier.

5. The composition according to claim 4, wherein the compound is selected from the group consisting of:
- 2-{4-[(S)-3-((S)-2-methyl-pyrrolidin-1-yl)-cyclopentyl]-phenyl}-8-oxa-2-aza-spiro[4.5]decan-1-one;
- 2-{4-[(S)-3-((S)-2-methyl-pyrrolidin-1-yl)-cyclopentyl]-phenyl}-2-aza-spiro[4.5]decan-1-one;
- 2-{4-[3-(2-methyl-pyrrolidin-1-yl)-cyclopentyl]-phenyl}-1-oxo-2,9-diaza-spiro[5.5]undecane-9-carboxylic acid tert-butyl ester;
- 8-hydroxy-2-{4-[3-(2-methyl-pyrrolidin-1-yl)-cyclopentyl]-phenyl}-2-aza-spiro[4.5]decan-1-one;
- 2-{4-[3-(2-methyl-pyrrolidin-1-yl)-cyclopentyl]-phenyl}-1-oxo-2-aza-spiro[4.5]decane-8-carboxylic acid methyl ester;
- 2-{4-[3-(2-methyl-pyrrolidin-1-yl)-cyclopentyl]-phenyl}-1-oxo-2,8-diaza-spiro[4.5]decane-8-carboxylic acid tert-butyl ester;
- 7-{4-[3-(2-methyl-pyrrolidin-1-yl)-cyclopentyl]-phenyl}-7-aza-spiro[4.5]decan-6-one; and
- 2-{4-[3-(2-methyl-pyrrolidin-1-yl)-cyclopentyl]-phenyl}-2,9-diaza-spiro[5.5]undecan-1-one; or a pharmaceutically acceptable salt thereof.

\* \* \* \* \*